(12) United States Patent
Boyle et al.

(10) Patent No.: US 7,674,890 B2
(45) Date of Patent: Mar. 9, 2010

(54) STEM CELL FACTOR-LIKE PROTEINS AND USES THEREOF

(75) Inventors: Bryan J. Boyle, Santa Clara, CA (US); Peter C. R. Emtage, Edmonton (CA); Walter Funk, Hayward, CA (US); Y. Tom Tang, Beverly, MA (US); Jingsong Zhao, Fremont, CA (US)

(73) Assignee: Arca Biopharma, Inc., Broomfield, CO (US)

( * ) Notice: Subject to any disclaimer, the term of this patent is extended or adjusted under 35 U.S.C. 154(b) by 52 days.

(21) Appl. No.: 12/080,212

(22) Filed: Apr. 1, 2008

(65) Prior Publication Data

US 2008/0200388 A1    Aug. 21, 2008

Related U.S. Application Data

(63) Continuation of application No. 11/334,081, filed on Jan. 17, 2006, now Pat. No. 7,439,327.

(60) Provisional application No. 60/645,354, filed on Jan. 18, 2005.

(51) Int. Cl.
| | |
|---|---|
| *C12N 15/11* | (2006.01) |
| *A61K 38/00* | (2006.01) |
| *C12N 15/63* | (2006.01) |
| *C12P 21/06* | (2006.01) |
| *C07K 14/00* | (2006.01) |

(52) U.S. Cl. .......................... 536/23.1; 514/2; 435/69.1; 435/320.1; 530/350

(58) Field of Classification Search ....................... None
See application file for complete search history.

(56) References Cited

U.S. PATENT DOCUMENTS

2005/0054829 A1    3/2005    Wiley et al.

FOREIGN PATENT DOCUMENTS

| EP | 1440981 A2 | 7/2004 |
|---|---|---|
| WO | WO 03/020932 A1 | 3/2003 |
| WO | WO 03/029405 | 4/2003 |

OTHER PUBLICATIONS

Altschul, et al., "Basic Local Alignment Search Tool," *J Mol Biol* 215:403-410 (1990).
Altshcul, "A Protein Alignment Scoring System Sensitive at All Evolutionary Distances," *J Mol Evol* 36:290-300 (1993).
Berthrong, "Pathologic Changes Secondary to Radiation," *World J Surg* 10:155-170 (1986).
Bork, "Powers And Pitfalls In Sequence Analysis: The 70% Hurdle," *Genome Research* 10:398-400 (2000).
Bork, et al., "Go Hunting In Sequence Databases But Watch Out For The Traps," *Trends In Genetics* 12:425-427 (1996).
Bouma, "The Immunological and Genetic Basis of Inflammatory Bowel Disease," *Nature Rev* 3:521-533 (2003).
Boushey, et al., "Glucagon-Like Peptide (GLP)-2 Reduces Chemotherapy-Associated Mortality and Enhances Cell Survival in Cells Expressing a Transfected GLP-2 Receptor," *Cancer Res* 61:687-693 (2001).
Brenner, "Errors In Genome Annotation," *Trends in Genetics* 15:132-133 (1999).
Dibaise, et al., "Intestinal Rehabilitation and the Short Bowel Syndrome: Part 2," *Am J Gastroenterol* 99:1823-1832 (2004).
Doerks, et al., "Protein annotation: detective work for function prediction," *Trends in Genetics* 14:248-250 (1998).
Farrell, et al., "The Effects of Keratinocyte Growth Factor in Preclinical Models of Mucositis," *Cell Prolif* 35(suppl 1): 78-85 (2002).
Garnier, et al., "Scale-up of the Adenovirus Expression System for the Produstion of Recombinant Protein in Human 293S Cells," *Cytotechnology* 15:145-155 (1994).
Guzman-Stein, et al., "Abonminal Radiation Causes Bacterial Translocation," *J Surg Res* 46:104-107 (1989).
Han, et al., Keratinocyte Growth Factor-2 (FGF-10) Promotes Healing of Experimental Small Intestinal Ulceration in Rats, *Am J Gastrointest Liver Physiol* 279:G1011-G1022 (2000).
Helmrath, et al., "Intestinal Adaption Following Massive Small Bowel Resection in the Mouse," *J Am Coll Surg* 183:441-449 (1996).
Jeffers, et al., "A Novel Human Fibroblast Growth Factor Treats Experimental Intestinal Inflammation," *Gastroenterology* 123:1151-1162 (2002).
Kazanskaya, et al., "R-Spondin2 is a Secreted Activator of Wnt/β-Catenin Signaling and is Required for Xenopus Myogenisis," *Dev Cell* 7:525-534 (2004).
Kilpeláinen, et al., "Heparin-Binding Growth-Associated Molecule Contains Two Heparin-Binding β-Sheet Domains the are Homologous to the Thrombospondin Type I Repeat," *J Biol Chem* 275:13564-13570 (2000).
Krieglstein, et al., "Collagen-Binding Integrin $\alpha_1\beta_1$ Regulates Intestinal Inflammation in Experimental Colitis," *J Clin Invest* 110:1773-1782 (2002).
Lawler, "The Functions of Thrombospondin-1 and -2," *Curr Opin Cell Biol* 12:634-640 (2000).
L'Heureux, et al., "Glucagon-Like Polypeptide-ommon Therapeutics in a Murine Model of Ulcerative Colitis," *J Pharmacol Exp Ther* 306 :347-354 (2003).
Long, et al., "Thrombospondin Functions as a Cytoadhesion Molecule for Human Hematopoietic Progenitor Cells," *Blood* 75:2311-2318 (1990).
McGinley, et al., "Effect of Fixation and Epitope Retrieval on BrdU Indices in Mammary Carcinomas," *J Histochem Cytochem* 48:355-362 (2000).
Moore, "Clonogenic Response of Cells of Murine Intestinal Crypts to 12 Cytotoxic Drugs," *Cancer Chemother Pharmacol* 15:11-15 (1985).

(Continued)

*Primary Examiner*—Jeffrey Stucker
*Assistant Examiner*—Aditi Dutt
(74) *Attorney, Agent, or Firm*—Robins & Pasternak LLP

(57) ABSTRACT

The invention relates to pharmaceutical compositions comprising gastrointestinal proliferative factor SCFA2, SCFA4 or SCFA4v polynucleotides and polypeptides. The invention further relates to the therapeutic use of SCFA2, SCFA4 or SCFA4v to prevent or treat conditions or disorders associated with the degeneration of the epithelial mucosa.

11 Claims, 16 Drawing Sheets

OTHER PUBLICATIONS

Figure 1:
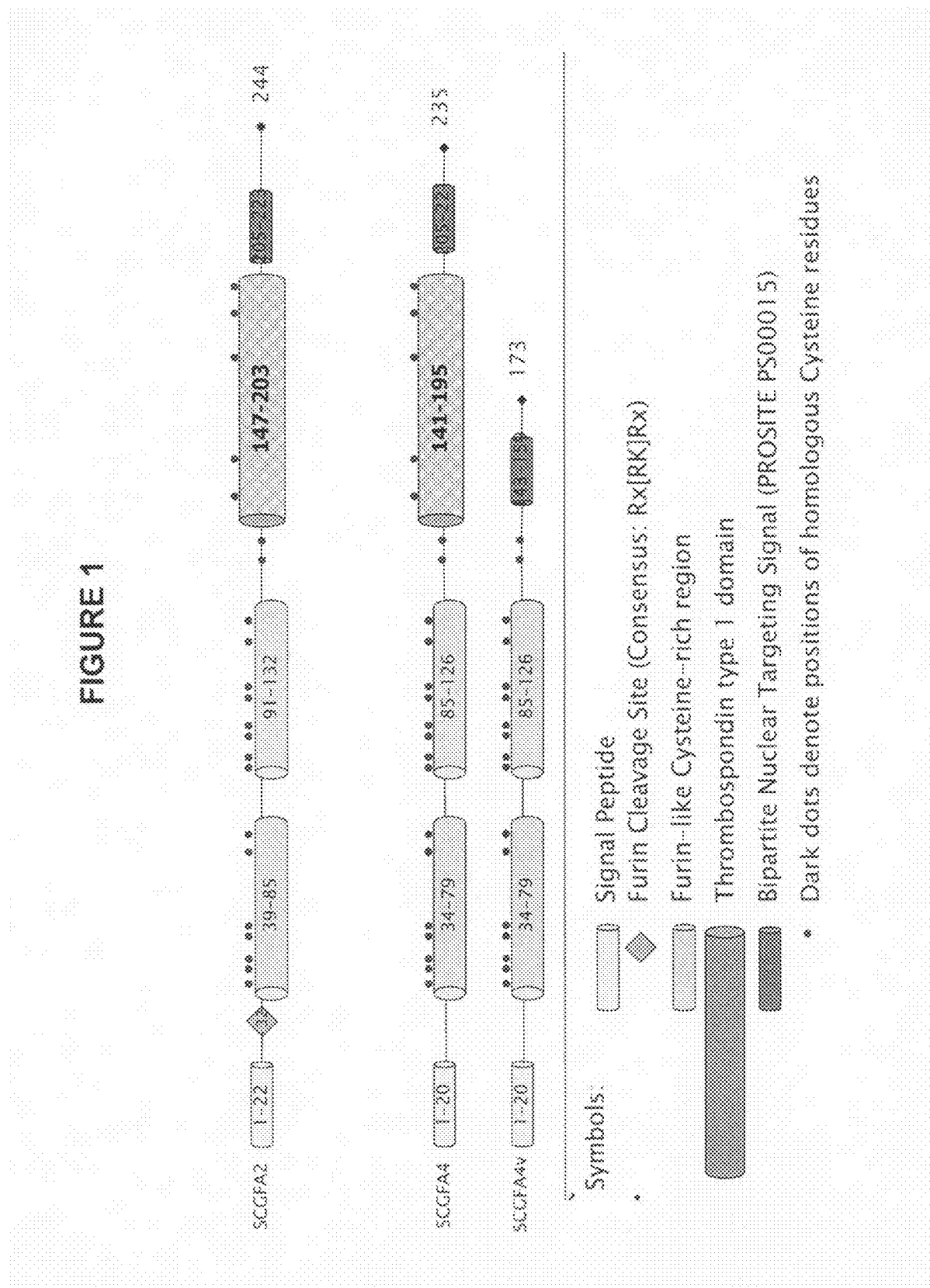

Neurath, et al., "Antibodies to Interleukin 12 Abrogate Established Experimental Colitis in Mice," *J Exp Med* 182:1281-1290 (1995).

Neilsen, et al., "A Neural Network Method for Identification of Prokaryotic and Eukaryotic Signal Peptides and Prediction of Their Cleavage Sites," *Int J Neural Syst* 8:581-599 (1997).

Ngo, et al., The Protein Folding Problem and Tertiary Structure Prediction pp. 491-495 (1994).

Potten, et al., "Cell Kinetic Studies in the Murine Ventral Tongue Epithelium: Mucositis Induced by Radiation and its Protection by Pretreatment with Keratinocyte Growth Factor (KGF)," *Cell Prolif* 35(Suppl 1):32-47 (2002).

Raz, et al., "Interallelic Complementation Among DER/flb Allelles: Implications for the Mechanism of Signal Transduction by Receptor-Tyrosine Kinases," *Genetics* 129:191-201(1991).

Scholzen, et al., "The Ki-67 Protein: From the Known and the Unknown," *J Cell Physiol* 182:311-322 (2000).

Scott, et al., "GLP-2 Augments the Adaptive Response to Massive Intestinal Resection in Rat," *Am J Physiol* 275:G911-G921 (1998).

Siegmund, et al., "Adenosine Kinase Inhibitor GP515 Improves Experimental Colitis in Mice," *J Pharmacol Exp Ther* 296:99-105 (2001).

Skolnick, et al., "From Genes To Protein Structure And Function: Novel Applications Of Computational Approaches In The Genomic Era," *Trends in Biotech* 18(1):34-39 (2000).

Smith, et al., "The Challenges Of Genome Sequence Annotation Or The Devil Is In The Details," *Nature Biotechnology* 15:1222-1223 (1997).

Sonis, et al., "An Animal Model for Mucositis Induced by Cancer Chemotherapy," *Oral Surg Oral Med Oral Pathol* 69:437-443 (1990).

Sonhammer, et al., "Pfam Multiple Sequence Alignments and HMM-Profiles of Protein Domains," *Nucl Acids Res* 26:320-322 (1998).

Wardley, et al., "A Quantitative Histometric Murine In Vivo Model of Radiation Induce Oral Mucocitid," *Arch Oral Biol* 43:567-577 (1998).

Wells, "Additivity of mutational effects in proteins," *Biochemistry* 29:8509-8517 (1990).

Whitehead, et al., "Clonogenic Growth of Epithelial Cells from Normal Colonic Mucosa From Both Mice and Humans," *Gastroenterology* 117:858-865 (1999).

Withers, et al., "Microcolony Survival Assay for Cells of Mouse Intestinal Mucosa Exposed to Radiation," *Int J Radiat Biol Relat Stud Phys Chem Med* 17:261-267 (1970).

Zhou, et al., "Proteolytic Processing in the Secretory Pathway," *J Biol Chem* 274:20745-20748 (1999).

Database EPO Proteins [Online], EBI Accession No. EPOP:CQ843580, "Sequence 2227 from Patent EP1440981," (2004).

Database Geneseq [Online], EBI Accession No. GSP:ADY56840, "Human Thrombospondin-30b (1-198) Protein Fragment," (2005).

Database Geneseq [Online], EBI Accession No. GSP:ABR62106, "Secreted Stem Cell Growth Factor-Like Protein #13," (2003).

Kamata, et al., "R-Spondin, A Novel Gene with Thrombospondin Type 1 Domain, was Expressed in the Dorsal Neural Tube and Affected in Wnts Mutants," *Biochim Biophys Acta* 1676(1):51-62 (2004).

Kim, et al., "R-Spondin Proteins: A Novel Link to Beta -Catenin Activation," *Cell Cycle* 5(1):23-26 (2006).

Database EPO Proteins [Online], EBI Accession No. GSP:ADB76146, "Novel Human Secretory Protein C," (2003).

SCFA4v (SEQ ID NO: 23)                                          172 aa vs.

>gi|14627121|emb|CAB65783.3|dJ824F16.3 (novel protein similar to mouse
thrombospondin type I domain protein R-spondin) [Homo sapiens]
(SEQ ID NO: 48) 224 aa 69.2% identity;      Global alignment score: 1060

10        20        30        40        50        60

SCFA4v  MRAPLCLLLLVAHAVDMLALNRRKKQVGTGLGGNCTGCIICSEENGCSTCQQRLFLFIRR

::::::::::::::::::::::::::::::::::::::::::::::::::::::::::::

gi|146  MRAPLCLLLLVAHAVDMLALNRRKKQVGTGLGGNCTGCIICSEENGCSTCQQRLFLFIRR 10        20        30        40        50        60

70        80        90       100       110       120

SCFA4v  EGIRQYGKCLHDCPPGYFGIRGQEVNRCKKCGATCESCFSQDFCIRCKRQFYLYKGKCLP

::::::::::::::::::::::::::::::::::::::::::::::::::::::::::::

gi|146  EGIRQYGKCLHDCPPGYFGIRGQEVNRCKKCGATCESCFSQDFCIRCKRQFYLYKGKCLP 70        80        90       100       110       120

130

SCFA4v  TCPPGTLAHQNTRECQ--------------------------------------------

::::::::::::::::

gi|146  TCPPGTLAHQNTRECQGECELGPWGGWSPCTHNGKTCGSAWGLESRVREAGRAGHEEAAT 130       140       150       160       170       180

140       150       160       170

SCFA4v  -----------------ERSPGQKKGRKDRRPRKDRKLDRRLDVRPRQPGLQP

:::::::::::::::::::::::::::::::::

gi|146  CQVLSESRKCPIQRPCPGERSPGQKKGRKDRRPRKDRKLDRRLD---------

190       200       210       220

FIGURE 2

```
   M Q F R L F S F A L I I L N C M D Y S H C Q G N R W R R S K   scfa2
   M R A P L C - L L L L V A H A V D M L A L N - - - - R R K K   scfa4
   M R A P L C - L L L L V A H A V D M L A L N - - - - R R K K   scfa4v 1 R A S Y V S N P I C K G C L S C S K D N G C S R C Q Q K L F   scfa2
 6 Q V G T G L G G N C T G C I I C S E E N G C S T C Q Q R L F   scfa4
 6 Q V G T G L G G N C T G C I I C S E E N G C S T C Q Q R L F   scfa4v 1 F F L R R E G M R Q Y G E C L H S C P S G Y Y G H R A P D M   scfa2
 6 L F I R R E G I R Q Y G K C L H D C P P G Y F G I R G Q E V   scfa4
 6 L F I R R E G I R Q Y G K C L H D C P P G Y F G I R G Q E V   scfa4v 1 N R C A R C R I E N C D S C F S K D F C T K C K V G F Y L H   scfa2
 6 N R C K K C G A T - C E S C F S Q D F C I R C K R Q F Y L Y   scfa4
 6 N R C K K C G A T - C E S C F S Q D F C I R C K R Q F Y L Y   scfa4v 21 R G R C F D E C P D G F A P L E E T M E C V E G C E V G H W   scfa2
15 K G K C L P T C P P G T L A H Q N T R E C Q G E C E L G P W   scfa4
15 K G K C L P T C P P G T L A H Q N T R E C Q - - - - - - -    scfa4v 51 S E W G T C S R N N R T C G F K W G L E T R T R Q I V K K P   scfa2
45 G G W S P C T H N G K T C G S A W G L E S R V R E A G R A G   scfa4
37 - - - - - - - - - - - - - - - - - - - - - - - - - - - -    scfa4v 81 V K D T I P C P T I A E S R R C K M T M R H C P G K R T P   scfa2
75 H E E A A T C Q V L S E S R K C P I - Q R P C P G - E R S P   scfa4
37 - - - - - - - - - - - - - - - - - - - - - - - - E R S P   scfa4v 11 K A K E K R N K K K K R K L I E R A Q E Q H S V F L A T D R   scfa2
03 G Q K K G R K D R R P R K - - D R K L D R R L D V R P Q P   scfa4
41 G Q K K G R K D R R P R K - - D R K L D R R L D V R P Q P   scfa4v 41 A N Q                                                       scfa2
31 G L Q P                                                     scfa4
69 G L Q P                                                     scfa4v
```

Decoration 'Decoration #1': Box residues that match the Consensus exactly.

⟷ Signal Peptide (aa1-22 in scfa2 and aa1-20 in scfa4, scfa4v)
| Furin cleavage site (between aa32 and aa33 in scfa2 only)
⟶ Furin-like cysteine-rich domains (aa39-85, 91-132 in scfa2, 34-79, 91-132 in scfa4, scfa4v)
⟵■ Thrombospondin type1 domain (aa147-203 in scfa2, aa147-195 in scfa4, - in scfa4v)
⟶● Bipartite Nuclear Targeting Signal (aa205-223 in scfa2, 205-221 in scfa4, 143-149 in scfa4v)

FIGURE 3

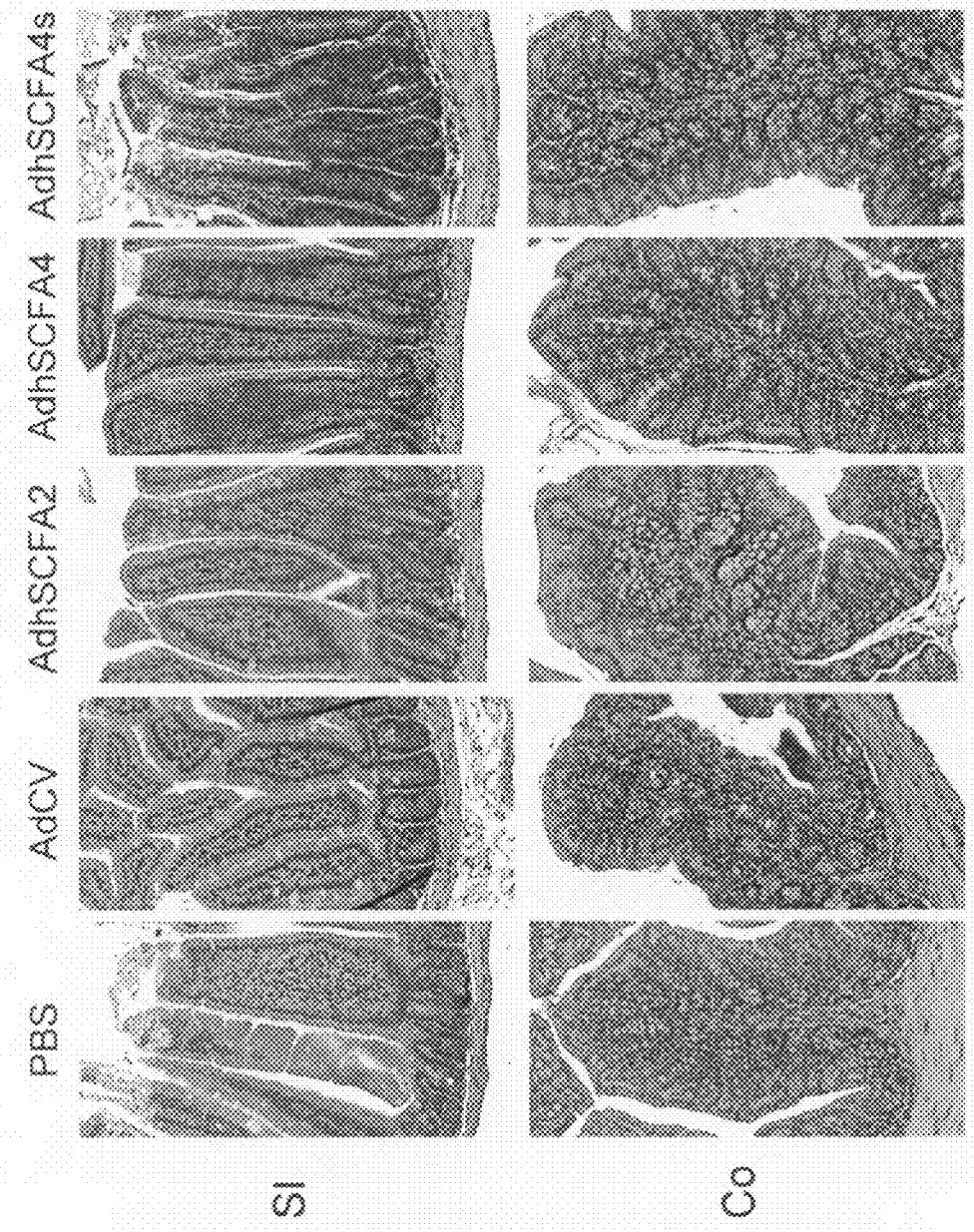

FIGURE 6
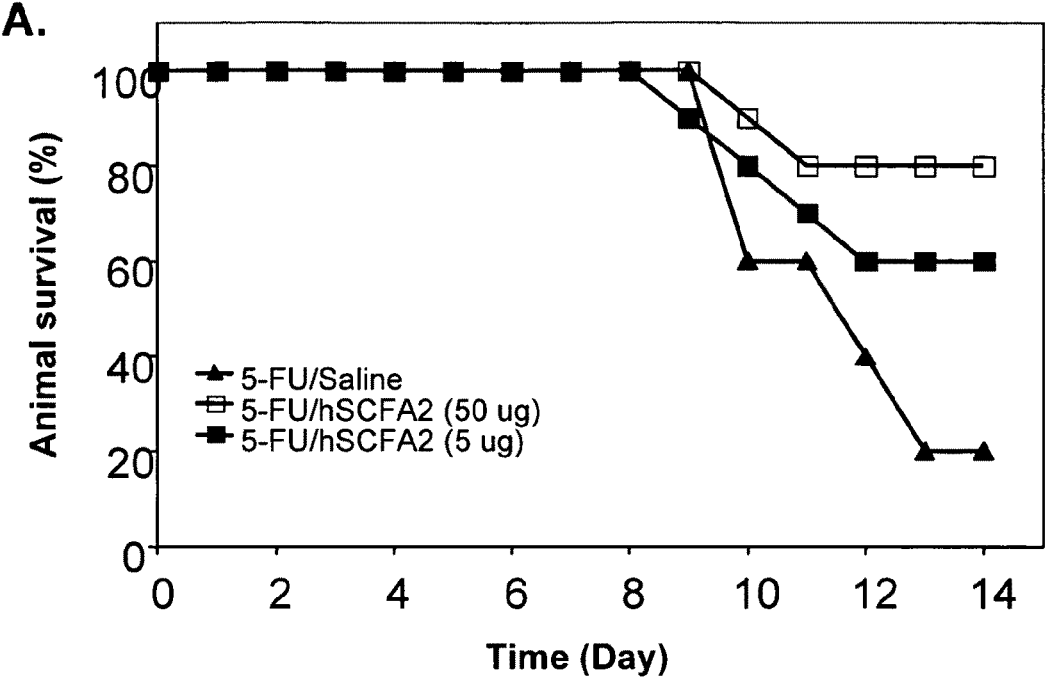
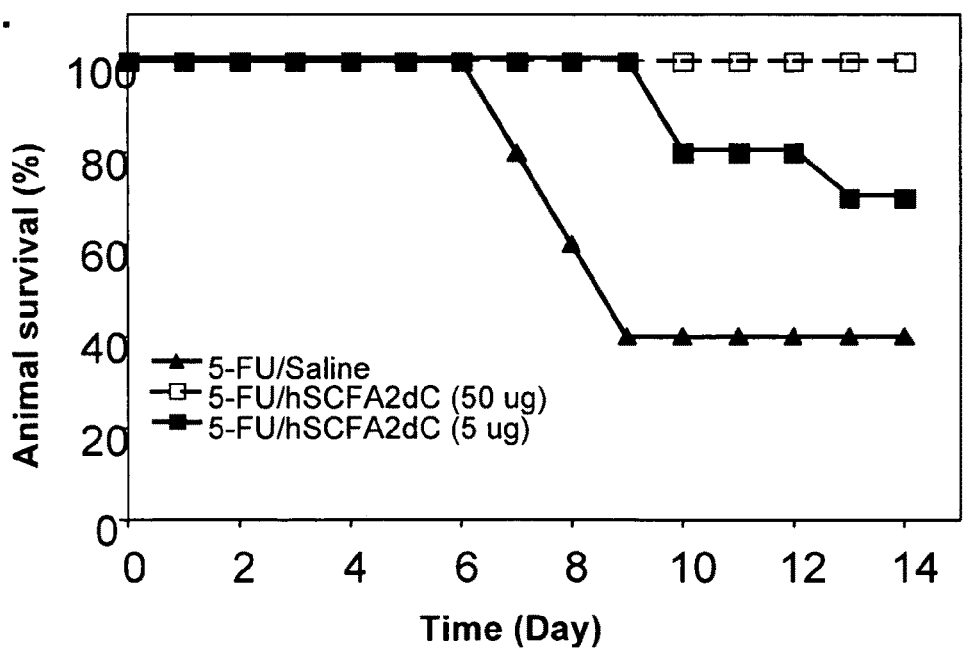

FIGURE 7
A.
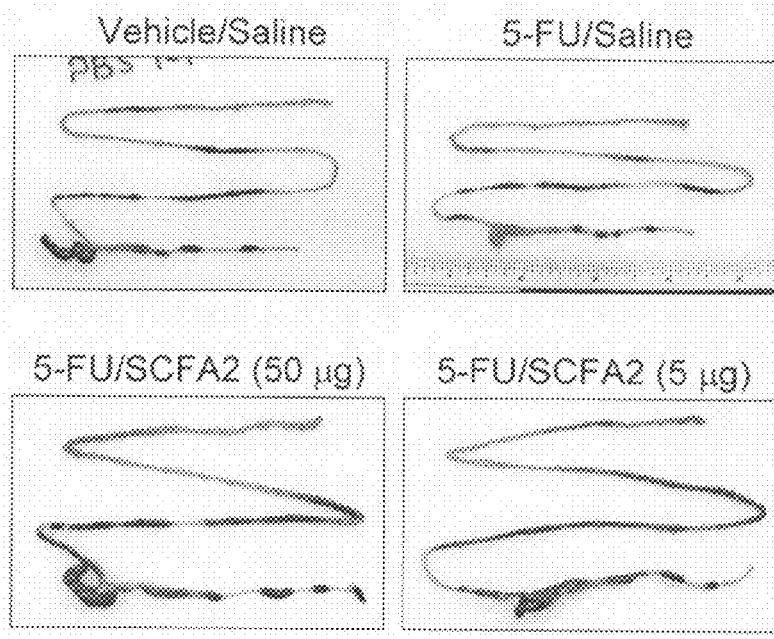
B.
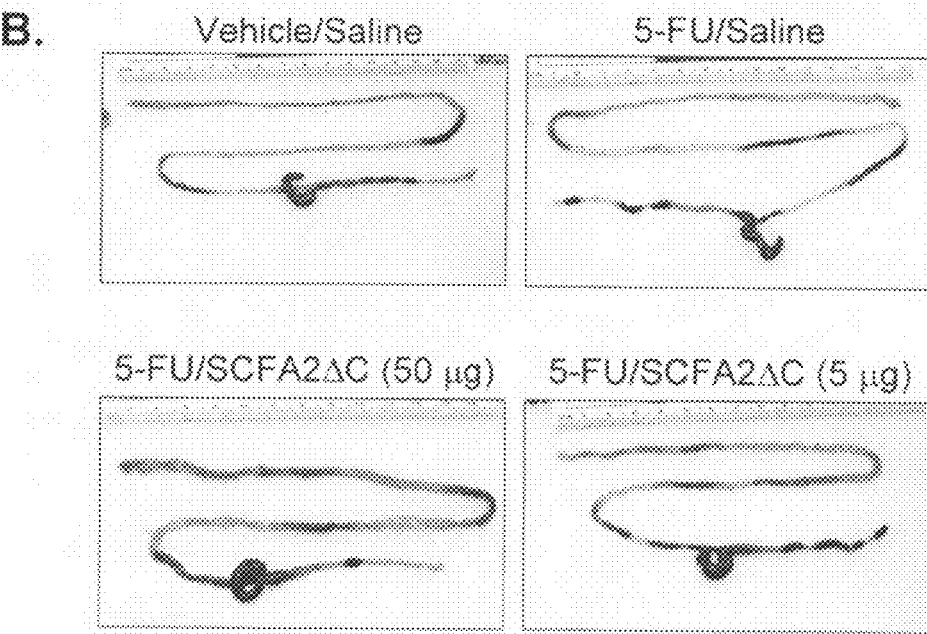

FIGURE 8
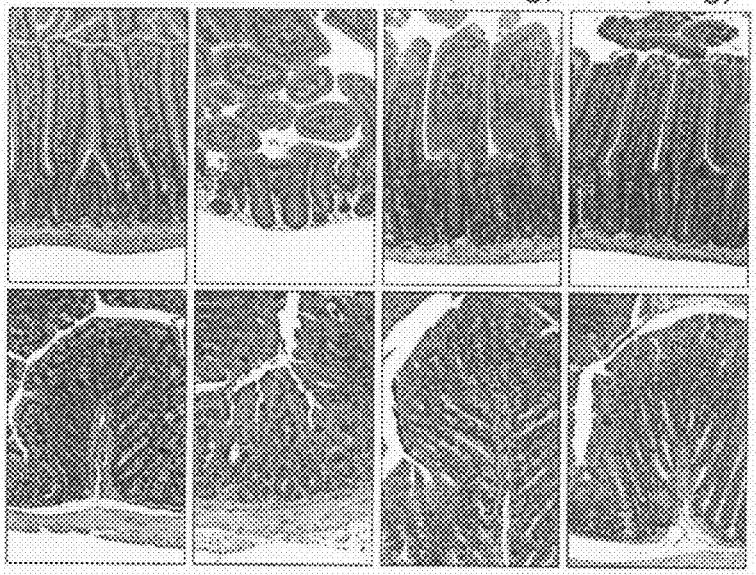
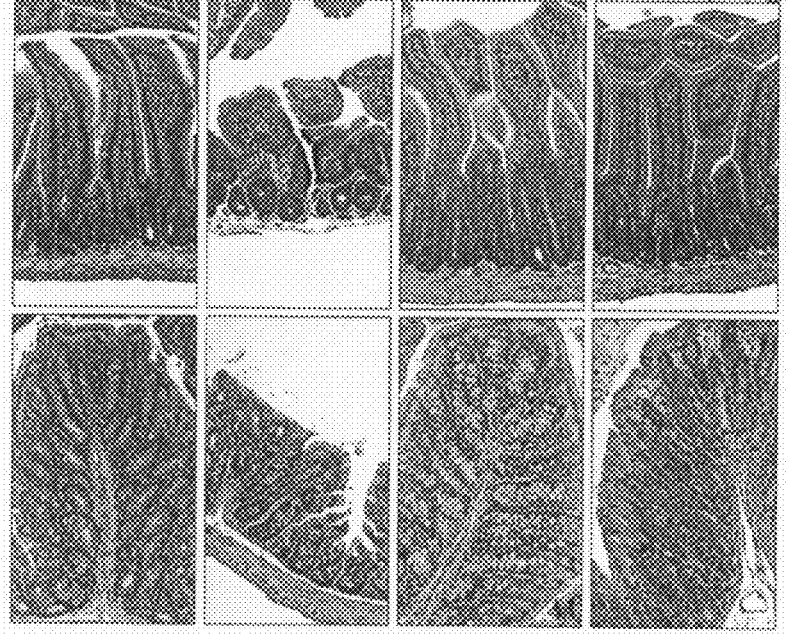

FIGURE 9
A.
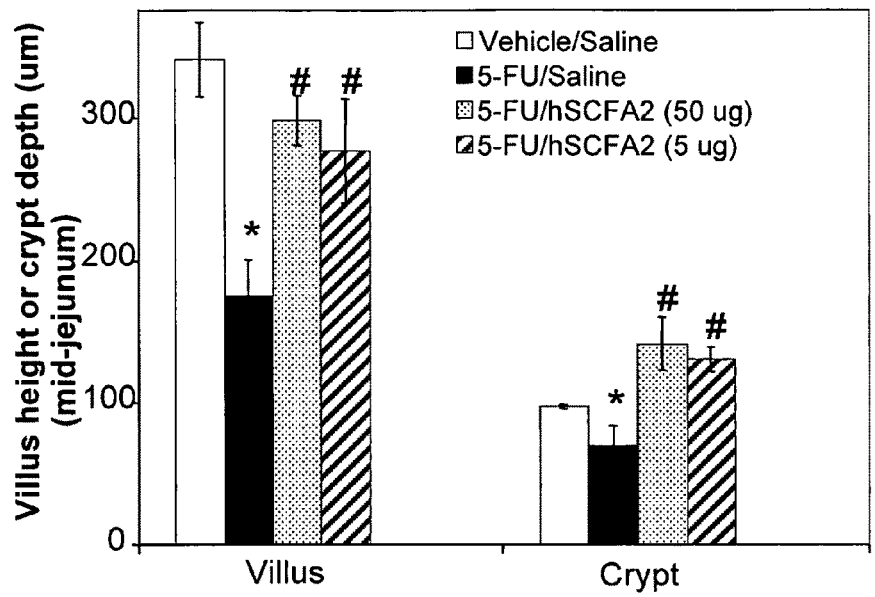
*$P < 0.05$ (ANOVA, Vehicle/Saline vs. 5-FU/Saline)
$P < 0.05$ (ANOVA, 5-FU/Saline vs. 5-FU/hSCFA2 groups)
B.
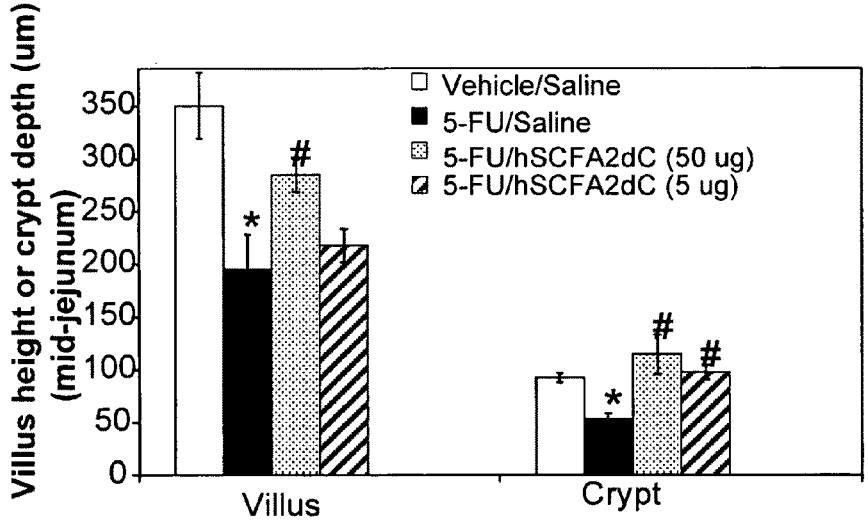
*$P < 0.05$ (ANOVA, Vehicle/Saline vs. 5-FU/Saline)
$P < 0.05$ (ANOVA, 5-FU/Saline vs. 5-FU/hSCFA2dC groups)

FIGURE 10
A.
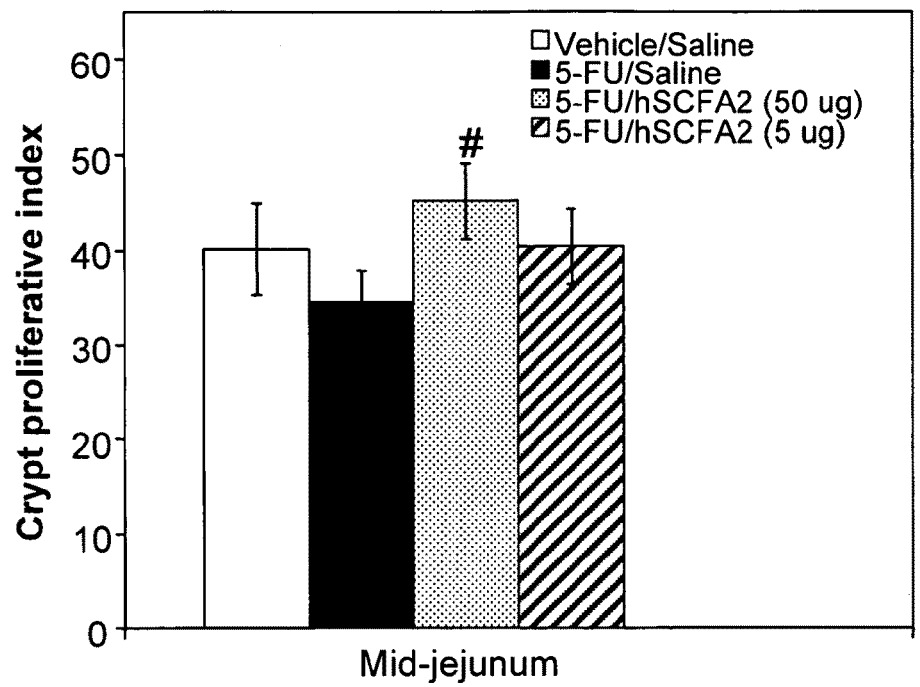
$\#P < 0.05$ (ANOVA, 5-FU/Saline vs. 5-FU/hSCFA2 groups)
B.
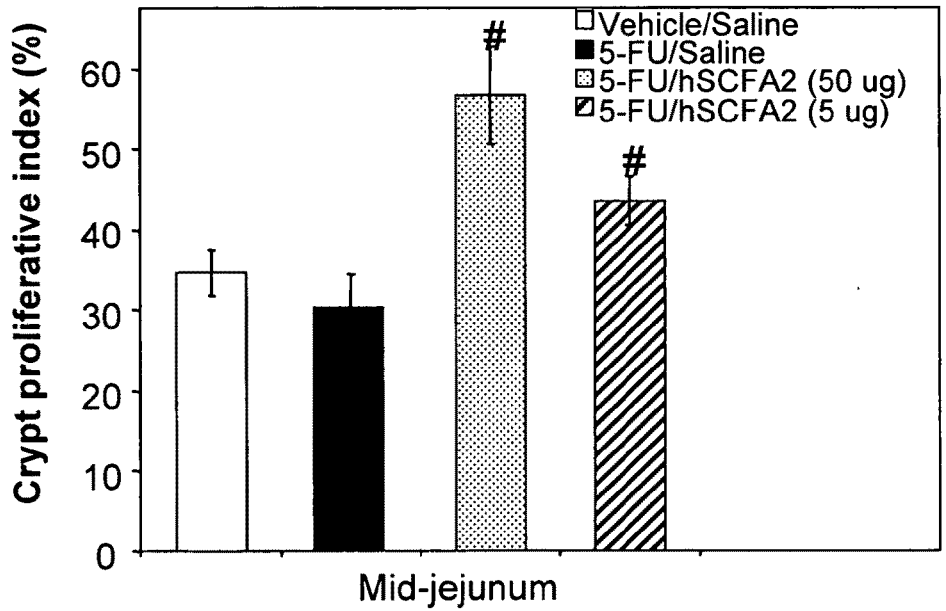
$\#P < 0.05$ (ANOVA, 5-FU/Saline vs. 5-FU/hSCFA2dC groups)

FIGURE 11
A.
Vehicle/Saline
5-FU/Saline
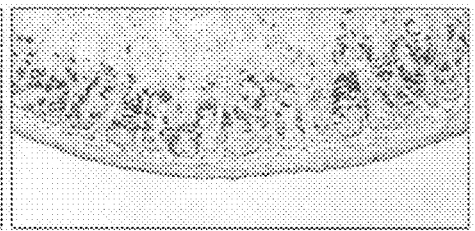
5-FU/SCFA2 (50 µg)
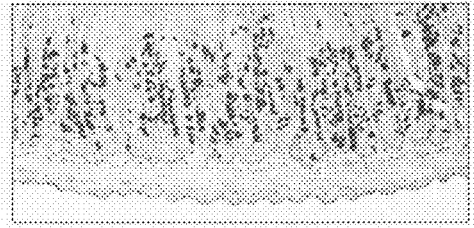
5-FU/SCFA2 (5 µg)
B.
Vehicle/Saline
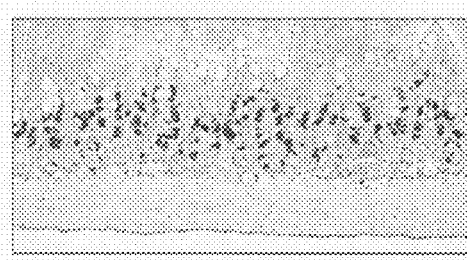
5-FU/Saline
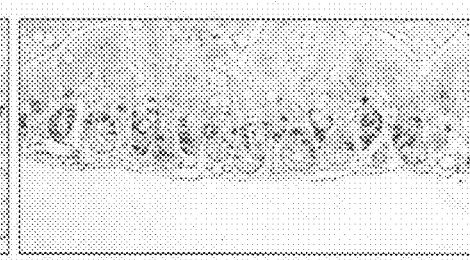
5-FU/A2ΔC (50 µg)
5-FU/A2ΔC (5 µg)

FIGURE 12
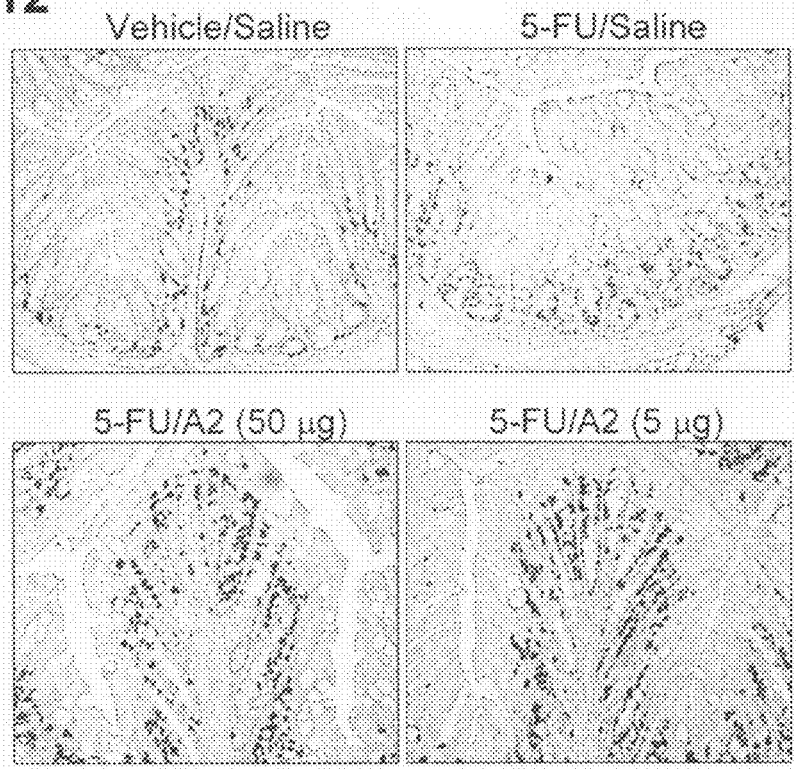
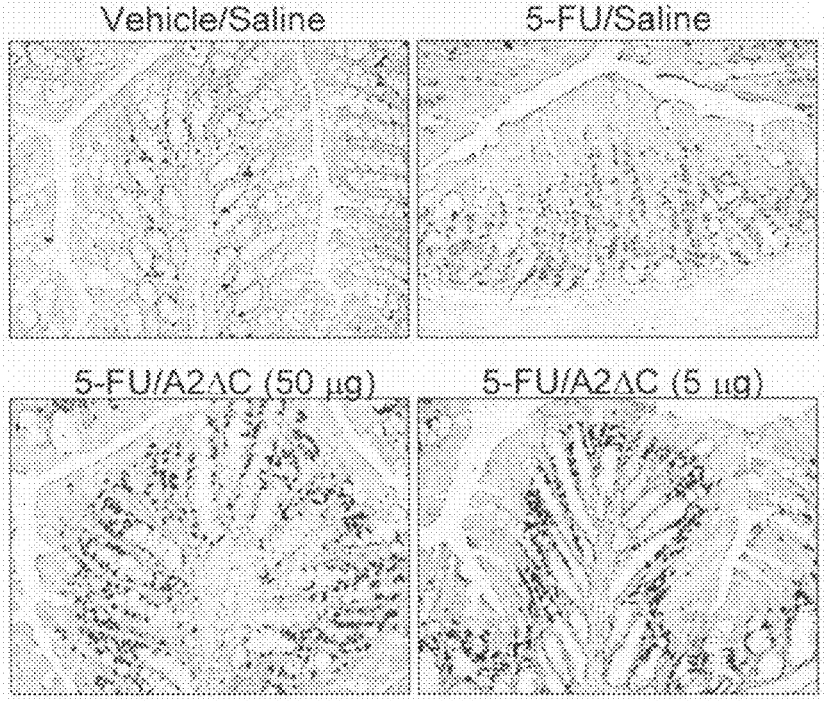

FIGURE 13
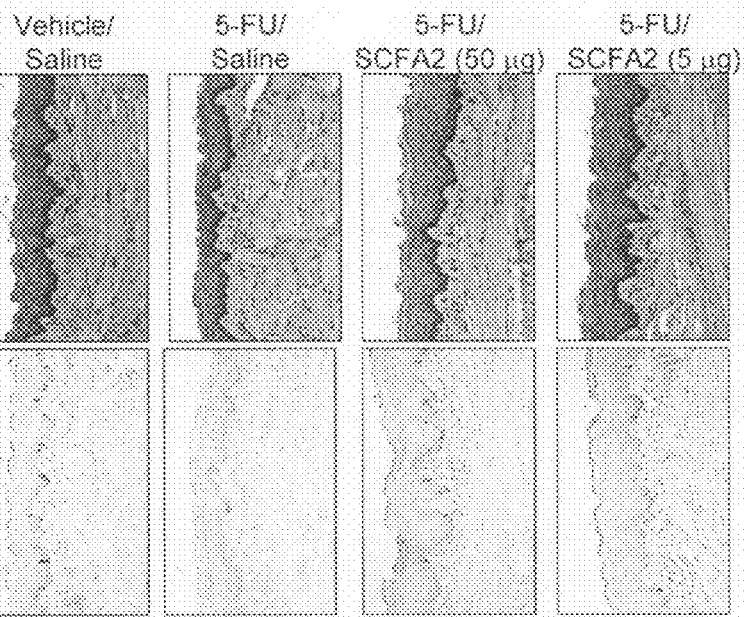
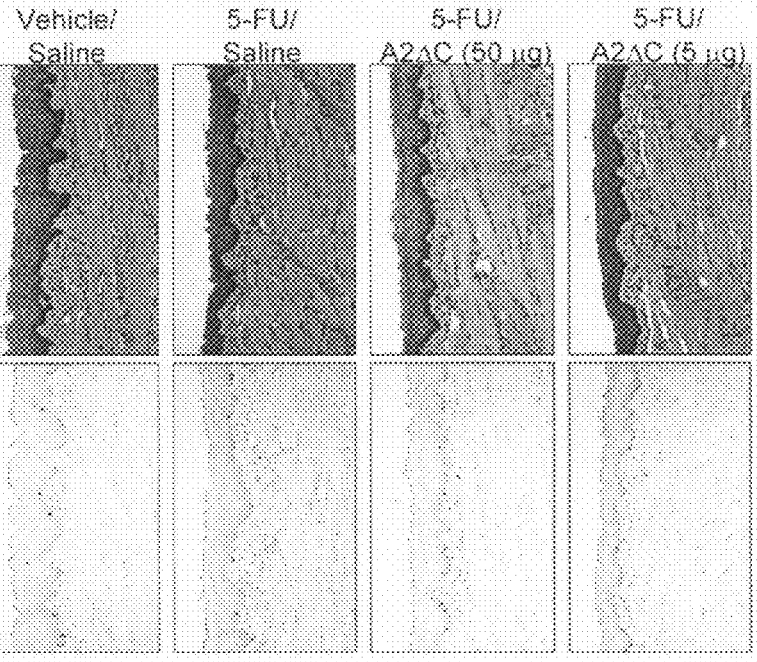

FIGURE 14
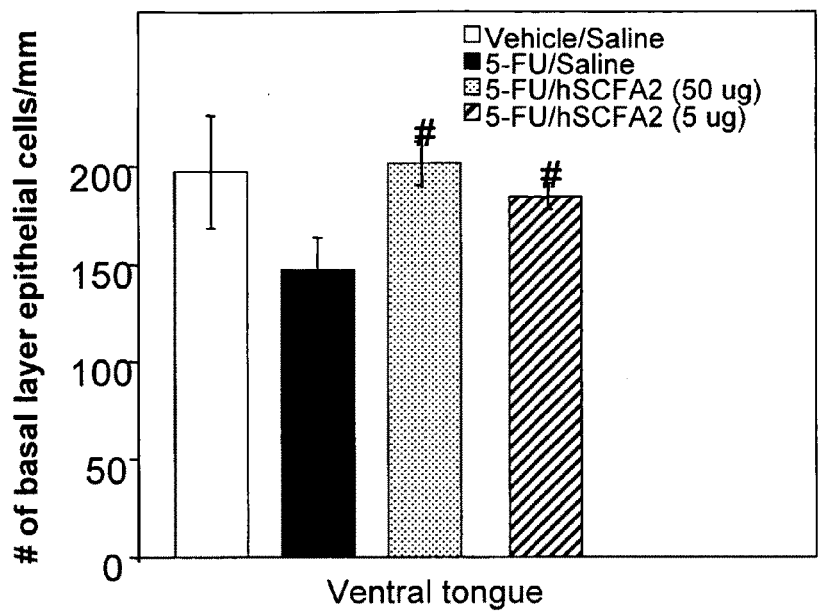
A.
$^\#P < 0.05$ (ANOVA, 5-FU/Saline vs. 5-FU/hSCFA2 groups)
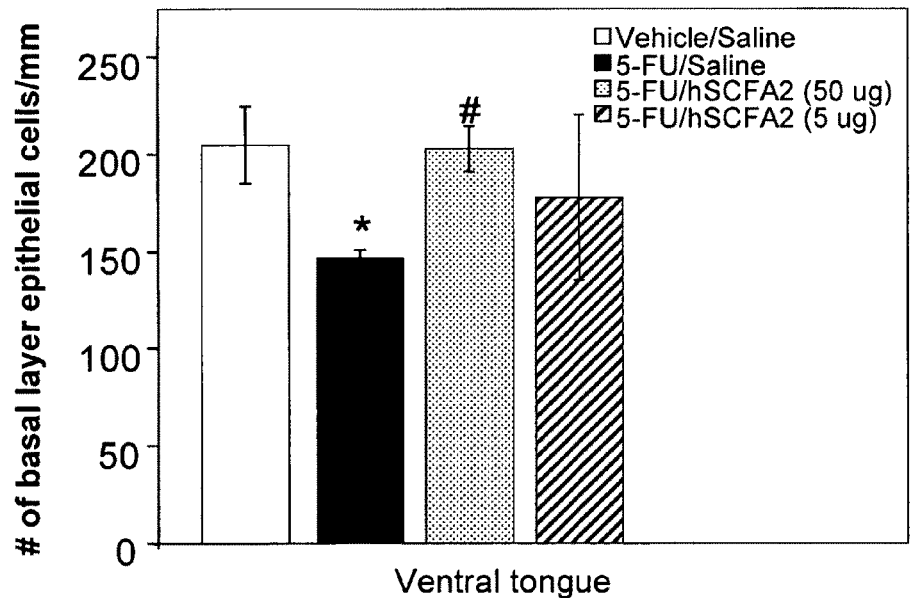
B.
$^*P < 0.05$ (ANOVA, Vehicle/Saline vs. 5-FU/Saline)
$^\#P < 0.05$ (ANOVA, 5-FU/Saline vs. 5-FU/hSCFA2dC groups)

FIGURE 15
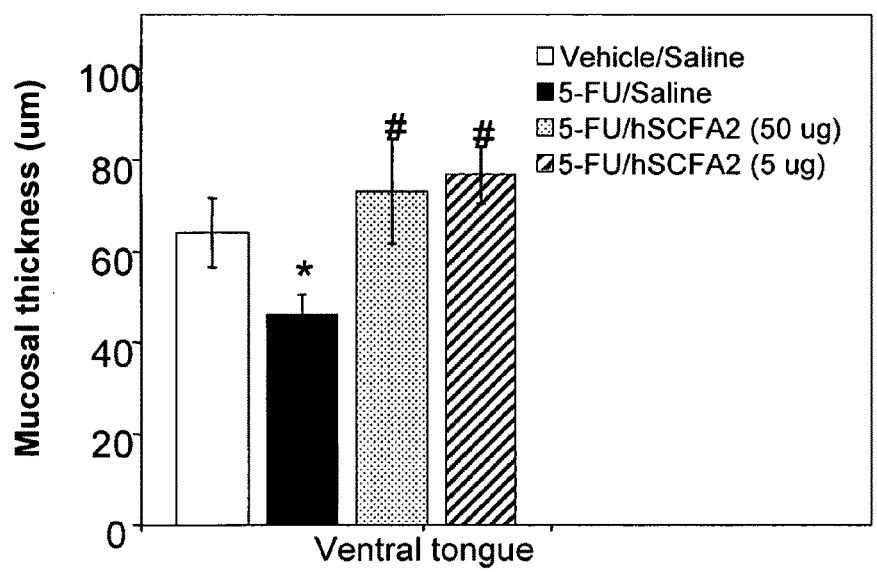
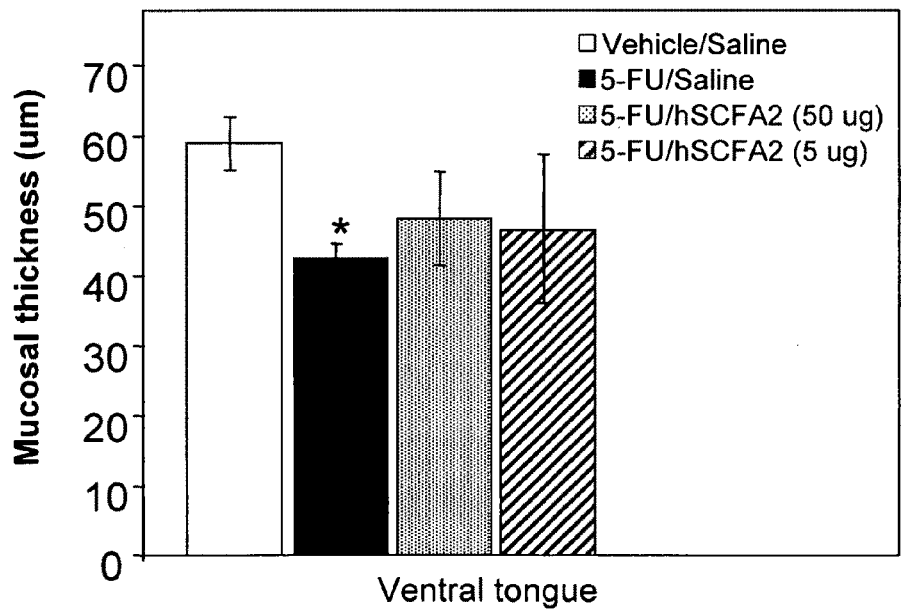

FIGURE 16
A.
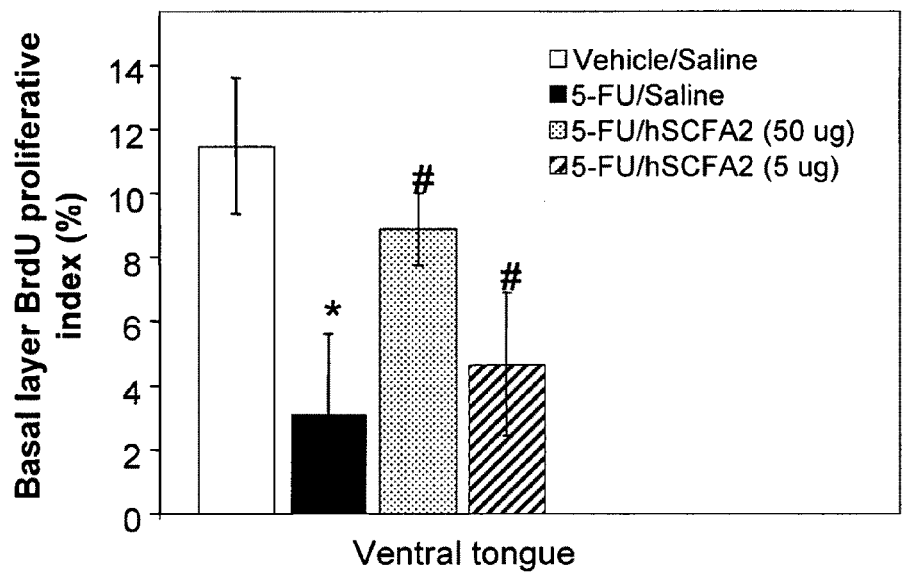
*$P < 0.05$ (ANOVA, Vehicle/Saline vs. 5-FU/Saline)
$P < 0.05$ (ANOVA, 5-FU/Saline vs. 5-FU/hSCFA2 groups)
B.
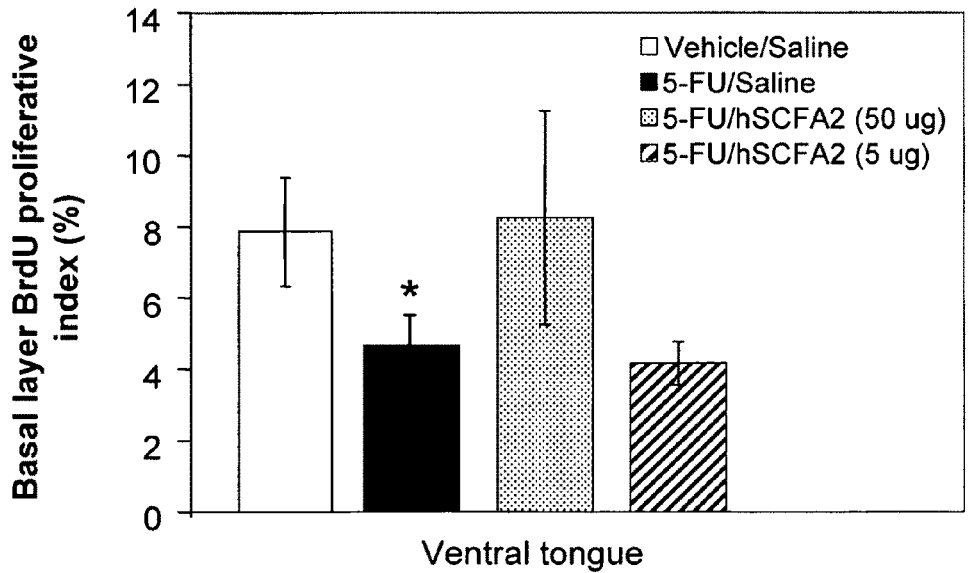
*$P < 0.05$ (ANOVA, Vehicle/Saline vs. 5-FU/Saline)

US 7,674,890 B2

STEM CELL FACTOR-LIKE PROTEINS AND USES THEREOF

This application is a continuation application of U.S. patent application Ser. No. 11/334,081, filed Jan. 17, 2006, issued as U.S. Pat. No. 7,439,327, dated Oct. 21, 2008 from which application priority is claimed pursuant to 35 U.S.C. §120, which in turn claims benefit under 35 U.S.C. §119(e) of provisional application 60/645,354, filed Jan. 18, 2005, which applications are hereby incorporated by reference in their entireties.

1. BACKGROUND 1.1 Field of the Invention

The present invention provides a method for augmenting proliferation of gastrointestinal epithelial cells. The invention further provides a method for treating or preventing mucositis in patients undergoing cancer treatment, to treat patients with inflammatory bowel disease, and to ameliorate digestion and nutritional absorption of patients with short bowel syndrome.

1.2 Sequence Listing

The sequences of the polynucleotides and polypeptides of the invention are listed in the Sequence Listing and are submitted on a compact disc containing the file labeled "NUVO-21A.ST25.txt"—94.0 KB (96,256 bytes) which was created on an IBM PC, Windows 2000 operating system on Jan. 17, 2006 at 5:14:37 PM. The Sequence Listing entitled "NUVO-21A.ST25.txt" is herein incorporated by reference in its entirety. A computer readable format ("CRF") and three duplicate copies ("Copy 1/2" and "Copy 2/2") of the Sequence Listing "NUVO-221A.ST25.txt" are submitted herein. Applicants hereby state that the content of the CRF and Copies 1/1 and 2/2 of the Sequence Listing, submitted in accordance with 37 CFR §1.821 (c) and (e), respectively, are the same.

1.3 Background

Ionizing radiation therapy and cytotoxic chemotherapy produce injuries to the oral and gastrointestinal mucosa, which remain significant problems for patients undergoing antineoplastic treatments. Mucositis is the inflammation of the mucous membranes and is a particularly common problem in this patient population due to the use of chemotherapy and radiation therapy used with curative or palliative intent. The mucosal injuries to the gastrointestinal tract seen with radiation and chemotherapy (to these areas) include the destruction of crypt cells, a decrease in villous height and ulceration and necrosis of the gastrointestinal epithelium (Berthrong M, World J Surg 10:155-170 (1986)), which underlie disorders including gastrointestinal mucositis and enterocolitis. To the patients this can mean abdominal pain, bloody diarrhea, malabsorption and in some cases bacterial translocation (Guzman et al., J Surg Res 46:104-107 (1989)). In addition, chemotherapy and ionizing radiation can affect other mucous membranes including those of the oropharynx and lips, and those of the esophagus. It is well known that combined modality therapy of concurrent radiation and chemotherapy can produce highly symptomatic stomatitis in patients with head and neck cancer, and esophagitis in patients with small cell lung cancer.

Chemotherapy and radiation therapy cause injury to the oral and gastrointestinal mucosa through direct and indirect toxicity. The mechanism for direct mucositis is nonspecific cell killing of rapidly dividing basal epithelial cells that results in epithelial thinning, inflammation, decreased cell renewal, and ultimately ulceration. These painful lesions also produce an increased risk for local and systemic infection. Indirect mucotoxicity is a byproduct of chemotherapy-induced myelosuppression, which permits bacterial and viral infections at the site of direct mucosal injury. The severity of these effects may preclude dose escalation, delay treatment, and warrant dose reductions, thus limiting the effectiveness of cancer therapy.

A well-established prophylaxis or therapy for chemotherapy and radiation therapy-induced (mucosal) gastrointestinal injuries (mucositis) is unavailable, other than a prescription of suboptimal doses of chemotherapy or radiotherapy, a downward dose modification in subsequent treatment courses following toxicity, or the use of specific antidotes such as leucovorin after moderate-dose or high-dose methotrexate (Allegra CJ. Antifolates. In: Chabner and Collins, eds. Cancer Chemotherapy: Principles and Practice. Philadelphia, Pa. JP Lippincott Co; 1990:110-153.)

Injury to the gastrointestinal mucosa is also associated with chronic inflammatory disorders of the gastrointestinal tract, which are collectively referred to as inflammatory bowel disease. While cytokine-based therapies are available for the treatment of inflammatory bowel disease, none can be considered as a permanent cure (Bouma and Strober Nature Rev 3:521-533 (2003)). Often resection of the small intestine is indicated in patients with inflammatory bowel disease such as Crohn's disease. Surgical resection of the small intestine may also be necessary following traumatic injury, vascular accidents, and cancer. Surgical resection that leaves less than 200 cm of viable small bowel places a patient at risk for developing short-bowel syndrome (SBS). SBS is a disorder that is clinically defined by malabsorption, diarrhea, fluid and electrolyte disturbances, and malnutrition. The management of patients with SBS frequently requires long-term, if not life long use of parenteral nutrition DiBaise et al., Am J Gastroenterol 99:1823-1832 (2004)).

Thus, there is a need to find agents that may be used prophylactically or therapeutically to increase the tolerance to anteneoplastic treatments, to advance current therapies for treating inflammatory bowel disease, and to restore the digestive and absorptive processes that are compromised following surgical resection of the intestine.

To this end Applicants have discovered an agent that induces the proliferation of gastrointestinal epithelial cells, and which may be useful for treating conditions in which proliferation of epithelial cells may be desired.

2. SUMMARY OF THE INVENTION

The present invention is based on the discovery that stem cell factor-like proteins SCFA2, SCFA4 and SCFA4v induce the proliferation of epithelial cells of the gastrointestinal tract. Thus, compositions comprising SCFA2, SCFA4 or SCFA4v, fragments or analogs thereof, may be used for the treatment of conditions where epithelialization is required, such as for the treatment of gastrointestinal disorders including chemotherapy and radiation therapy-induced mucositis, mucositis of the oropharynx, lips and esophagus, inflammatory bowel disease, and other conditions including wounds, burns, ophthalmic disorders, and any disorder where stimulation of epithelial cell proliferation or regeneration is desired.

The polynucleotide (SEQ ID NO: 22) which encodes the polypeptide of SEQ ID NO: 23, is novel. Therefore, one embodiment of the invention is directed to the polynucleotde of SEQ ID NO: 22. The invention also comprises vectors that comprise the polynucleotde sequence of SEQ ID NO: 22, a host cell that comprises the polynucleotide of SEQ ID NO: 22, a transgene construct that comprise the polynucleotide sequence of SEQ ID NO: 22; and a method for detecting the polynucleotide of SEQ ID NO: 22 in a sample.

Another embodiment is directed to the polypeptide of SEQ ID NO: 23, a fragment or analog thereof. The invention also comprises a method for producing the polypeptide of SEQ ID NO: 23, fragment or analog thereof; a method for detecting the polypeptide of SEQ ID NO: 23 in a sample, a method for identifying a compound that binds the polypeptide of SEQ ID NO: 23, fragment or analog thereof.

In another embodiment, the invention is directed to a composition comprising a therapeutically effective amount of a SCFA2 (SEQ ID NO: 3, 6, 8, 10, 12, 36, 51 or 55), SCFA4 (SEQ ID NO: 14, 17, 19, 21, or 40) or SCFA4v (SEQ ID NO: polypeptide (SEQ ID NO: 23, 26, or 44) and a pharmaceutically acceptable carrier.

The compositions of the present invention include isolated polynucleotides (SEQ ID NO: 1, 2, 4, 5, 7, 9, 11, 13, 15, 16, 18, 20, 22, 24, 25, 35, 39, 43, 50, 52, 53, or 54) encoding SCFA2, SCFA4 or SCFA4v polypeptides, including recombinant DNA molecules, and cloned genes or degenerate variants thereof, especially naturally occurring variants such as allelic variants. The compositions of the present invention also include vectors such as expression vectors containing the polynucleotides of the invention, cells genetically engineered to contain such polynucleotides and cells genetically engineered to express such polynucleotides.

The compositions of the invention comprise isolated polynucleotides that include, but are not limited to, a SCFA2, SCFA4 or SCFA4v polynucleotide, a fragment, or variant thereof; a polynucleotide comprising the full length protein coding sequence of the SEQ ID NO: 2, 13, or 22 (for example, SEQ ID NO: 4, 14, or 23); a polynucleotide comprising the nucleotide sequence of the dominant mature protein coding sequence of SEQ ID NO: 5, 16, or 25 (for example SEQ ID NO: 6, 17, or 26); a polynucleotide comprising the nucleotide sequence of the mature protein coding sequence of SEQ ID NO: 7 (for example SEQ ID NO: 8); a polynucleotide comprising the nucleotide sequence of the C-terminal deletion protein of SCFA2 coding sequence of SEQ ID NO: 50 (for example SEQ ID NO: 51); a polynucleotide comprising the nucleotide sequence of the thrombospondin domain of SEQ ID NO: 11 or 20 (for example SEQ ID NO: 12 or 21); a polynucleotide of SEQ ID NO: 9 or 18 comprising the nucleotide sequence that encodes furin-like cysteine-rich domains (for example SEQ ID NO: 10 or 19). The polynucleotide compositions of the present invention also include, but are not limited to, a polynucleotide that hybridizes under stringent hybridization conditions to (a) the complement of any of the nucleotide sequences set forth in SEQ ID NO: 1, 2, 4, 5, 7, 9, 11, 13, 15, 16, 18, 20, 22, 24, 25, 35, 39, 43, 50, 52, 53, or 54 (b) a nucleotide sequence encoding any of SEQ ID NO: 3, 6, 8, 10, 12, 14, 17, 19, 21, 23, 26, 36, 40, 44, 51, or 55; a polynucleotide which is an allelic variant of any polynucleotides recited above having at least 70% polynucleotide sequence identity to the polynucleotides; a polynucleotide which encodes a species homolog (e.g. ortholog) of any of the peptides recited above; or a polynucleotide that encodes a polypeptide comprising a specific domain or truncation of the polypeptide of SEQ ID NO: 3, 14, or 23.

This invention further provides cloning or expression vectors comprising at least a fragment of the polynucleotides set forth above and host cells or organisms transformed with these expression vectors. Useful vectors include plasmids, cosmids, lambda phage derivatives, phagemids, and the like, that are well known in the art. Accordingly, the invention also provides a vector including a polynucleotide of the invention and a host cell containing the polynucleotide. In general, the vector contains an origin of replication functional in at least one organism, convenient restriction endonuclease sites, and a selectable marker for the host cell. Vectors according to the invention include expression vectors, replication vectors, probe generation vectors, and sequencing vectors. A host cell according to the invention can be a prokaryotic or eukaryotic cell and can be a unicellular organism or part of a multicellular organism.

The pharmaceutical compositions of the present invention include polypeptides comprising, but not limited to, an isolated polypeptide selected from the group comprising the amino acid sequence of SEQ ID NO: 3, 6, 8, 10, 12, 14, 17, 19, 21, 23, 26, 36, 40, 44, 51 or 55. Polypeptides of the invention also include polypeptides with biological activity that are encoded by (a) any of the polynucleotides having a nucleotide sequence set forth in the SEQ ID NO: 1, 2, 4, 5, 7, 9, 11, 13, 15, 16, 18, 20, 22, 24, 25, 35, 39, 43, 50, 52, 53, or 54 above; or (b) polynucleotides that hybridize to the complement of the polynucleotides of (a) under stringent hybridization conditions. Biologically or immunologically active analogs of any of the protein sequences listed as SEQ ID NO: 3, 6, 8, 10, 12, 14, 17, 19, 21, 23, 26, 36, 40, 44, 51, or 55, and substantial equivalents thereof that retain biological are also contemplated. The polypeptides of the invention may be wholly or partially chemically synthesized but are preferably produced by recombinant means using the genetically engineered cells (e.g. host cells) of the invention.

The invention also relates to methods for producing a SCFA2, SCFA4 or SCFA4v polypeptide comprising culturing host cells comprising an expression vector containing at least a fragment of a SCFA2, SCFA4 or SCFA4v polynucleotide encoding the SCFA2, SCFA4 or SCFA4v polypeptide of the invention in a suitable culture medium under conditions permitting expression of the desired polypeptide, and purifying the protein or peptide from the culture or from the host cells. Preferred embodiments include those in which the protein produced by such a process is a mature or dominant mature form of the protein.

The polypeptides according to the invention can be used in a variety of conventional procedures and methods that are currently applied to other proteins. For example, a polypeptide of the invention can be used to generate an antibody that specifically binds the polypeptide. Such antibodies, particularly monoclonal antibodies, are useful for detecting or quantifying the polypeptide in tissue.

In further embodiments, the subject invention is directed to a method of stimulating epithelial cell proliferation. The method comprises contacting epithelial cells with a composition that includes a therapeutically effective amount of a SCFA2, SCFA4 or SCFA4v polypeptide, fragment or analog thereof, and a pharmaceutically acceptable carrier. Specifically, a subject in need of stimulation (including cytoprotection, proliferation and/or differentiation) of epithelial cells will be administered therapeutically-effective or prophylactically-effective amounts of SCFA2, SCFA4 or SCFA4v protein, fragments or analogs thereof.

In all the methods described, epithelial cells may be contacted with the SCFA2, SCFA4 or SCFA4v polypeptides in vitro or in vivo.

Methods are also provided for preventing, treating, or ameliorating a medical condition which comprises the step of administering to a mammalian subject a therapeutically effective amount of a composition comprising a peptide of the present invention and a pharmaceutically acceptable carrier.

In particular, the SCFA2, SCFA4 or SCFA4v polypeptides of the invention may be used to induce the proliferation and/or differentiation of gastrointestinal crypt cells to regenerate the epithelial layer of the alimentary tract. Thus, the SCFA2, SCFA4 or SCFA4v polypeptides and polynucleotides of the invention may be used in the treatment of chemotherapy or radiation therapy-induced mucositis and enterocolitis, and inflammatory bowel disease. They may also be used in the treatment of diseases, and other conditions including wounds, burns, ophthalmic disorders, and any disorder where stimulation of epithelial cell proliferation or regeneration is desired.

Polynucleotides and polypeptides of the invention may also be used as markers of differentiation and development of gastrointestinal epithelium.

The methods of the invention also provide methods for the treatment of disorders as recited herein which comprise the administration of a therapeutically effective amount of a composition comprising a polynucleotide or polypeptide of the invention and a pharmaceutically acceptable carrier to a mammalian subject exhibiting symptoms or tendencies related to disorders as recited herein. In addition, the invention encompasses methods for treating diseases or disorders as recited herein comprising the step of administering a composition comprising compounds and other substances that modulate the overall activity of the target gene products and a pharmaceutically acceptable carrier. Compounds and other substances can effect such modulation either on the level of target gene/protein expression or target protein activity. Specifically, methods are provided for preventing, treating or ameliorating a medical condition, including mucositis and inflammatory bowel disease, wounds, which comprises administering to a mammalian subject, including but not limited to humans, a therapeutically effective amount of a composition comprising a polypeptide of the invention or a therapeutically effective amount of a composition comprising a binding partner of SCFA2, SCFA4 or SCFA4v polypeptides of the invention. The mechanics of the particular condition or pathology will dictate whether the polypeptides of the invention or binding partners of these would be beneficial to the individual in need of treatment.

The invention further provides methods for manufacturing medicaments useful in the above-described methods.

The present invention further relates to methods for detecting the presence of the polynucleotides or polypeptides of the invention in a sample (e.g., tissue or sample). Such methods can, for example, be utilized as part of prognostic and diagnostic evaluation of disorders as recited herein and for the identification of subjects exhibiting a predisposition to such conditions.

The invention provides a method for detecting a polypeptide of the invention in a sample comprising contacting the sample with a compound that binds to and forms a complex with the polypeptide under conditions and for a period sufficient to form the complex and detecting formation of the complex, so that if a complex is formed, the polypeptide is detected.

The invention also provides kits comprising polynucleotide probes and/or monoclonal antibodies, and optionally quantitative standards, for carrying out methods of the invention. Furthermore, the invention provides methods for evaluating the efficacy of drugs, and monitoring the progress of patients, involved in clinical trials for the treatment of disorders as recited above.

The invention also provides methods for the identification of compounds that modulate (i.e., increase or decrease) the expression or activity of the polynucleotides and/or polypeptides of the invention. Such methods can be utilized, for example, for the identification of compounds that can enhance the therapeutic activity of the SCFA2, SCFA4 or SCFA4v polypeptides, and ameliorate symptoms of disorders as recited herein. Such methods can include, but are not limited to, assays for identifying compounds and other substances that interact with (e.g., bind to) the polypeptides of the invention.

The invention provides a method for identifying a compound that binds to the polypeptide of the present invention comprising contacting the compound with the polypeptide under conditions and for a time sufficient to form a polypeptide/compound complex and detecting the complex, so that if the polypeptide/compound complex is detected, a compound that binds to the polypeptide is identified.

Also provided is a method for identifying a compound that binds to the polypeptide comprising contacting the compound with the polypeptide in a cell for a time sufficient to form a polypeptide/compound complex wherein the complex drives expression of a reporter gene sequence in the cell and detecting the complex by detecting reporter gene sequence expression so that if the polypeptide/compound complex is detected a compound that binds to the polypeptide is identified.

Another embodiment of the invention provides gene therapy by delivery of SCFA2, SCFA4 or SCFA4v polypeptides for the treatment of conditions or disorders recited herein.

In a related embodiment, the invention is directed to use of a vector comprising a gene encoding a SCFA2, SCFA4 or SCFA4v polypeptide operably associated with an expression control sequence that provides for expression of the SCFA2, SCFA4 or SCFA4v polypeptide in the manufacture of a medicament for treating disorders as recited herein. More particularly, the invention provides for use of an adenoviral vector of the invention, e.g., as set out below, in the manufacture of a medicament for treating mucositis, inflammatory bowel disease or short bowel syndrome.

In addition to the foregoing methods and uses, the invention provides a virus vector comprising a gene encoding a SCFA2, SCFA4 or SCFA4v polypeptide operably associated with an expression control sequence. In a preferred embodiment, the virus vector is an adenovirus vector. The virus vectors of the invention can provide a gene encoding any of the SCFA2, SCFA4 or SCFA4v polypeptides, as set forth above.

The invention further provides a pharmaceutical composition comprising a virus vector of the invention and a pharmaceutically acceptable carrier.

Additional aspects and advantages of the invention will be apparent to those skilled in the art upon consideration of the following description, which details the practice of the invention.

3. BRIEF DESCRIPTION OF THE DRAWINGS

FIG. 1: Schematic representation of the SCFA2 (SEQ ID NO: 3), SCFA4 (SEQ ID NO: 14) and SCFA4v (SEQ ID NO: 23) polypeptides of the compositions of the invention. The length of the amino acid sequences includes the stop codon.

FIG. 2: ALIGN0 amino acid sequence alignment between SCFA4v (SEQ ID NO: 23) and a human protein similar to mouse thrombospondin type 1 domain protein R-spondin (SEQ ID NO: 48). The figure indicates that the two sequences share 69.2% identity over the entire length of the proteins. The letters represent amino acids as follows: A=Alanine, C=Cysteine, D=Aspartic Acid, E=Glutamic Acid, F=Phenylalanine, G=Glycine, H=Histidine, I=Isoleucine, K=Lysine, L=Leucine, M=Methionine, N=Asparagine, P=Proline, Q=Glutamine, R=Arginine, S=Serine, T=Threonine, V=Valine, W=Tryptophan, Y=Tyrosine. Gaps are presented as dashes.

FIG. 3: CLUSTALW alignment of SCFA2 (SEQ ID NO: 3), SCFA4 (SEQ ID NO: 14) and SCFA4v (SEQ ID NO: 23). The positions of the signal peptide, furin cleavage site, furin-like cysteine-rich domains, thrombospondin type 1 domain and nuclear localization signal are shown.

FIG. 4: H&E staining of cross-sections derived from the small intestine (SI) and colon (Co) derived from a control mouse (PBS), from a mouse treated with $1 \times 10^{10}$ viral particles of empty adenovirus (AdCV), from a mouse treated with adenovirus expressing SCFA2-V5His6 (AdhSCFA2; $1 \times 10^{10}$ viral particles), from a mouse treated with adenovirus expressing SCFA4-V5His6 (AdhSCFA4; $1 \times 10^{10}$ viral particles), and from a mouse treated with adenovirus expressing SCFA4v-V5His6 (AdhSCFA4v; $1 \times 10^{10}$ viral particles), as described in Example 5. The sections were obtained three days following injection of the empty or SCFA2, SCFA4 or SCFA4v adenovirus, respectively.

Figure 5:
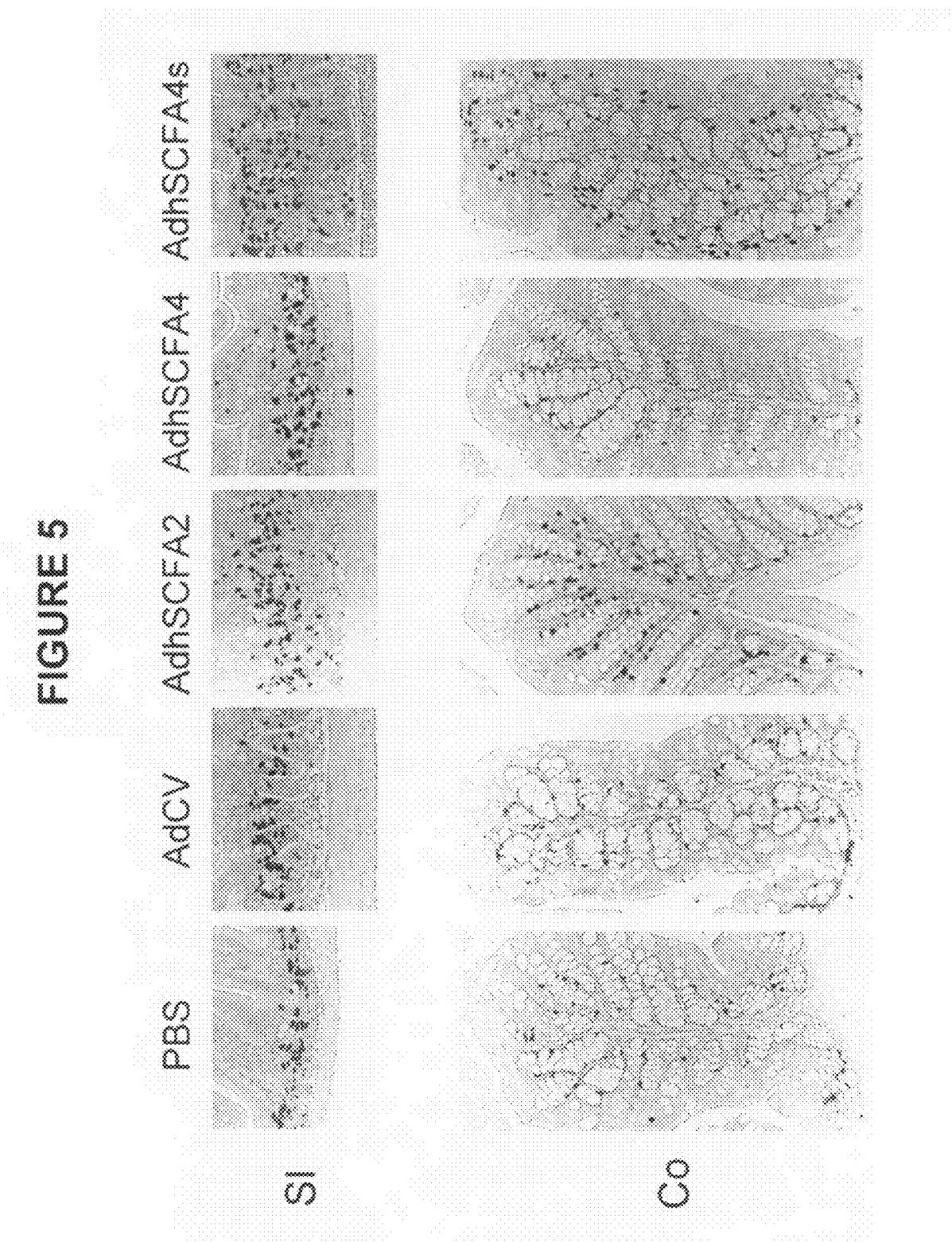

FIG. 5: Incorporation of BrdU into proliferating crypt cells of the small intestine (SI) and colon (Co) of mice that had received SCFA2, SCFA4 or SCFA4v adenovirus. The sections shown were obtained from the same mice for which the H&E staining is described in FIG. 4.

FIG. 6: Efficacy of SCFA2 (A) and SCFA2ΔC (B) on animal survival in 5-FU-induced mucositis in normal BDF-1 mice.

FIG. 7: Gross pathology of the intestinal tract of BDF-1 mice with 5-FU-induced mucositis treated with SCFA2 (A) and SCFA2ΔC (B).

FIG. 8: H&E staining of cross sections derived from the small intestine (SI) and colon (Co) of normal BDF-1 mice with 5-FU-induced mucositis treated with SCFA2 (A) or SCFA2ΔC (B).

FIG. 9: Efficacy of SCFA2 (A) and SCFA2ΔC (B) on villus height or crypt depth in 5-FU-induced mucositis in normal BDF-1 mice.

FIG. 10: Effect of SCFA2 (A) and SCFA2ΔC (B) on the crypt proliferative index in 5-FU-induced mucositis in normal BDF-1 mice.

FIG. 11: Incorporation of BrdU into the small intestine of normal BDF-1 mice with 5-FU-induced mucositis and treated with either SCFA2 (A) or SCFA2ΔC (B).

FIG. 12: Incorporation of BrdU into the colon of normal BDF-1 mice with 5-FU-induced mucositis and treated with SCFA2 (A) or SCFA2ΔC (B).

FIG. 13: H&E staining of and incorporation of BrdU into cross-sections derived from the tongue of normal BDF-1 mice with 5-FU-induced mucositis and treated with SCFA2 (A) or SCFA2ΔC (B).

FIG. 14: Effect of SCFA2 (A) or SCFA2ΔC (B) on the number of basal layer epithelial cells per mm of the ventral tongue of normal BDF-1 mice with 5-FU-induced mucositis.

FIG. 15: Effect of SCFA2 (A) or SCFA2ΔC (B) on mucosal thickness of the ventral tongue of normal BDF-1 mice with 5-FU-induced mucositis.

FIG. 16: Effect of SCFA2 (A) or SCFA2ΔC (B) on the basal layer BrdU proliferative index of ventral tongue of normal BDF-1 mice with 5-FU-induced mucositis.

4. DETAILED DESCRIPTION OF THE INVENTION

The polypeptides of the invention are depicted in FIG. 1, and are described in detail below.

The SCFA2 polypeptide of SEQ ID NO: 3 is an approximately 243-amino acid protein with a predicted molecular mass of approximately 27 kDa unglycosylated. The initial methionine starts at position 262 of SEQ ID NO: 2 and the putative stop codon begins at position 991 of SEQ ID NO: 2. Protein database searches with the BLAST algorithm (Altschul S. F. et al., J. Mol. Evol. 36:290-300 (1993) and Altschul S. F. et al., J. Mol. Biol. 21:403-10 (1990), herein incorporated by reference) indicate that SEQ ID NO: 3 is homologous to Xenopus laevis R-spondin2 (SEQ ID NO: 49) (accession numbers AAV31037.1; gi54145368)

A predicted approximately twenty-two amino acid residue signal peptide is encoded from approximately residue 1 to residue 22 of SEQ ID NO: 3. The extracellular portion is useful on its own. The signal peptide region was predicted using the Neural Network Signal P VI.I program (Nielsen et al., Int. J. Neural Syst. 8:581-599 (1997)), incorporated herein by reference) and/or using Neural Network SignalP V1.1 program (Nielsen et al, (1997) Int. J. Neural Syst. 8, 581-599). One of skill in the art will recognize that the actual cleavage site may be different than that predicted by the computer program. SEQ ID NO: 6 is the SCFA2 polypeptide of SEQ ID NO: 3 that lacks the signal peptide i.e SED ID NO: 6 is the dominant mature form of SCFA2 (SEQ ID NO: 3). SCFA2 contains a predicted furin protease cleavage site between amino acids 32 and 33 of SEQ ID NO: 3. Therefore, it is possible that two forms of SCFA2 exist: the dominant mature form (SEQ ID NO: 6), which lacks the signal peptide, and the mature form (SEQ ID NO: 8), which lacks the signal peptide and the amino acids residues between amino acid 33 and amino acid 38 of SEQ ID NO: 3. Deletion of the C-terminal 37 amino acids (residues 207 through 243 of SEQ ID NO: 3) yields increased secretion of SCFA2, herein denoted as SCFA2ΔC (SEQ ID NO: 51), without any change in biological activity (Kazanskaya et al. Dev. Cell 7:525-534 (2004)).

The SCFA4 polypeptide of SEQ ID NO: 14 is an approximately 234-amino acid protein with a predicted molecular mass of approximately 26 kDa unglycosylated. The initial methionine starts at position 101 of SEQ ID NO: 13 and the putative stop codon begins at position 803 of SEQ ID NO: 13. The variant of SCFA4, SCFA4v (SEQ ID NO: 23), is identical to SCFA4 but for the fact that SCFA4v lacks the TSP1 domain. SCFA4v is a protein of approximately 172 amino acid residues with a predicted molecular weight of approximately 19 kDa unglycosylated. The initial methionine starts at position 101 of SEQ ID NO: 23 and the putative stop codon begins at position 667 of SEQ ID NO: 23. Protein database searches with the BLAST algorithm (Altschul S. F. et al., J. Mol. Evol. 36:290-300 (1993) and Altschul S. F. et al., J. Mol. Biol. 21:403-10 (1990), herein incorporated by reference) indicate that SEQ ID NO: 14 is identical to dJ824F16.3, which is a novel human protein that is similar to mouse thrombospondin type 1 domain protein R-spondin (SEQ ID NO: 48) (accession numbers CAB65783.3; gi14627121). SCFA4v is also homologous to the human R-spondin protein of SEQ ID NO: 48, and it shares 69% identity with it (FIG. 2).

A predicted approximately twenty amino acid residue signal peptide is encoded from approximately residue 1 to residue 20 of SEQ ID NO: 14 and SEQ ID NO: 23. The signal peptide region was predicted using the Neural Network SignalP V1.1 program (Nielsen et al., Int. J. Neural Syst. 8:581-599 (1997)), incorporated herein by reference). One of skill in the art will recognize that the actual cleavage site may be different than that predicted by the computer program. SEQ ID NO: 17 is the SCFA4 polypeptide of SEQ ID NO: 14 that lacks the signal peptide, and SEQ ID NO: 26 is the SCFA4v polypeptide of SEQ ID NO: 23 that lacks the signal peptide. Unlike SCFA2, SCFA4 and SCFA4v do not contain a predicted furin protease cleavage (Zhou et al. J Biol Chem 274: 20745-20748 (1999). Therefore, it is possible that one form of SCFA4 and SCFA4v exist: the dominant mature form of SEQ ID NO: 17 and SEQ ID NO: 26, respectively.

Using the Pfam software program (Sonnhammer et al., Nucleic Acids Res., Vol. 26(1) pp. 320-322 (1998) herein incorporated by reference) the SCFA2, SCFA4 and SCFA4v polypeptides (SEQ ID NO: 3, 14 and 23, respectively) were examined for domains with homology to known peptide domains. SCFA2, SCFA4 and SCFA4v each contain 2 (two) furin-like domains. The furin-like domains of SCFA2 (SEQ ID NO: 10) are encoded by the polynucleotide of SEQ ID NO: 9, and the polypeptide domains span from amino acid 39 to 85, and from amino acid 91-132 of SEQ ID NO: 3. The two furin-like domains of SCFA4 and SCFA4v are identical. The domains, which are encompassed in SEQ ID NO: 19, are encoded by the polynucleotide of SEQ ID NO: 18. The first furin domain of SCFA4 and SCFA4v spans amino acids 34 to 79, and the second spans amino acids 85-126 of the respective full-length sequences. These furin-like domains have been found in a variety of eukaryotic proteins involved in signal transduction via receptor tyrosine kinases (Raz et al. Genetics 129:191-201 (1991)). Thus, the furin-like cysteine-rich domains of SCFA2, SCFA4, and SCFA4v may effect the proliferation of the intestinal epithelium.

SCFA2 and SCFA4 polypeptides of SEQ ID NO: 3 and 14, respectively, are expected to have a thrombospondin type 1 domain (TSP1) (SEQ ID NO: 12 and 21, respectively) encoded by the nucleotide sequence of SEQ ID NO: 11 and 20, respectively). The thrombospondin type 1 domain contained within SEQ ID NO: 3 is predicted to be from amino acid residue 147 to 203, and the TSP1 domain of SEQ ID NO: 14 is predicted to be from amino acid residue 141 to 195. SCFA4v lacks the TSP1 domain.

Thrombospondins are a family of extracellular matrix proteins that are involved in cell-cell and cell-matrix communication (Lawler et al., Curr. Opin. Cell Bio. 12:634-640 (2000)). More than five different thrombospondins are known with distinct patterns of tissue distribution. Some tissues like heart, cartilage, and brain express most of the thrombospondin gene products. Thrombospondin-1 is a major constituent of blood platelets. Thrombospondin-1 appears to function at the cell surface to bring together membrane proteins and cytokines and other soluble factors. Membrane proteins that bind thrombospondin-1 include integrins, integrin-associated protein (CD47), CD36, and proteoglycans. Transforming growth factor β (TGFβ) and platelet-derived growth factor also bind thrombospondin-1.

Thrombospondin-1 is a large protein with many distinct domains. It contains a globular domain at both amino and carboxy termini, a region of homology with procollagen, and three types of repeated sequence motifs termed thrombospondin (TSP) type 1, type 2, and type 3 repeats. The TSP1 repeat has been found in various different proteins including, complement components (C6, C7, C8A etc.) extracellular matrix proteins like ADAMTS, mindin, axonal guidance molecule like F-spondin semaphorins, and also SCO-spondin, and TRAP proteins of Plasmodium.

Thrombospondin type 1 repeats can activate TGFβ epithelial tissues which are involved in regulation of cell growth, differentiation, adhesion, migration, and death. TSP1 is further involved in protein binding, heparin binding, cell attachment, neurite outgrowth, inhibition of proliferation, inhibition of angiogenesis, and activation of apoptosis. TSP1 domains of Plasmodium circumsporozoite (CS) protein and TRAP proteins are implicated in salivary gland invasion by the sporozoite.

TSP1 sequences are characterized by conserved cysteines, closely spaced tryptophans, and a cluster of basic residues. Spatial configuration of TSP1 sequences shows two β-sheet domains which are shown to bind heparin (Kilpelainen et al (2000) J. Biol Chem. 275, 13564-13570, incorporated herein by reference). A similar spatial fold has been described for heparin-binding growth associated molecule (HB-GAM). HB-GAM is identical to mitogenic and neurite outgrowth-promoting protein pleitrophin; osteoblast specific factor-1; heparin-binding neurotrophic factor; and heparin affin regulatory peptide. Expression of HB-GAM was shown to be associated with extracellular matrix of axonal tracts and synapses, and also with basement membranes outside of brain and in the cartilage matrix. Recently, N-syndecan has been shown to be the receptor for HB-GAM in brain and has been suggested to play a role in regulation of hippocampal long-term potentiation, a form of brain plasticity implicated in memory and learning. Therefore, TSP1-containing proteins may act as growth promoters and may exhibit SCFA2, SCFA4 or SCFA4v activities.

In addition, thrombospondin, synthesized in bone marrow and deposited within the extracellular matrix, functions as a cytoadhesion molecule for primary pluripotent progenitor cells, as well as for hematopoietic progenitor cells committed to erythroid, granulocytic, and megakaryocytic lineages. Thus thrombospondins may be important in blood cell development (Long and Dixit (1990) Blood 75, 2311-2318, incorporated herein by reference).

SCFA2, SCFA4 or SCFA4v polypeptides and polynucleotides of the invention can be used to induce proliferation or differentiation of gastrointestinal crypt cells. They can also be used in the treatment of conditions where epithelialization is required, such as for the treatment of gastrointestinal disorders including chemotherapy and radiation therapy-induced mucositis, mucositis of the oropharynx, lips and esophagus, inflammatory bowel disease, and other conditions including wounds, burns, ophthalmic disorders, and any disorder where stimulation of epithelial cell proliferation or regeneration is desired. The polynucleotides and polypeptides of the invention can further be utilized to generate new tissues and organs that may aid patients in need of transplanted tissues.

4.1 Definitions

In describing the present invention the following terms will be employed and are intended to be defined as indicated below.

It must be noted that as used herein and in the appended claims, the singular forms "a", "an" and "the" include plural references unless the context clearly dictates otherwise.

In accordance with the present invention, the term "SCFA2, SCFA4 or SCFA4v protein(s)" or "SCFA2, SCFA4 or SCFA4v polypeptide(s) refers to the full-length protein defined by amino acids Met$^1$ to Ala$^{243}$ (SEQ ID NO: 3), Met$^1$ to Ala$^{234}$ (SEQ ID NO: 14), and Met$^1$ to Ala$^{172}$ fragments and analogs thereof.

The term "full-length SCFA2, SCFA4 or SCFA4v," wild type SCFA2, SCFA4 or SCFA4v", or "native SCFA2, SCFA4 or SCFA4v" as used herein all refer to the polypeptide that contains 243, 234, and 172 amino acid residues (SEQ ID NO: 3, 14, and 23, respectively).

The term "fragment" refers to a polypeptide derived from the native SCFA2, SCFA4 or SCFA4v that does not include the entire sequence of SCFA2, SCFA4 or SCFA4v. Such a fragment may be a truncated version of the full-length molecule, for example SEQ ID NO: 8 as well as an internally deleted polypeptide. A SCFA2, SCFA4 or SCFA4v fragment may have SCFA2, SCFA4 or SCFA4v bioactivity as determined by the effect SCFA2, SCFA4 or SCFA4v on the proliferation of epithelial cells in vitro and/or in vivo, as described herein.

The term "analog" refers to derivatives of the reference molecule. The analog may retain biological activity, as described above. In general, the term "analog" refers to compounds having a native polypeptide sequence and structure with one or more amino acid additions, substitutions (generally conservative in nature) and/or deletions, relative to the native molecule, so long as the modifications do not destroy activity. Preferably, the analog has at least the same biological activity as the parent molecule, and may even display enhanced activity over the parent molecule. Methods for making polypeptide analogs are known in the art. Particularly preferred analogs include substitutions that are conservative in nature, i.e., those substitutions that take place within a family of amino acids that are related in their side chains. Specifically, amino acids are generally divided into four families: (1) acidic: aspartate, glutamate; (2) basic: lysine, arginine, histidine; (3) non-polar: alanine, valine, leucine, isoleucine, proline, phenylalanine, methionine, tryptophan; and (4) uncharged polar: glycine, asparagine, glutamine, cysteine, serine, threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid will preserve the biological activity of SCFA2, SCFA4 or SCFA4v.

Guidance in determining which amino acid residues may be replaced, added or deleted without abolishing activities of interest, may be found by comparing the sequence of the particular polypeptide with that of homologous peptides and minimizing the number of amino acid sequence changes made in regions of high homology (conserved regions) or by replacing amino acids with consensus sequence.

Alternatively, recombinant analogs encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations in the polynucleotide sequence may be reflected in the polypeptide or domains of other peptides added to the polypeptide to modify the properties of any part of the polypeptide, to change characteristics such as ligand-binding affinities, interchain affinities, or degradation/turnover rate.

Preferably, amino acid "substitutions" are the result of replacing one amino acid with another amino acid having similar structural and/or chemical properties, i.e., conservative amino acid replacements. "Conservative" amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Insertions" or "deletions" are preferably in the range of about 1 to 20 amino acids, more preferably 1 to 10 amino acids. The variation allowed may be experimentally determined by systematically making insertions, deletions, or substitutions of amino acids in a polypeptide molecule using recombinant DNA techniques and assaying the resulting recombinant variants for activity.

Alternatively, where alteration of function is desired, insertions, deletions or non-conservative alterations can be engineered to produce altered polypeptides. Such alterations can, for example, alter one or more of the biological functions or biochemical characteristics of the polypeptides of the invention. For example, such alterations may change polypeptide characteristics such as ligand-binding affinities, interchain affinities, or degradation/turnover rate. Further, such alterations can be selected so as to generate polypeptides that are better suited for expression, scale up and the like in the host cells chosen for expression. For example, cysteine residues can be deleted or substituted with another amino acid residue in order to eliminate disulfide bridges.

The term "derivative" refers to polypeptides chemically modified by such techniques as ubiquitination, labeling (e.g., with radionuclides or various enzymes), covalent polymer attachment such as pegylation (derivatization with polyethylene glycol) and insertion or substitution by chemical synthesis of amino acids such as ornithine, which do not normally occur in human proteins.

The terms "polypeptide" and "protein" refer to a polymer of amino acid residues and are not limited to a minimum length of the product. The terms also include, unless otherwise indicated, modifications of the polypeptide that do not change the sequence of amino acids, for example, glycosylated, acetylated and phosphorylated forms. A polypeptide or protein, for purposes of the present invention, may be synthetically or recombinantly produced, as well as isolated from natural sources.

By "purified" and "isolated" is meant, when referring to a polypeptide or polynucleotide, that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type are present in the sample. In one embodiment, the polynucleotide or polypeptide is purified such that it constitutes at least 95% by weight of the indicated biological macromolecules present but water, buffers, and other small molecules, especially molecules having a molecular weight of less than 1000 daltons, can be present.

An "isolated polynucleotide which encodes a particular polypeptide" refers to a nucleic acid molecule which is substantially free of other nucleic acid molecules that do not encode the subject polypeptide; however, the molecule may include some additional bases or moieties which do not deleteriously affect the basic characteristics of the composition.

The term "naturally occurring polypeptide" refers to polypeptides produced by cells that have not been genetically engineered and specifically contemplates various polypeptides arising from post-translational modifications of the polypeptide including, but not limited to, acetylation, carboxylation, glycosylation, phosphorylation, lipidation and acylation.

The term "translated protein coding portion" means a sequence which encodes for the full length protein which may include any leader sequence or a processing sequence.

The term "dominant mature protein coding sequence" refers to a sequence which encodes a peptide or protein without any leader/signal sequence. The "dominant mature protein portion" refers to that portion of the protein without the leader/signal sequence. The "mature" form refers to a SCFA2 polypeptide that lacks the leader/signal sequence and the sequence to the furin cleavage site. The peptide may have the leader sequence and/or the furin cleavage site removed during processing in the cell or the protein may have been produced synthetically or using a polynucleotide only encoding for the mature protein coding sequence. It is contemplated that the mature or dominant mature protein portion may or may not include an initial methionine residue. The initial methionine is often removed during processing of the peptide.

The term "isolated" as used herein refers to a nucleic acid or polypeptide separated from at least one other component (e.g., nucleic acid or polypeptide) present with the nucleic acid or polypeptide in its natural source. In one embodiment, the nucleic acid or polypeptide is found in the presence of (if anything) only a solvent, buffer, ion, or other components normally present in a solution of the same. The terms "isolated" and "purified" do not encompass nucleic acids or polypeptides present in their natural source.

The term "recombinant," when used herein to refer to a polypeptide or protein, means that a polypeptide or protein is derived from recombinant (e.g., microbial, insect, or mammalian) expression systems. "Microbial" refers to recombinant polypeptides or proteins made in bacterial or fungal (e.g., yeast) expression systems. As a product, "recombinant microbial" defines a polypeptide or protein essentially free of native endogenous substances and unaccompanied by associated native glycosylation. Polypeptides or proteins expressed in most bacterial cultures, e.g., E. coli, will be free of glycosylation modifications; polypeptides or proteins expressed in yeast will have a glycosylation pattern in general different from those expressed in mammalian cells.

By a "recombinant polypeptide" is intended a polypeptide which has been prepared by recombinant DNA techniques as described herein. In general, the gene coding for the desired polypeptide is cloned and then expressed in transformed organisms, as described farther below. The host organism expresses the foreign gene to produce the polypeptide under expression conditions. Alternatively, the promoter controlling expression of an endogenous polypeptide can be altered to render a recombinant polypeptide.

The term "active" refers to those forms of the polypeptide that retain the biologic and/or immunologic activities of any naturally occurring polypeptide. According to the invention, the terms "biologically active" or "biological activity" refer to a protein or peptide-having structural, regulatory or biochemical functions of a naturally occurring molecule. Likewise "biologically active" or "biological activity" refers to the capability of the natural, recombinant or synthetic SCFA2, SCFA4 or SCFA4v peptide, or any peptide thereof, to induce a specific biological response in appropriate animals or cells and to bind with specific antibodies.

The term "secreted" includes a protein that is transported across or through a membrane, including transport as a result of signal sequences in its amino acid sequence when it is expressed in a suitable host cell. "Secreted" proteins include without limitation proteins secreted wholly (e.g., soluble proteins) or partially (e.g., receptors) from the cell in which they are expressed. "Secreted" proteins also include without limitation proteins that are transported across the membrane of the endoplasmic reticulum. "Secreted" proteins are also intended to include proteins containing non-typical signal sequences (e.g. Interleukin-1 Beta, see Krasney, P. A. and Young, P. R. (1992) Cytokine 4(2):134-143) and factors released from damaged cells (e.g. Interleukin-1 Receptor Antagonist, see Arend, W. P. et. al. (1998) Annu. Rev. Immunol. 16:27-55)

The term "polynucleotide" or "nucleic acid molecule" as used herein refers to a polymeric form of nucleotides of any length, either ribonucleotides or deoxyribonucleotides. This term refers only to the primary structure of the molecule and thus includes double- and single-stranded DNA and RNA. It also includes known types of modifications, for example, labels which are known in the art, methylation, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example proteins (including for e.g., nucleases, toxins, antibodies, signal peptides, poly-L-lysine, etc.), those with intercalators (e.g., acridine, psoralen, etc.), those containing chelates (e.g., metals, radioactive metals, boron, oxidative metals, etc.), those containing alkylators, those with modified linkages (e.g., alpha anomeric nucleic acids, etc.), as well as unmodified forms of the polynucleotide. Generally, nucleic acid segments provided by this invention may be assembled from fragments of the genome and short oligonucleotide linkers, or from a series of oligonucleotides, or from individual nucleotides, to provide a synthetic nucleic acid which is capable of being expressed in a recombinant transcriptional unit comprising regulatory elements derived from a microbial or viral operon, or a eukaryotic gene.

The terms "oligonucleotide fragment" or a "polynucleotide fragment", "portion," or "segment" or "probe" or "primer" are used interchangeably and refer to a sequence of nucleotide residues which are at least about 5 nucleotides, more preferably at least about 7 nucleotides, more preferably at least about 9 nucleotides, more preferably at least about 11 nucleotides and most preferably at least about 17 nucleotides. The fragment is preferably less than about 500 nucleotides, preferably less than about 200 nucleotides, more preferably less than about 100 nucleotides, more preferably less than about 50 nucleotides and most preferably less than 30 nucleotides. Preferably the probe is from about 6 nucleotides to about 200 nucleotides, preferably from about 15 to about 50 nucleotides, more preferably from about 17 to 30 nucleotides and most preferably from about 20 to 25 nucleotides. Preferably the fragments can be used in polymerase chain reaction (PCR), various hybridization procedures or microarray procedures to identify or amplify identical or related parts of mRNA or DNA molecules. A fragment or segment may uniquely identify each polynucleotide sequence of the present invention. Preferably the fragment comprises a sequence substantially similar to a portion of SEQ ID NO: 1, 2, 4, 5, 7, 9, 11, 13, 15, 16, 18, 20, 22, 24, 25, 35, 39, 43, 50, 52, 53, or 54.

Probes may, for example, be used to determine whether specific mRNA molecules are present in a cell or tissue or to isolate similar nucleic acid sequences from chromosomal DNA as described by Walsh et al. (Walsh, P. S. et al., 1992, PCR Methods Appl 1:241-250). They may be labeled by nick translation, Klenow fill-in reaction, PCR, or other methods well known in the art. Probes of the present invention, their preparation and/or labeling are elaborated in Sambrook, J. et al., 1989, Molecular Cloning: A Laboratory Manual, Cold Spring Harbor Laboratory, NY; or Ausubel, F. M. et al., 1989, Current Protocols in Molecular Biology, John Wiley & Sons, New York N.Y., both of which are incorporated herein by reference in their entirety.

The nucleic acid sequences of the present invention also include the sequence information from any of the nucleic acid sequences of SEQ ID NO: 1, 2, 4, 5, 7, 9, 11, 13, 15, 16, 18, 20, 22, 24, 25, 35, 39, 43, 50, 52, 53, or 54. The sequence information can be a segment of SEQ ID NO: 1, 2, 4, 5, 7, 9, 11, 13, 15, 16, 18, 20, 22, 24, 25, 35, 39, 43, 50, 52, 53, or 54 that uniquely identifies or represents the sequence information of SEQ ID NO: 1, 2, 4, 5, 7, 9, 11, 13, 15, 16, 18, 20, 22, 24, 25, 35, 39, 43, 50, 52, 53, or 54. One such segment can be a twenty-mer nucleic acid sequence because the probability that a twenty-mer is fully matched in the human genome is 1 in 300. In the human genome, there are three billion base pairs in one set of chromosomes. Because $4^{20}$ possible twenty-mers exist, there are 300 times more twenty-mers than there are base pairs in a set of human chromosomes. Using the same analysis, the probability for a seventeen-mer to be fully matched in the human genome is approximately 1 in 5. When these segments are used in arrays for expression studies, fifteen-mer segments can be used. The probability that the fifteen-mer is fully matched in the expressed sequences is also approximately one in five because expressed sequences comprise less than approximately 5% of the entire genome sequence.

Similarly, when using sequence information for detecting a single mismatch, a segment can be a twenty-five mer. The probability that the twenty-five mer would appear in a human genome with a single mismatch is calculated by multiplying the probability for a full match $(1 \div 4^{25})$ times the increased probability for mismatch at each nucleotide position ($3 \times 25$). The probability that an eighteen mer with a single mismatch can be detected in an array for expression studies is approximately one in five. The probability that a twenty-mer with a single mismatch can be detected in a human genome is approximately one in five.

The term "open reading frame (ORF)" means a series of nucleotide triplets coding for amino acids without any termination codons and is a sequence translatable into protein.

The terms "operably linked" or "operably associated" refer to functionally related nucleic acid sequences. For example, a promoter is operably associated or operably linked with a coding sequence if the promoter controls the transcription of the coding sequence. While operably linked nucleic acid sequences can be contiguous and in the same reading frame, certain genetic elements e.g. repressor genes are not contiguously linked to the coding sequence but still control transcription/translation of the coding sequence.

The terms "recombinant DNA molecule," or "recombinant polynucleotide" are used herein to refer to a polynucleotide of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature. Thus, the term encompasses "synthetically derived" nucleic acid molecules.

The terms "complementary" or "complementarity" refer to the natural binding of polynucleotides by base pairing. For example, the sequence 5'-AGT-3' binds to the complementary sequence 3'-TCA-5'. Complementarity between two single-stranded molecules may be "partial" such that only some of the nucleic acids bind or it may be "complete" such that total complementarity exists between the single stranded molecules. The degree of complementarity between the nucleic acid strands has significant effects on the efficiency and strength of the hybridization between the nucleic acid strands.

The term "stringent" is used to refer to conditions that are commonly understood in the art as stringent. Stringent conditions can include highly stringent conditions (i.e., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C.), and moderately stringent conditions (i.e., washing in 0.2×SSC/0.1% SDS at 42° C.). Other exemplary hybridization conditions are described herein in the examples.

In instances of hybridization of deoxyoligonucleotides, additional exemplary stringent hybridization conditions include washing in 6×SSC/0.05% sodium pyrophosphate at 37° C. (for 14-base oligonucleotides), 48° C. (for 17-base oligonucleotides), 55° C. (for 20-base oligonucleotides), and 60° C. (for 23-base oligonucleotides).

As used herein, "substantially equivalent" can refer both to nucleotide and amino acid sequences, for example a mutant sequence, that varies from a reference sequence by one or more substitutions, deletions, or additions, the net effect of which does not result in an adverse functional dissimilarity between the reference and subject sequences. Typically, such a substantially equivalent sequence varies from one of those listed herein by no more than about 35% (i.e., the number of individual residue substitutions, additions, and/or deletions in a substantially equivalent sequence, as compared to the corresponding reference sequence, divided by the total number of residues in the substantially equivalent sequence is about 0.35 or less). Such a sequence is said to have 65% sequence identity to the listed sequence. In one embodiment, a substantially equivalent, e.g., mutant, sequence of the invention varies from a listed sequence by no more than 30% (70% sequence identity); in a variation of this embodiment, by no more than 25% (75% sequence identity); and in a further variation of this embodiment, by no more than 20% (80% sequence identity) and in a further variation of this embodiment, by no more than 10% (90% sequence identity) and in a further variation of this embodiment, by no more that 5% (95% sequence identity). Substantially equivalent, e.g., mutant, amino acid sequences according to the invention preferably have at least 80% sequence identity with a listed amino acid sequence, more preferably at least 90% sequence identity. Substantially equivalent nucleotide sequence of the invention can have lower percent sequence identities, taking into account, for example, the redundancy or degeneracy of the genetic code. Preferably, nucleotide sequence has at least about 65% identity, more preferably at least about 75% identity, and most preferably at least about 95% identity. For the purposes of the present invention, sequences having substantially equivalent biological activity and substantially equivalent expression characteristics are considered substantially equivalent. For the purposes of determining equivalence, truncation of the mature sequence (e.g., via a mutation which creates a spurious stop codon) should be disregarded. Sequence identity may be determined, e.g., using the Jotun Hein method (Hein, J. (1990) Methods Enzymol. 183:626-645). Identity between sequences can also be determined by other methods known in the art, e.g. by varying hybridization conditions.

The term "vector" refers to a nucleic acid molecule capable of transporting another nucleic acid to which it has been linked. The term "expression vector" includes plasmids, cosmids or phages capable of synthesizing the SCFA2, SCFA4 or SCFA4v protein encoded by the respective recombinant gene carried by the vector. Preferred vectors are those capable of autonomous replication and expression of nucleic acids to which they are linked.

The term "transformation" means introducing DNA into a suitable host cell so that the DNA is replicable, either as an extrachromosomal element, or by chromosomal integration.

The term "transfection" refers to the taking up of an expression vector by a suitable host cell, whether or not any coding sequences are in fact expressed. The term "infection" refers to the introduction of nucleic acids into a suitable host cell by use of a virus or viral vector.

The term "transcriptional regulatory elements" and transcriptional regulatory sequences" are used interchangeably to refer to DNA sequences necessary for the expression of an operably linked coding sequence in a particular organism. The control sequences that are suitable for prokaryotes, for example, include a promoter, optionally an operator sequence, and a ribosome binding site. Eukaryotic cells are known to utilize promoters, enhancers, splicing signals and polyadenylation signals. These terms are intended to encompass all elements that promote or regulate transcription, including promoters, core elements required for basic interaction of RNA polymerase and transcription factors, upstream elements, enhancers, and response elements (Lewin, "Genes V" (Oxford University Press, Oxford) pages 847-873).

A coding sequence is "under the control" of transcriptional and translational control sequences in a cell when RNA polymerase transcribes the coding sequence into mRNA, which is then optionally trans-RNA spliced and translated into the protein encoded by the coding sequence.

The term "expression modulating fragment (EMF)" means a series of nucleotides that modulates the expression of an operably linked ORF or another EMF.

As used herein, a sequence is said to "modulate the expression of an operably linked sequence" when the expression of the sequence is altered by the presence of the EMF. EMFs include, but are not limited to, promoters, and promoter modulating sequences (inducible elements). One class of EMFs is nucleic acid fragments which induce the expression of an operably linked ORF in response to a specific regulatory factor or physiological event.

The term "recombinant expression vehicle or vector" refers to a plasmid or phage or virus or vector, for expressing a polypeptide from a DNA (RNA) sequence. An expression vehicle can comprise a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription initiation and termination sequences. Structural units intended for use in yeast or eukaryotic expression systems preferably include a leader sequence enabling extracellular secretion of translated protein by a host cell. Alternatively, where recombinant protein is expressed without a leader or transport sequence, it may include an amino terminal methionine residue. This residue may or may not be subsequently cleaved from the expressed recombinant protein to provide a final product.

The term "recombinant expression system" means host cells which have stably integrated a recombinant transcriptional unit into chromosomal DNA or carry the recombinant transcriptional unit extrachromosomally. Recombinant expression systems as defined herein will express heterologous polypeptides or proteins upon induction of the regulatory elements linked to the DNA segment or synthetic gene to be expressed. This term also means host cells which have stably integrated a recombinant genetic element or elements having a regulatory role in gene expression, for example, promoters or enhancers. Recombinant expression systems as defined herein will express polypeptides or proteins endogenous to the cell upon induction of the regulatory elements linked to the endogenous DNA segment or gene to be expressed. The cells can be prokaryotic or eukaryotic.

The term "pluripotent" refers to the capability of a cell to differentiate into a number of differentiated cell types that are present in an adult organism. A pluripotent cell is restricted in its differentiation capability in comparison to a totipotent cell.

The term "non-human mammal" refers to all members of the class Mammalia except humans. "Mammal" refers to any animal classified as a mammal, including humans, domestic and farm animals, and zoo, sports, or pet animals, such as a mouse, rat, rabbit, pig, sheep, goat, cattle and higher primates.

The terms "treat" or "treatment" refer to both therapeutic and prophylactic or preventative measures, wherein the object is to prevent or lessen an undesired physiological change or condition, such as chemotherapy or radiation therapy-induced mucositis. For the purposes of this invention, beneficial or desired clinical results include, but are not limited to alleviation of symptoms, diminishment of extent of the disease, stabilized state of the disease, whether detectable or undetectable.

A "disorder" is any condition that would benefit from treatment with a molecule identified using the transgenic animal model of the invention. This includes chronic and acute disorders or diseases including those pathological conditions which predispose the mammal to the disorder in question. Non-limiting examples of disorders to be treated herein include mucositis, inflammatory bowel disease and skin lesions. A preferred disorder to be treated in accordance with the present invention is mucositis.

"Inflammatory bowel disease (IBD)" herein refers to idiopathic or chronic inflammatory disease of either or both the small intestine and large bowel, and includes Crohn's disease, ulcerative colitis, IBD caused by infectious agents, and antibiotic associated IBD.

"Mucositis" herein refers to inflammation of the mucous membranes of the alimentary tract including the oropharynx and lips, esophagus, and large and small intestine.

"Short Bowel Syndrome" or "SBS" herein refers to a condition of nutritional malabsorption resulting from anatomical or functional loss of a significant length of the small intestine.

The terms "effective amount" or "pharmaceutically effective amount" refer to a nontoxic but sufficient amount of the agent to provide the desired biological result. That result can be reduction and/or alleviation of the signs, symptoms, or causes of a disease, or any other desired alteration of a biological system. For example, an effective amount of a SCFA2, SCFA4 or SCFA4v fragment for use with the present methods is an amount sufficient to stimulate epithelial cell stimulation or proliferation, and preferably an amount sufficient to cause increased regeneration of the gastrointestinal epithelium in a subject suffering from chemotherapy or radiation therapy-induced mucositis, inflammatory bowel disease, or other disorders where epithelial cell proliferation is desired. Such amounts are described below. An appropriate "effective" amount in any individual case may be determined by one of ordinary skill in the art using routine experimentation.

By "pharmaceutically acceptable" or "pharmacologically acceptable" is meant a material which is not biologically or otherwise undesirable, i.e., the material may be administered to an individual without causing any undesirable biological effects or interacting in a deleterious manner with any of the components of the composition in which it is contained.

By "physiological pH" or a "pH in the physiological range" is meant a pH in the range of approximately 7.0 to 8.0 inclusive. Preferred physiological pH is in the range of approximately 7.2 to 7.6 inclusive.

As used herein, the term "subject" encompasses mammals and non-mammals. Examples of mammals include, but are not limited to, any member of the Mammalia class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. The term does not denote a particular age or gender.

4.2 Compositions of the Invention

4.2.1 Nucleic Acid Compositions

The invention is based on the discovery that compositions comprising the epithelial cell growth factor polypeptide, SCFA2, SCFA4 or SCFA4v, and the polynucleotides encoding the SCFA2, SCFA4 or SCFA4v polypeptide stimulate the growth and proliferation of intestinal epithelial cells including crypt cells. Therefore, the use of these compositions for the diagnosis and treatment of conditions wherein stimulation of epithelial cell proliferation or regeneration is desired is contemplated. The isolated polynucleotides of the invention include, but are not limited to a polynucleotide comprising any of the nucleotide sequences of SEQ ID NO: 1, 2, 4, 5, 7, 9, 11, 13, 15, 16, 18, 20, 22, 24, 25, 35, 39, 43, 50, 52, 53, or 54; a polynucleotide comprising the full length protein coding sequence of SEQ ID NO: 2, 4, 13, 15, 22 or 24; (for example coding for SEQ ID NO: 3, 14, or 23); and a polynucleotide comprising the nucleotide sequence encoding the mature and dominant mature protein coding sequence of the polypeptide of SEQ ID NO: 5. The polynucleotides of the present invention also include, but are not limited to, a polynucleotide that hybridizes under stringent conditions to (a) the complement of any of the nucleotides sequences of SEQ ID NO: 1, 2, 4, 5, 7, 9, 11, 13, 15, 16, 18, 20, 22, 24, 25, 35, 39, 43, 50, 52, 53, or 54; (b) a polynucleotide encoding any one of the polypeptides of SEQ ID NO: 3, 6, 8, 10, 12, 14, 17, 19, 21, 23, 26, 36, 40, 44, 51, or 55; (c) a polynucleotide which is an allelic variant of any polynucleotides recited above; (d) a polynucleotide which encodes a species homolog of any of the proteins recited above; or (e) a polynucleotide that encodes a polypeptide comprising a specific domain or truncation of the polypeptides of SEQ ID NO3, 6, 8, 10, 12, 14, 17, 19, 21, 23, 26, 36, 40, or 44. Domains of interest include extracellular, transmembrane, or cytoplasmic domains, or combinations thereof; and catalytic and substrate binding domains.

The polynucleotides of the invention include naturally occurring or wholly or partially synthetic DNA, e.g., cDNA and genomic DNA, and RNA, e.g., mRNA. The polynucleotides may include all of the coding region of the cDNA or may represent a portion of the coding region of the cDNA.

The present invention also provides compositions comprising genes corresponding to the cDNA sequences disclosed herein. The corresponding genes can be isolated in accordance with known methods using the sequence information disclosed herein. Such methods include the preparation of probes or primers from the disclosed sequence information for identification and/or amplification of genes in appropriate genomic libraries or other sources of genomic materials. Further 5' and 3' sequence can be obtained using methods known in the art. For example, full length cDNA or genomic DNA that corresponds to any of the polynucleotide of SEQ ID NO: 2, 13 or 22 can be obtained by screening appropriate cDNA or genomic DNA libraries under suitable hybridization conditions using any of the polynucleotides of SEQ ID NO: 1, 2, 4, 5, 7, 9, 11, 13, 15, 16, 18, 20, 22, 24, 25, 35, 39, 43, 50, 52, 53, or 54 or a portion thereof as a probe. Alternatively, the polynucleotides of SEQ ID NO: 1, 2, 4, 5, 7, 9, 11, 13, 15, 16, 18, 20, 22, 24, 25, 35, 39, 43, 50, 52, 53, or 54 may be used as the basis for suitable primer(s) that allow identification and/or amplification of genes in appropriate genomic DNA or cDNA libraries.

The nucleic acid sequences of the invention can be assembled from ESTs and sequences (including cDNA and genomic sequences) obtained from one or more public databases, such as dbEST, gbpri, and UniGene. The EST sequences can provide identifying sequence information, representative fragment or segment information, or novel segment information for the full-length gene.

The polynucleotides of the invention also provide polynucleotides including nucleotide sequences that are substantially equivalent to the polynucleotides recited above. Polynucleotides according to the invention can have, e.g., at least about 65%, at least about 70%, at least about 75%, at least about 80%, 81%, 82%, 83%, 84%, 85%, 86%, 87%, 88%, or 89%, more typically at least about 90%, 91%, 92%, 93%, or 94% and even more typically at least about 95%, 96%, 97%, 98% or 99% sequence identity to a polynucleotide recited above.

Included within the scope of the nucleic acid sequences of the invention are nucleic acid sequence fragments that hybridize under stringent conditions to any of the nucleotide sequences of SEQ ID NO: 1, 2, 4, 5, 7, 9, 11, 13, 15, 16, 18, 20, 22, 24, 25, 35, 39, 43, 50, 52, 53, or 54, or complements thereof, which fragment is greater than about 5 nucleotides, preferably 7 nucleotides, more preferably greater than 9 nucleotides and most preferably greater than 17 nucleotides. Fragments of, e.g. 15, 17, or 20 nucleotides or more that are selective for (i.e. specifically hybridize to any one of the polynucleotides of the invention) are contemplated. Probes capable of specifically hybridizing to a polynucleotide can differentiate polynucleotide sequences of the invention from other polynucleotide sequences in the same family of genes or can differentiate human genes from genes of other species, and are preferably based on unique nucleotide sequences.

The sequences falling within the scope of the present invention are not limited to these specific sequences, but also include allelic and species variations thereof. Allelic and species variations can be routinely determined by comparing the sequence provided in SEQ ID NO: 1, 2, 4, 5, 7, 9, 11, 13, 15, 16, 18, 20, 22, 24, 25, 35, 39, 43, 50, 52, 53, or 54, a representative fragment thereof, or a nucleotide sequence at least 90% identical, preferably 95% identical, to SEQ ID NO: 1, 2, 4, 5, 7, 9, 11, 13, 15, 16, 18, 20, 22, 24, 25, 35, 39, 43, 50, 52, 53, or 54 with a sequence from another isolate of the same species. Furthermore, to accommodate codon variability, the invention includes nucleic acid molecules coding for the same amino acid sequences as do the specific ORFs disclosed herein. In other words, in the coding region of an ORF, substitution of one codon for another codon that encodes the same amino acid is expressly contemplated.

The nearest neighbor result for the nucleic acids of the present invention can be obtained by searching a database using an algorithm or a program. Preferably, a BLAST which stands for Basic Local Alignment Search Tool is used to search for local sequence alignments (Altshul, S. F. J Mol. Evol. 36 290-300 (1993) and Altschul S. F. et al. J. Mol. Biol. 21:403-410 (1990)).

Species homologs (or orthologs) of the disclosed polynucleotides and proteins are also provided by the present invention. Species homologs may be isolated and identified by making suitable probes or primers from the sequences provided herein and screening a suitable nucleic acid source from the desired species.

The invention also encompasses allelic variants of the disclosed polynucleotides or proteins; that is, naturally-occurring alternative forms of the isolated polynucleotide which also encodes proteins which are identical, homologous or related to that encoded by the polynucleotides.

The nucleic acid sequences of the invention are further directed to sequences which encode analogs of the described nucleic acids. These amino acid sequence analogs may be prepared by methods known in the art by introducing appropriate nucleotide changes into a native or variant polynucleotide. There are two variables in the construction of amino acid sequence variants: the location of the mutation and the nature of the mutation. Nucleic acids encoding the amino acid sequence analogs are preferably constructed by mutating the polynucleotide to encode an amino acid sequence that does not occur in nature. These nucleic acid alterations can be made at sites that differ in the nucleic acids from different species (variable positions) or in highly conserved regions (constant regions). Sites at such locations will typically be modified in series, e.g., by substituting first with conservative choices (e.g., hydrophobic amino acid to a different hydrophobic amino acid) and then with more distant choices (e.g., hydrophobic amino acid to a charged amino acid), and then deletions or insertions may be made at the target site. Amino acid sequence deletions generally range from about 1 to 30 residues, preferably about 1 to 10 residues, and are typically contiguous. Amino acid insertions include amino- and/or carboxyl-terminal fusions ranging in length from one to one hundred or more residues, as well as intrasequence insertions of single or multiple amino acid residues. Intrasequence insertions may range generally from about 1 to 10 amino residues, preferably from 1 to 5 residues. Examples of terminal insertions include the heterologous signal sequences necessary for secretion or for intracellular targeting in different host cells and sequences such as poly-histidine sequences useful for purifying the expressed protein.

In a preferred method, polynucleotides encoding the novel amino acid sequences are changed via site-directed mutagenesis. This method uses oligonucleotide sequences to alter a polynucleotide to encode the desired amino acid variant, as well as sufficient adjacent nucleotides on both sides of the changed amino acid to form a stable duplex on either side of the site being changed. In general, the techniques of site-directed mutagenesis are well known to those of skill in the art and this technique is exemplified by publications such as, Edelman et al., *DNA* 2:183 (1983). A versatile and efficient method for producing site-specific changes in a polynucleotide sequence was published by Zoller and Smith, *Nucleic Acids Res.* 10:6487-6500 (1982). PCR may also be used to create amino acid sequence variants of the novel nucleic acids. When small amounts of template DNA are used as starting material, primer(s) that differs slightly in sequence from the corresponding region in the template DNA can generate the desired amino acid variant. PCR amplification results in a population of product DNA fragments that differ from the polynucleotide template encoding the polypeptide at the position specified by the primer. The product DNA fragments replace the corresponding region in the plasmid and this gives a polynucleotide encoding the desired amino acid variant.

A further technique for generating amino acid variants is the cassette mutagenesis technique described in Wells et al., *Gene* 34:315 (1985); and other mutagenesis techniques well known in the art, such as, for example, the techniques in Sambrook et al., supra, and *Current Protocols in Molecular Biology*, Ausubel et al. Due to the inherent degeneracy of the genetic code, other DNA sequences which encode substantially the same or a functionally equivalent amino acid sequence may be used in the practice of the invention for the cloning and expression of these novel nucleic acids. Such DNA sequences include those which are capable of hybridizing to the appropriate novel nucleic acid sequence under stringent conditions.

Polynucleotides encoding preferred polypeptide truncations of the invention can be used to generate polynucleotides encoding chimeric or fusion proteins comprising one or more domains of the invention and heterologous protein sequences.

The polynucleotides of the invention additionally include the complement of any of the polynucleotides recited above. The polynucleotide can be DNA (genomic, cDNA, amplified, or synthetic) or RNA. Methods and algorithms for obtaining such polynucleotides are well known to those of skill in the art and can include, for example, methods for determining hybridization conditions that can routinely isolate polynucleotides of the desired sequence identities.

In accordance with the invention, polynucleotide sequences comprising the dominant mature or mature protein coding sequences, coding for any one of SEQ ID NO: 6, 8, 17 or 26, or functional equivalents thereof, may be used to generate recombinant DNA molecules that direct the expression of that nucleic acid, or a functional equivalent thereof, in appropriate host cells. Also included are the cDNA inserts of any of the clones identified herein.

A polynucleotide according to the invention can be joined to any of a variety of other nucleotide sequences by well-established recombinant DNA techniques (see Sambrook J et al. (1989) Molecular Cloning: A Laboratory Manual, Cold Spring Harbor Laboratory, NY). Useful nucleotide sequences for joining to polynucleotides include an assortment of vectors, e.g., plasmids, cosmids, lambda phage derivatives, phagemids, and the like, that are well known in the art. Accordingly, the invention also provides a vector including a polynucleotide of the invention and a host cell containing the polynucleotide. In general, the vector contains an origin of replication functional in at least one organism, convenient restriction endonuclease sites, and a selectable marker for the host cell. Vectors according to the invention include expression vectors, replication vectors, probe generation vectors, and sequencing vectors. A host cell according to the invention can be a prokaryotic or eukaryotic cell and can be a unicellular organism or part of a multicellular organism.

The present invention further provides recombinant constructs comprising a nucleic acid having any of the nucleotide sequences of SEQ ID NO: 1, 2, 4, 5, 7, 9, 11, 13, 15, 16, 18, 20, 22, 24, 25, 35, 39, 43, 50, 52, 53, or 54 or a fragment thereof or any other SCFA2, SCFA4 or SCFA4v polynucleotides. In one embodiment, the recombinant constructs of the present invention comprise a vector, such as a plasmid or viral vector, into which a nucleic acid having any of the nucleotide sequences of SEQ ID NO: 1, 2, 4, 5, 7, 9, 11, 13, 15, 16, 18, 20, 22, 24, 25, 35, 39, 43, 50, 52, 53, or 54 or a fragment thereof is inserted. In the case of a vector comprising one of the ORFs of the present invention, the vector may further comprise regulatory sequences, including for example, a promoter, operably linked to the ORF. Large numbers of suitable vectors and promoters are known to those of skill in the art and are commercially available for generating the recombinant constructs of the present invention. The following vectors are provided by way of example. Bacterial: pBs, phagescript, PsiX174, pBluescript SK, pBs KS, pNH8a, pNH16a, pNH18a, pNH46a (Stratagene); pTrc99A, pKK223-3, pKK233-3, pDR540, pRIT5 (Pharmacia). Eukaryotic: pWLneo, pSV2cat, pOG44, PXTI, pSG (Stratagene) pSVK3, pBPV, pMSG, and pSVL (Pharmacia).

The isolated polynucleotide of the invention may be operably linked to an expression control sequence such as the pMT2 or pED expression vectors disclosed in Kaufman et al., Nucleic Acids Res. 19, 4485-4490 (1991), in order to produce the protein recombinantly. Many suitable expression control sequences are known in the art. General methods of expressing recombinant proteins are also known and are exemplified in R. Kaufman, Methods in Enzymology 185, 537-566 (1990). As defined herein "operably linked" means that the isolated polynucleotide of the invention and an expression control sequence are situated within a vector or cell in such a way that the protein is expressed by a host cell which has been transformed (transfected) with the ligated polynucleotide/expression control sequence.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda PR, and trc. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. Generally, recombinant expression vectors will include origins of replication and selectable markers permitting transformation of the host cell, e.g., the ampicillin resistance gene of E. coil and S. cerevisiae TRP1 gene, and a promoter derived from a highly expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an amino terminal identification peptide imparting desired characteristics, e.g., stabilization or simplified purification of expressed recombinant product. Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM 1 (Promega Biotech, Madison, Wis., USA). These pBR322 "backbone" sections are combined with an appropriate promoter and the structural sequence to be expressed. Following transformation of a suitable host strain and growth of the host strain to an appropriate cell density, the selected promoter is induced or derepressed by appropriate means (e.g., temperature shift or chemical induction) and cells are cultured for an additional period. Cells are typically harvested by centrifugation, disrupted by physical or chemical means, and the resulting crude extract retained for further purification.

In addition to the use of expression vectors in the practice of the present invention, the present invention further includes novel expression vectors comprising promoter elements operatively linked to polynucleotide sequences encoding a protein of interest.

4.2.2 Hosts

The present invention further provides host cells genetically engineered with the vectors of this invention, which may be, for example, a cloning vector or an expression vector that contain the polynucleotides of the invention. For example, such host cells may contain nucleic acids of the invention introduced into the host cell using known transformation, transfection or infection methods. The vector may be, for example, in the form of a plasmid, a viral particle, a phage etc. The engineered host cells can be cultured in conventional nutrient media modified as appropriate for activating promoters, selecting transformants or amplifying SCFA2, SCFA4 or SCFA4v genes. The culture conditions, such as temperature, pH, and the like, are those previously used with the host cell selected for expression, and will be apparent to the ordinarily skilled artisan. The present invention still further provides host cells genetically engineered to express the polynucleotides of the invention, wherein such polynucleotides are in operative association with a regulatory sequence heterologous to the host cell which drives expression of the polynucleotides in the cell.

The host cell can be a higher eukaryotic host cell, such as a mammalian cell, a lower eukaryotic host cell, such as a yeast cell, or the host cell can be a prokaryotic cell, such as a bacterial cell. Introduction of the recombinant construct into the host cell can be effected by calcium phosphate transfection, DEAE, dextran mediated transfection, or electroporation (Davis, L. et al., Basic Methods in Molecular Biology (1986)). The host cells containing one of polynucleotides of the invention, can be used in conventional manners to produce the gene product encoded by the isolated fragment (in the case of an ORF) or can be used to produce a heterologous protein under the control of the EMF.

Any host/vector system can be used to express one or more of the SCFA2, SCFA4 or SCFA4v polypeptides. These include, but are not limited to, eukaryotic hosts such as HeLa cells, Cv-1 cell, COS cells, and Sf9 cells, as well as prokaryotic host such as E. coli and B. subtilis. The most preferred cells are those which do not normally express the particular polypeptide or protein or which expresses the polypeptide or protein at low natural level. Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., in Molecular Cloning: A Laboratory Manual, Second Edition, Cold Spring Harbor, N.Y. (1989), the disclosure of which is hereby incorporated by reference.

Various mammalian cell culture systems can be employed to express recombinant protein. Examples of mammalian expression systems include the COS-7 lines of monkey kidney fibroblasts, described by Gluzman, Cell 23:175 (1981), and other cell lines capable of expressing a compatible vector, for example, the C127, 3T3, CHO, HeLa and BHK cell tines. Mammalian expression vectors will comprise an origin of replication, a suitable promoter, and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements. Recombinant polypeptides and proteins produced in bacterial culture are usually isolated by initial extraction from cell pellets, followed by one or more salting-out, aqueous ion exchange or size exclusion chromatography steps. Protein refolding steps can be used, as necessary, in completing configuration of the mature protein. Finally, high performance liquid chromatography (HPLC) can be employed for final purification steps. Microbial cells employed in expression of proteins can be disrupted by any convenient method, including freeze-thaw cycling, sonication, mechanical disruption, or use of cell lysing agents.

A number of types of cells may act as suitable host cells for expression of the protein. Mammalian host cells include, for example, monkey COS cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells. Preferably, SCFA2, SCFA4 or SCFA4v proteins are expressed in Chinese Hamster Ovary (CHO) cells, and human embryonic kidney 293 (HEK293) cells.

Alternatively, it may be possible to produce the protein in lower eukaryotes such as yeast or in prokaryotes such as bacteria. Potentially suitable yeast strains include *Saccharomyces cerevisiae, Schizosaccharomyces pombe, Kluyveromyces* strains, *Candida, Pichia pastoris* or any yeast strain capable of expressing heterologous proteins. Potentially suitable bacterial strains include *Escherichia coli, Bacillus subtilis, Salmonella typhimurium*, or any bacterial strain capable of expressing heterologous proteins. If the protein is made in yeast or bacteria, it may be necessary to modify the protein produced therein, for example by phosphorylation or glycosylation of the appropriate sites, in order to obtain the functional protein. Such covalent attachments may be accomplished using known chemical or enzymatic methods.

4.2.3 Chimeric and Fusion Proteins

The invention also provides SCFA2, SCFA4 or SCFA4v chimeric or fusion proteins. As used herein, a SCFA2, SCFA4 or SCFA4v "chimeric protein" or "fusion protein" comprises a SCFA2, SCFA4 or SCFA4v polypeptide operatively-linked to a non-SCFA2, SCFA4 or SCFA4v polypeptide. A "SCFA2, SCFA4 or SCFA4v polypeptide" refers to a polypeptide having an amino acid sequence corresponding to a SCFA2, SCFA4 or SCFA4v protein, whereas a "non-SCFA2, SCFA4 or SCFA4v polypeptide" refers to a polypeptide having an amino acid sequence corresponding to a protein that is not substantially homologous to the SCFA2, SCFA4 or SCFA4v protein, e.g., a protein that is different from the SCFA2, SCFA4 or SCFA4v protein and that is derived from the same or a different organism. Within a SCFA2, SCFA4 or SCFA4v fusion protein the SCFA2, SCFA4 or SCFA4v polypeptide can correspond to all or a portion of a SCFA2, SCFA4 or SCFA4v protein. In one embodiment, a SCFA2, SCFA4 or SCFA4v fusion protein comprises at least one biologically active portion of a SCFA2, SCFA4 or SCFA4v protein. In another embodiment, a SCFA2, SCFA4 or SCFA4v fusion protein comprises at least two biologically active portions of a SCFA2, SCFA4 or SCFA4v protein. In yet another embodiment, a SCFA2, SCFA4 or SCFA4v fusion protein comprises at least three biologically active portions of a SCFA2, SCFA4 or SCFA4v protein. Within the fusion protein, the term "operatively-linked" is intended to indicate that the SCFA2, SCFA4 or SCFA4v polypeptide and the non-SCFA2, SCFA4 or SCFA4v polypeptide are fused in-frame with one another. The non-SCFA2, SCFA4 or SCFA4v polypeptide can be fused to the N-terminus or C-terminus of the SCFA2, SCFA4 or SCFA4v polypeptide.

In one embodiment, the fusion protein is a GST SCFA2, SCFA4 or SCFA4v fusion protein in which the SCFA2, SCFA4 or SCFA4v sequences are fused to the C-terminus of the GST (glutathione S-transferase) sequences. Such fusion proteins can facilitate the purification of recombinant SCFA2, SCFA4 or SCFA4v polypeptides. Preferably, the SCFA2, SCFA4 or SCFA4v polypeptide is fused with a V5-His tag for easy detection with an anti-V5 antibody and for rapid purification as described in the examples. SEQ ID NO: 36, 40, 44, and 55 which are encoded by the polynucleotides of SEQ ID NO: 35, 39, 43, and 54, respectively, represent SCFA2, SCFA2ΔC, SCFA4 and SCFA4v fusion proteins that have a V5-His6 tag.

In another embodiment, the fusion protein is a SCFA2, SCFA4 or SCFA4v protein containing a heterologous signal sequence at its N-terminus. In certain host cells (e.g., mammalian host cells), expression and/or secretion of SCFA2, SCFA4 or SCFA4v can be increased through use of a heterologous signal sequence. For example the signal sequence of SCFA2, SCFA4 or SCFA4v can be replaced with the signal sequence from the VJ2-C region of the mouse IgKappa (Igκ) chain. For example SEQ ID NO: 36, 40, 44, and 55 which are encoded by the polynucleotides of SEQ ID NO: 35, 39, 43, and 54, respectively, contain an Igκ signal sequence. The polynucleotides of SEQ ID NO: 35, 39, 43, and 54, which encode the fusion proteins of SEQ ID NO: 36, 40, 44, and 55 were used as described in the examples to express SCFA2, SCFA2ΔC, SCFA4 and SCFA4v in vivo and determine the biological activity of the polypeptides. A SCFA2, SCFA2ΔC, SCFA4 or SCFA4v chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, e.g., Ausubel, et al. (eds.) CURRENT PROTOCOLS IN MOLECULAR BIOLOGY, John Wiley & Sons, 1992). Moreover, many expression vectors are commercially available that already encode a fusion moiety (e.g., a GST polypeptide). A SCFA2, SCFA4 or SCFA4v-encoding nucleic acid can be cloned into such an expression vector such that the fusion moiety is linked in-frame to SCFA2, SCFA4 or SCFA4v protein.

4.2.4 Polypeptide Compositions

The pharmaceutical compositions of the invention comprise isolated SCFA2, SCFA4 or SCFA4v polypeptides that include, but are not limited to, a polypeptide comprising: the amino acid sequence set forth as any one of SEQ ID NO: 3, 6, 8, 10, 12, 14, 17, 19, 21, 23, 26, 36, 40, 44, 51, or 55, or an amino acid sequence encoded by any one of the nucleotide sequences SEQ ID NO: 1, 2, 4, 5, 7, 9, 11, 13, 15, 16, 18, 20, 22, 24, 25, 35, 39, 43, 50, 52, 53, or 54. Polypeptides of the invention also include polypeptides preferably with biological or immunological activity that are encoded by: (a) a polynucleotide having any one of the nucleotide sequences set forth in SEQ ID NO: 1, 2, 4, 5, 7, 9, 11, 13, 15, 16, 18, 20, 22, 24, 25, 35, 39, 43, 50, 52, 53, or 54; or (b) polynucleotides encoding any one of the amino acid sequences set forth as SEQ ID NO: 3, 6, 8, 10, 12, 14, 17, 19, 21, 23, 26, 36, 40, 44, 51, or 55 or (c) polynucleotides that hybridize to the complement of the polynucleotides of either (a) or (b) under stringent hybridization conditions. The invention also provides biologically active or immunologically active variants of any of the amino acid sequences set forth as SEQ ID NO: 3, 6, 8, 10, 12, 14, 17, 19, 21, 23, 26, 36, 40, 44, 51, or 55; and "substantial equivalents" thereof (e.g., with at least about 65%, at least about 70%, at least about 75%, at least about 80%, 81%, 82%, 83%, 84%, 85%, 86%, 87%, 88%, or 89%, more typically at least about 90%, 91%, 92%, 93%, or 94% and even more typically at least about 95%, 96%, 97%, 98% or 99%, most typically at least about 99% amino acid identity) that retain biological activity. Polypeptides encoded by allelic variants may have a similar, increased, or decreased activity compared to polypeptides comprising SEQ ID NO: 3, 6, 8, 10, 12, 14, 17, 19, 21, 23, 26, 36, 40, 44, 51, or 55.

Fragments of the proteins of the present invention which are capable of exhibiting biological activity are also encompassed by the present invention. Fragments of the protein may be in linear form or they may be cyclized using known methods, for example, as described in H. U. Saragovi, et al., Bio/Technology 10, 773-778 (1992) and in R. S. McDowell, et al., J. Amer. Chem. Soc. 114, 9245-9253 (1992), both of which are incorporated herein by reference. Such fragments may be fused to carrier molecules such as immunoglobulins for many purposes, including increasing the valency of protein binding sites.

The present invention also provides both full-length and dominant mature forms (for example, without a signal sequence or precursor sequence) or mature forms (for example, lacking the signal sequence and the furin cleavage site) of the disclosed proteins. The protein coding sequence is identified in the sequence listing by translation of the disclosed nucleotide sequences. The mature form of such protein may be obtained by expression of a full-length polynucleotide in a suitable mammalian cell or other host cell. The sequence of the mature form of the protein is also determinable from the amino acid sequence of the full-length form.

Protein compositions of the present invention may further comprise an acceptable carrier, such as a hydrophilic, e.g., pharmaceutically acceptable, carrier.

The present invention further provides isolated polypeptides encoded by the nucleic acid fragments of the present invention or by degenerate variants of the nucleic acid fragments of the present invention. By "degenerate variant" is intended nucleotide fragments which differ from a nucleic acid fragment of the present invention (e.g., an ORF) by nucleotide sequence but, due to the degeneracy of the genetic code, encode an identical polypeptide sequence. Preferred nucleic acid fragments of the present invention are the ORFs that encode proteins.

A variety of methodologies known in the art can be utilized to obtain any one of the isolated polypeptides or proteins of the present invention. At the simplest level, the amino acid sequence can be synthesized using commercially available peptide synthesizers. The synthetically-constructed protein sequences, by virtue of sharing primary, secondary or tertiary structural and/or conformational characteristics with proteins may possess biological properties in common therewith, including protein activity. This technique is particularly useful in producing small peptides and fragments of larger polypeptides. Fragments are useful, for example, in generating antibodies against the native polypeptide. Thus, they may be employed as biologically active or immunological substitutes for natural, purified proteins in screening of therapeutic compounds and in immunological processes for the development of antibodies.

The polypeptides and proteins of the present invention can alternatively be purified from cells which have been altered to express the desired polypeptide or protein. As used herein, a cell is said to be altered to express a desired polypeptide or protein when the cell, through genetic manipulation, is made to produce a polypeptide or protein which it normally does not produce or which the cell normally produces at a lower level. One skilled in the art can readily adapt procedures for introducing and expressing either recombinant or synthetic sequences into eukaryotic or prokaryotic cells in order to generate a cell which produces one of the polypeptides or proteins of the present invention.

The invention also relates to methods for producing a polypeptide comprising growing a culture of host cells of the invention in a suitable culture medium, and purifying the protein from the cells or the culture in which the cells are grown. For example, the methods of the invention include a process for producing a polypeptide in which a host cell containing a suitable expression vector that includes a polynucleotide of the invention is cultured under conditions that allow expression of the encoded polypeptide. The polypeptide can be recovered from the culture, conveniently from the culture medium, or from a lysate prepared from the host cells and further purified. Preferred embodiments include those in which the protein produced by such process is a full length or mature form of the protein.

In an alternative method, the polypeptide or protein is purified from bacterial cells which are transformed with SCFA2, SCFA4 or SCFA4v-encoding DNA to produce the polypeptide or protein. One skilled in the art can readily follow known methods for isolating polypeptides and proteins in order to obtain one of the isolated polypeptides or proteins of the present invention. These include, but are not limited to, immunochromatography, HPLC, size-exclusion chromatography, ion-exchange chromatography, and immuno-affinity chromatography. See, e.g., Scopes, *Protein Purification: Principles and Practice*, Springer-Verlag (1994); Sambrook, et al., in Molecular Cloning: *A Laboratory Manual*; Ausubel et al., *Current Protocols in Molecular Biology*. Polypeptide fragments that retain biological/immunological activity include fragments comprising greater than about 100 amino acids, or greater than about 200 amino acids, and fragments that encode specific protein domains.

The purified polypeptides can be used in in vitro binding assays which are well known in the art to identify molecules which bind to the polypeptides. These molecules include but are not limited to, for e.g., small molecules, molecules from combinatorial libraries, antibodies or other proteins. The molecules identified in the binding assay are then tested for antagonist or agonist activity in in vivo tissue culture or animal models that are well known in the art. In brief, the molecules are titrated into a plurality of cell cultures or animals and then tested for either cell/animal death or prolonged survival of the animal/cells.

The protein of the invention may also be expressed as a product of transgenic animals, e.g., as a component of the milk of transgenic cows, goats, pigs, or sheep which are characterized by somatic or germ cells containing a nucleotide sequence encoding the protein.

The proteins provided herein also include proteins characterized by amino acid sequences similar to those of purified proteins but into which modification are naturally provided or deliberately engineered. For example, modifications, in the peptide or DNA sequence, can be made by those skilled in the art using known techniques. Modifications of interest in the protein sequences may include the alteration, substitution, replacement, insertion or deletion of a selected amino acid residue in the coding sequence. For example, one or more of the cysteine residues may be deleted or replaced with another amino acid to alter the conformation of the molecule. Techniques for such alteration, substitution, replacement, insertion or deletion are well known to those skilled in the art (see, e.g., U.S. Pat. No. 4,518,584). Preferably, such alteration, substitution, replacement, insertion or deletion retains the desired activity of the protein. Regions of the protein that are important for the protein function can be determined by various methods known in the art including the alanine-scanning method which involved systematic substitution of single or strings of amino acids with alanine, followed by testing the resulting alanine-containing variant for biological activity. This type of analysis determines the importance of the substituted amino acid(s) in biological activity. Regions of the protein that are important for protein function may be determined by the eMATRIX program.

Other fragments and derivatives of the sequences of proteins which would be expected to retain protein activity in whole or in part and are useful for screening or other immunological methodologies may also be easily made by those skilled in the art given the disclosures herein. Such modifications are encompassed by the present invention.

The protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBat™ kit), and such methods are well known in the art, as described in Summers and Smith, Texas Agricultural Experiment Station Bulletin No. 1555 (1987), incorporated herein by reference. As used herein, an insect cell capable of expressing a polynucleotide of the present invention is "transformed."

The protein of the invention may be prepared by culturing transformed host cells under culture conditions suitable to express the recombinant protein. The resulting expressed protein may then be purified from such culture (i.e., from culture medium or cell extracts) using known purification processes, such as gel filtration and ion exchange chromatography. The purification of the protein may also include an affinity column containing agents which will bind to the protein; one or more column steps over such affinity resins as concanavalin A-agarose, Heparin-Toyopearl™ or Cibacrom blue 3GA Sepharose™; one or more steps involving hydrophobic interaction chromatography using such resins as phenyl ether, butyl ether, or propyl ether; or immunoaffinity chromatography.

Alternatively, the protein of the invention may also be expressed in a form which will facilitate purification. For example, it may be expressed as a fusion protein, such as those of maltose binding protein (MBP), glutathione-S-transferase (GST) or thioredoxin (TRX), or as a His tag. Kits for expression and purification of such fusion proteins are commercially available from New England BioLab (Beverly, Mass.), Pharmacia (Piscataway, N.J.) and Invitrogen, respectively. The protein can also be tagged with an epitope and subsequently purified by using a specific antibody directed to such epitope. One such epitope ("FLAG®") is commercially available from Kodak (New Haven, Conn.).

Finally, one or more reverse-phase high performance liquid chromatography (RP-HPLC) steps employing hydrophobic RP-HPLC media, e.g., silica gel having pendant methyl or other aliphatic groups, can be employed to further purify the protein. Some or all of the foregoing purification steps, in various combinations, can also be employed to provide a substantially homogeneous isolated recombinant protein. The protein thus purified is substantially free of other mammalian proteins and is defined in accordance with the present invention as an "isolated protein."

The polypeptides of the invention include SCFA2, SCFA4 or SCFA4v analogs. This embraces fragments of SCFA2, SCFA4 or SCFA4v polypeptide, as well as SCFA2, SCFA4 or SCFA4v polypeptides which comprise one or more amino acids deleted, inserted, or substituted. Also, analogs of the SCFA2, SCFA4 or SCFA4v polypeptide of the invention embrace fusions of the SCFA2, SCFA4 or SCFA4v polypeptides or modifications of the SCFA2, SCFA4 or SCFA4v polypeptides, wherein the SCFA2, SCFA4 or SCFA4v polypeptide or analog is fused to another moiety or moieties, e.g., targeting moiety or another therapeutic agent. Such analogs may exhibit improved properties such as activity and/or stability. Examples of moieties which may be fused to the SCFA2, SCFA4 or SCFA4v polypeptide or an analog include, for example, targeting moieties which provide for the delivery of polypeptide to the small intestine, e.g., antibodies to the small intestine, or antibodies to receptor and ligands expressed on gastroinetestinal cells. Other moieties which may be fused to SCFA2, SCFA4 or SCFA4v polypeptide include therapeutic agents which are used for treatment, for example cytokines or other medications, of gastrointestinal disorders, and other conditions as recited herein.

4.2.5 Gene Therapy

The invention provides gene therapy to treat the diseases cited herein. Delivery of a functional gene encoding polypeptides of the invention to appropriate cells is effected ex vivo, in situ, or in vivo by use of vectors, and more particularly viral vectors (e.g., adenovirus, adeno-associated virus, or a retrovirus), or ex vivo by use of physical DNA transfer methods (e.g., liposomes or chemical treatments). See, for example, Anderson, Nature, supplement to vol. 392, no. 6679, pp. 25-20 (1998). For additional reviews of gene therapy technology see Friedmann, Science, 244: 1275-1281 (1989); Verma, Scientific American: 68-84 (1990); and Miller, Nature, 357: 455-460 (1992).

As discussed above, a "vector" is any means for the transfer of a nucleic acid according to the invention into a host cell. Preferred vectors are viral vectors, such as retroviruses, herpes viruses, adenoviruses and adeno-associated viruses. Thus, a gene or nucleic acid sequence encoding a SCFA2, SCFA4 or SCFA4v protein or polypeptide domain fragment thereof is introduced in vivo, ex vivo, or in vitro using a viral vector or through direct introduction of DNA. Expression in targeted tissues can be effected by targeting the transgenic vector to specific cells, such as with a viral vector or a receptor ligand, or by using a tissue-specific promoter, or both.

Viral vectors commonly used for in vivo or ex vivo targeting and therapy procedures are DNA-based vectors and retroviral vectors. Methods for constructing and using viral vectors are known in the art [see, e.g., Miller and Rosman, BioTechniques 7:980-990 (1992)]. Preferably, the viral vectors are replication defective, that is, they are unable to replicate autonomously in the target cell. In general, the genome of the replication defective viral vectors which are used within the scope of the present invention lack at least one region which is necessary for the replication of the virus in the infected cell. These regions can either be eliminated (in whole or in part), be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (on the isolated DNA) or in situ, using the techniques of genetic manipulation or by treatment with mutagenic agents. Preferably, the replication defective virus retains the sequences of its genome which are necessary for encapsulating the viral particles.

DNA viral vectors include an attenuated or defective DNA virus, such as but not limited to herpes simplex virus (HSV), papillomavirus, Epstein-Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector [Kaplitt et al., Molec. Cell. Neurosci. 2:320-330 (1991)], defective herpes virus vector lacking a glycoprotein L gene [Patent Publication RD 371005 A], or other defective herpes virus vectors [International Patent Publication No. WO 94/21807, published Sep. 29, 1994; International Patent Publication No. WO 92/05263, published Apr. 2, 1994]; an attenuated adenovirus vector, such as the vector described by Stratford-Perricaudet et al. [J. Clin. Invest. 90:626-630 (1992); see also La Salle et al., Science 259:988-990 (1993)]; and a defective adeno-associated virus vector [Samulski et al., J. Virol. 61:3096-3101 (1987); Samulski et al., J. Virol. 63:3822-3828 (1989); Lebkowski et al., Mol. Cell. Biol. 8:3988-3996 (1988)].

Preferably, for in vivo administration, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-γ (IFN-γ), or anti-CD4 antibody, can be administered to block humoral or cellular immune responses to the viral vectors [see, e.g., Wilson, Nature Medicine (1995)]. In addition, it is advantageous to employ a viral vector that is engineered to express a minimal number of antigens.

In a preferred embodiment, the vector is an adenovirus vector. As shown in the Examples, the adenovirus vector has shown itself to be particularly effective for delivery of the SCFA2, SCFA4 or SCFA4v polypeptide, as shown by the unexpectedly efficient effects of stimulating intestinal epithelial cell proliferation resulting in marked, diffuse thickening of the mucosa by crypt epithelial hyperplasia and a marked increase in crypt length and complex branching. Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to using type 2 or type 5 human adenoviruses (Ad 2 or Ad 5) or adenoviruses of animal origin (see WO94/26914). Those adenoviruses of animal origin which can be used within the scope of the present invention include adenoviruses of canine, bovine, murine (example: Mav1, Beard et al., Virology 75 (1990) 81), ovine, porcine, avian, and simian (example: SAV) origin.

Preferably, the replication defective adenoviral vectors of the invention comprise the inverted terminal repeats (ITRs), an encapsidation sequence and the nucleic acid of interest. Still more preferably, at least the E1 region of the adenoviral vector is non-functional. Other regions may also be modified, in particular the E3 region (WO95/02697), the E2 region (WO94/28938), the E4 region (WO94/28152, WO94/12649 and WO95/02697), or in any of the late genes L1-L5.

In a preferred embodiment, the adenoviral vector has a deletion in the E1 and E3 region. Examples of E1-deleted adenoviruses are disclosed in EP 185,573, the contents of which are incorporated herein by reference.

The replication defective recombinant adenoviruses according to the invention can be prepared by any technique known to the person skilled in the art (Levrero et al., Gene 101 (1991) 195, EP 185 573; Graham, EMBO J. 3 (1984) 2917). In particular, they can be prepared by homologous recombination between an adenovirus and a plasmid which carries, inter alia, the DNA sequence of interest. The homologous recombination is effected following cotransfection of the said adenovirus and plasmid into an appropriate cell line. The cell line which is employed should preferably (i) be transformable by the said elements, and (ii) contain the sequences which are able to complement the part of the genome of the replication defective adenovirus, preferably in integrated form in order to avoid the risks of recombination. Examples of cell lines which may be used are the human embryonic kidney cell line 293 (Graham et al., J. Gen. Virol. 36 (1977) 59) which contains the left-hand portion of the genome of an Ad5 adenovirus (12%) integrated into its genome, and cell lines which are able to complement the E1 and E4 functions, as described in applications WO94/26914 and WO95/02697. Recombinant adenoviruses are recovered and purified using standard molecular biological techniques, which are well known to one of ordinary skill in the art.

Promoters that may be used in the present invention include both constitutive promoters and regulated (inducible) promoters. The promoter may be naturally responsible for the expression of the nucleic acid. It may also be from a heterologous source. In particular, it may be promoter sequences of eukaryotic or viral genes. For example, it may be promoter sequences derived from the genome of the cell which it is desired to infect. Likewise, it may be promoter sequences derived from the genome of a virus, including the adenovirus used. In this regard, there may be mentioned, for example, the promoters of the E1A, MLP, CMV and RSV genes and the like.

In addition, the promoter may be modified by addition of activating or regulatory sequences or sequences allowing a tissue-specific or predominant expression (enolase and GFAP promoters and the like). Moreover, when the nucleic acid does not contain promoter sequences, it may be inserted, such as into the virus genome downstream of such a sequence.

Some promoters useful for practice of this invention are ubiquitous promoters (e.g., HPRT, vimentin, actin, tubulin), intermediate filament promoters (e.g., desmin, neurofilaments, keratin, GFAP), therapeutic gene promoters (e.g., MDR type, CFTR, factor VIII), tissue-specific promoters (e.g., actin promoter in smooth muscle cells), promoters which are preferentially activated in dividing cells, promoters which respond to a stimulus (e.g., steroid hormone receptor, retinoic acid receptor), tetracycline-regulated transcriptional modulators, cytomegalovirus immediate-early, retroviral LTR, metallothionein, SV-40, E1a, and MLP promoters. Tetracycline-regulated transcriptional modulators and CMV promoters are described in WO 96/01313, U.S. Pat. Nos. 5,168,062 and 5,385,839, the contents of which are incorporated herein by reference.

Thus, the promoters which may be used to control gene expression include, but are not limited to, the cytomegalovirus (CMV) promoter, the SV40 early promoter region (Benoist and Chambon, 1981, Nature 290:304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42); prokaryotic expression vectors such as the b-lactamase promoter (Villa-Kamaroff, et al., 1978, Proc. Natl. Acad. Sci. U.S.A. 75:3727-3731), or the tac promoter (DeBoer, et al., 1983, Proc. Natl. Acad. Sci. U.S.A. 80:21-25); see also "Useful proteins from recombinant bacteria" in Scientific American, 1980, 242:74-94; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58), alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94), myelin basic protein gene control region which is active in oligodendrocyte cells in the brain (Readhead et al., 1987, Cell 48:703-712), myosin light chain-2 gene control region which is active in skeletal muscle (Sani, 1985, Nature 314:283-286), and gonadotropic releasing hormone gene control region which is active in the hypothalamus (Mason et al., 1986, Science 234:1372-1378).

Introduction of any one of the nucleotides of the present invention or a gene encoding the polypeptides of the present invention can also be accomplished with extrachromosomal substrates (transient expression) or artificial chromosomes (stable expression). Cells may also be cultured ex vivo in the presence of proteins of the present invention in order to proliferate or to produce a desired effect on or activity in such cells. Treated cells can then be introduced in vivo for therapeutic purposes. In addition to the use of viral vectors in the practice of the present invention, the present invention further includes a novel vector comprising operator and promoter elements operatively linked to polynucleotide sequences encoding a protein of interest. The adenoviral vector of the invention is the pAdenoVator-CMV5-Intron vector, which is described in detail in Examples.

4.2.6 Crypt Cell and Tissue Growth Activity

The SCFA2, SCFA4 or SCFA4v polypeptide of the invention exhibits growth factor activity and is involved in the proliferation and differentiation of intestinal crypt cells. SCFA2, SCFA4 or SCFA4v may also exhibit growth factor activity on other epithelial cells of the gastrointestinal tract. Administration of the polypeptide of the invention to crypt cells in vivo or ex vivo may maintain and expand cell populations in a totipotential state which would be useful for re-engineering damaged or diseased tissues, transplantation, manufacture of bio-pharmaceuticals and the development of bio-sensors. The ability to produce large quantities of human cells has important working applications for the production of human proteins which currently must be obtained from non-human sources or donors, implantation of cells to treat tissues for grafting such gastrointestinal cells.

It is contemplated that multiple different exogenous growth factors and/or cytokines may be administered in combination with the polypeptide of the invention to achieve the desired effect, including any of the growth factors listed herein, other stem cell maintenance factors, and specifically including stem cell factor (SCF), leukemia inhibitory factor (LIF), Flt-3 ligand (Flt-3L), any of the interleukins, recombinant soluble IL-6 receptor fused to IL-6, macrophage inflammatory protein 1-alpha (MIP-1-alpha), G-CSF, GM-CSF, thrombopoietin (TPO), platelet factor 4 (PF-4), platelet-derived growth factor (PDGF), neural growth factors, basic fibroblast growth factor (bFGF), keratinocyte growth factor-2 (KGF2), and glucagons-like peptide 2 (GLP-2).

Intestinal epithelial cells including crypt cells can be transfected with a polynucleotide of the invention to induce autocrine expression of the polypeptide of the invention. This will allow for generation of undifferentiated cell lines that are useful as is or that can then be differentiated into the desired mature cell types. These stable cell lines can also serve as a source of undifferentiated mRNA to create cDNA libraries and templates for polymerase chain reaction experiments. These studies would allow for the isolation and identification of differentially expressed genes in crypt cell populations that regulate crypt proliferation and/or maintenance.

Expansion and maintenance of epithelial stem cell populations will be useful in the treatment of many pathological conditions. For example, polypeptides of the present invention may be used to manipulate crypt cells in culture to give rise to gastrointestinal epithelial cells that can be used to augment or replace cells damaged by illness, autoimmune disease, accidental damage or genetic disorders inflammation caused by ionizing radiation, chemotherapy, infection and inflammation.

Expression of the polypeptide of the invention and its effect on crypt cells can also be manipulated to achieve controlled differentiation of the crypt cells into more differentiated cell types. A broadly applicable method of obtaining pure populations of a specific differentiated cell type from undifferentiated stem cell populations involves the use of a cell-type specific promoter driving a selectable marker In vitro cultures of intestinal epithelial cells including crypt cells can be used to determine if the polypeptide of the invention exhibits growth factor activity. Crypt cells are isolated from disaggregated colonic crypts from human and murine colonic mucosa, and the clonogenic activity of SCFA2, SCFA4 or SCFA4v can be assessed using the method described by Whitehead et al., Gastroenterology 117:858-865 (1999), which is herein incorporated by reference in its entirety. Growth factor activity can be assessed in the presence of the polypeptide of the invention alone or in combination with other growth factors or cytokines.

The compositions of the present invention can also be useful for proliferation of intestinal epithelial cells including crypt cells and for regeneration of oral and gastrointestinal tissue, i.e. for the treatment of injuries sustained by the epithelial layer which involve degeneration, death or trauma to epithelial crypt cells. More specifically, a composition can be used in the treatment of diseases of the gastrointestinal tract as recited herein.

Compositions of the invention can also be useful to promote better or faster closure of non-healing wounds, including without limitation pressure ulcers, ulcers associated with vascular insufficiency, surgical and traumatic wounds, and the like. Assays for wound healing activity include, without limitation, those described in: Winter, Epidermal Wound Healing, pp. 71-112 (Maibach, H. I. and Rovee, D. T., eds.), Year Book Medical Publishers, Inc., Chicago, as modified by Eaglstein and Mertz, J. Invest. Dermatol. 71:382-84 (1978).

4.2.7 Immunomodulatory Activity

A polypeptide of the present invention may exhibit activity relating to regulation of immune system components including, but not limited to cytokine production and/or activity, and/or cells of the immune system. A polynucleotide of the invention can encode a polypeptide exhibiting such attributes. Regulation of cytokines and/or cells of the immune system may include increasing and/or decreasing levels of cytokines or numbers of particular cells of the immune system.

With such immunomodulatory activity, polypeptides of the invention can be used to treat various immune disorders. These disorders include, but are not limited to inflammatory bowel disease (IBD), which includes ulcerative colitis and/or Crohn's disease, and mucositis as a consequence of anti-cancer therapies including radiation treatment and/or chemotherapy. The cause of these immune disorders can be, for example, idiopathic (i.e. of unknown cause), genetic, by infectious agents (eg. viruses, bacteria, fungi), and/or by damage induced by anti-cancer therapies (eg. radiation therapy and/or chemotherapy).

Modulation of immune responses and/or components of the immune system can be accomplished in a number of ways. Down-regulation may be in the form of inhibiting or blocking an immune response already in progress or may involve preventing the induction of an immune response. The functions of activated T cells may be inhibited by suppressing T cell responses or by inducing specific tolerance in T cells, or both. Immunosuppression of T cell responses is generally an active, non-antigen-specific, process that requires continuous exposure of the T cells to the suppressive agent. Tolerance, which involves inducing non-responsiveness or anergy in T cells, is distinguishable from immunosuppression in that it is generally antigen-specific and persists after exposure to the tolerizing agent has ceased. Operationally, tolerance can be demonstrated by the lack of a T cell response upon reexposure to specific antigen in the absence of tolerizing agent.

Inflammatory bowel disease is almost always mediated by one of two pathways: excessive T helper 1 (Th1)-cell response associated with high levels of IL-12, IFN-gamma, and/or TNF or excessive T helper 2 (Th2)-cell response associated with high levels of IL-4, IL-5, and/or IL-13 (Bouma et al., herein incorporated by reference in its entirety). Therefore a mechanism through which polypeptides of the invention could mediate immunomodulatory activity in disease treatment would be to down-regulate the numbers of Th1 and/or Th2 cell populations. Alternatively, another activity could be to decrease the levels of cytokines (eg. IL-12, IFN-gamma, TNF, IL-4, IL-5, and/or IL-13) that are associated with and/or mediate the inflammatory response.

The activity of the polypeptide of the present invention can, among other means, be measured by the following methods:

Assays for T-cell or thymocyte proliferation include without limitation those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 3, In Vitro assays for Mouse Lymphocyte Function 3.1-3.19; Chapter 7, Immunologic studies in Humans); Takai et al., J. Immunol. 137: 3494-3500, 1986; Bertagnolli et al., J. Immunol. 145:1706-1712, 1990; Bertagnolli et al., Cellular Immunology 133: 327-341, 1991; Bertagnolli, et al., I. Immunol. 149:3778-3783, 1992; Bowman et al., I. Immunol. 152:1756-1761, 1994.

Assays for cytokine production and/or proliferation of spleen cells, lymph node cells or thymocytes include, without limitation, those described in: Polyclonal T cell stimulation, Kruisbeek, A. M. and Shevach, E. M. In Current Protocols in Immunology. J. E. e.a. Coligan eds. Vol 1 pp. 3.12.1-3.12.14, John Wiley and Sons, Toronto. 1994; and Measurement of mouse and human interferon-γ, Schreiber, R. D. In Current Protocols in Immunology. J. E. e.a. Coligan eds. Vol 1 pp. 6.8.1-6.8.8, John Wiley and Sons, Toronto. 1994.

Assays for T-cell clone responses to antigens (which will identify, among others, proteins that affect APC-T cell interactions as well as direct T-cell effects by measuring proliferation and cytokine production) include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function; Chapter 6, Cytokines and their cellular receptors; Chapter 7, Immunologic studies in Humans); Weinberger et al., Proc. Natl. Acad. Sci. USA 77:6091-6095, 1980; Weinberger et al., Eur. J. Immun. 11:405-411, 1981; Takai et al., J. Immunol. 137:3494-3500, 1986; Takai et al., J. Immunol. 140:508-512, 1988.)

4.2.8 Chemotactic/Chemokinetic Activity

A polypeptide of the present invention may be involved in chemotactic or chemokinetic activity for mammalian cells, including, for example, monocytes, fibroblasts, neutrophils, T-cells, mast cells, eosinophils, epithelial and/or endothelial cells. A polynucleotide of the invention can encode a polypeptide exhibiting such attributes. Chemotactic and chemokinetic receptor activation can be used to mobilize or attract a desired cell population to a desired site of action. Chemotactic or chemokinetic compositions (e.g. proteins, antibodies, binding partners, or modulators of the invention) provide particular advantages in treatment of wounds and other trauma to tissues, as well as in treatment of localized infections. For example, attraction of lymphocytes, monocytes or neutrophils to tumors or sites of infection may result in improved immune responses against a tumor or an infecting agent.

A protein or peptide has chemotactic activity for a particular cell population if it can stimulate, directly or indirectly, the directed orientation or movement of such cell population. Preferably, the protein or peptide has the ability to directly stimulate directed movement of cells. Whether a particular protein has chemotactic activity for a population of cells can be readily determined by employing such protein or peptide in any known assay for cell chemotaxis.

Assays for chemotactic activity (which will identify proteins that induce or prevent chemotaxis) consist of assays that measure the ability of a protein to induce the migration of cells across a membrane as well as the ability of a protein to induce the adhesion of one cell population to another cell population. Suitable assays for movement and adhesion include, without limitation, those described in: Current Protocols in Immunology, Ed by J. E. Coligan, A. M. Kruisbeek, D. H. Marguiles, E. M. Shevach, W. Strober, Pub. Greene Publishing Associates and Wiley-Interscience (Chapter 6.12, Measurement of alpha and beta Chemokines 6.12.1-6.12.28; Taub et al. J. Clin. Invest. 95:1370-1376, 1995; Lind et al. APMIS 103:140-146, 1995; Muller et al Eur. J. Immunol. 25:1744-1748; Gruber et al. J. of Immunol. 152:5860-5867, 1994; Johnston et al. J. of Immunol. 153:1762-1768, 1994.

4.2.9 Drug Screening

Screening for a useful compound involves administering the candidate compound over a range of doses to a non-human animal, and assaying at various time points for the effect(s) of the compound on the activity of the SCFA2, SCFA4 or SCFA4v protein. The compound may be administered prior to or at the onset of abdominal distension. Administration may be oral, or by suitable injection, depending on the chemical nature of the compound being evaluated. The cellular response to the compound is evaluated over time using appropriate biochemical and/or histological assays.

Sources for test compounds that may be screened for ability to bind to or modulate (i.e., increase or decrease) the activity of polypeptides of the invention include (1) inorganic and organic chemical libraries, (2) natural product libraries, and (3) combinatorial libraries comprised of either random or mimetic peptides, oligonucleotides or organic molecules.

Chemical libraries may be readily synthesized or purchased from a number of commercial sources, and may include structural analogs of known compounds or compounds that are identified as "hits" or "leads" via natural product screening.

The sources of natural product libraries are microorganisms (including bacteria and fungi), animals, plants or other vegetation, or marine organisms, and libraries of mixtures for screening may be created by: (1) fermentation and extraction of broths from soil, plant or marine microorganisms or (2) extraction of the organisms themselves. Natural product libraries include polyketides, non-ribosomal peptides, and (non-naturally occurring) variants thereof. For a review, see Science 282:63-68 (1998).

Combinatorial libraries are composed of large numbers of peptides, oligonucleotides or organic compounds and can be readily prepared by traditional automated synthesis methods, PCR, cloning or proprietary synthetic methods. Of particular interest are peptide and oligonucleotide combinatorial libraries. Still other libraries of interest include peptide, protein, peptidomimetic, multiparallel synthetic collection, recombinatorial, and polypeptide libraries. For a review of combinatorial chemistry and libraries created therefrom, see Myers, Curr. Opin. Biotechnol. 8:701-707 (1997). For reviews and examples of peptidomimetic libraries, see Al-Obeidi et al., Mol. Biotechnol, 9(3):205-23 (1998); Hruby et al., Curr Opin Chem Biol, 1(1):114-19 (1997); Dorner et al., Bioorg Med Chem, 4(5):709-15 (1996) (alkylated dipeptides).

4.3 Diseases Amendable to SCFA2, SCFA4 or SCFA4v Therapy

In one aspect, the present invention provides pharmaceutical reagents and methods useful for treating diseases and conditions wherein epithelialization is desired. SCFA2, SCFA4 and SCFA4v polypeptides are useful to increase cytoprotection, proliferation and/or differentiation of epithelial cells of the oral and gastrointestinal tract. Specifically, SCFA2, SCFA4 and SCFA4v polypeptides are useful to treat or prevent diseases or conditions that include without limitation gastrointestinal diseases, mucositis of the gastrointestinal tract, mucositis of the oropharynx, lips and esophagus (oral mucositis), inflammatory bowel disease, short bowel syndrome, gastric and duodenal ulcers, erosions of the gastrointestinal tract including erosive gastritis, esophagitis, esophageal reflux and other conditions including wounds, burns, ophthalmic disorders, and any disorder where stimulation of epithelial cell proliferation or regeneration is desired. Treatment of diseases that result in insufficient production of mucus throughout the oral and gastrointestinal tract is also contemplated.

Mucositis, which includes oral and gastrointestinal mucositis, is a complication of some cancer therapies in which the lining of the digestive system becomes inflamed. SCFA2, SCFA4 and SCFA4v is useful for preventing and/or ameliorating the degeneration of the mucosa of the alimentary tract that is caused by chemotherapy and/or radiation therapy given to a patent for the treatment of cancer, or is given as an adjuvant therapy following the removal of a tumor. Exemplary chemotherapeutic agents include, without limitation, BCNU, busulfan, carboplatin, cyclophosphamide, tannorubicin, doxorubicin, etoposide, 5-fluorouracil (5-FU), gemcytabine, ifophamide, irinotecan, melphalan, methotrexate, navelbine, totpotecan, and taxol, and exemplary treatment regimens include without limitation, BEAM (busulfan, etoposide, cytosine, arabinoside, methotrexate); cyclophosphamide and total body irradiation; cyclophosphamine, total body irradiation and etoposide; cyclophosphamide and busulfan; and 5-fluorouracil with leucovorin or levamisole. Treatment, pretreatment or post-treatment with SCFA2, SCFA4 and SCFA4v is useful to generate a cytoprotective effect or regeneration or both, for example, of the mucosa of the small intestine and colon, allowing increased dosages of therapies while reducing their potential side effects.

Inflammatory bowel disease that can be treated with SCFA2, SCFA4 and SCFA4v includes general inflammatory bowel disease that is characterized by chronic, relapsing, inflammatory disorders of unknown origin, Crohn's disease, dysplasia associated with inflammatory bowel disease, intermediate colitis, ulcerative colitis; non-infectious colitis including active colitis, antibiotic-associated colitis, collagenous colitis, diversion colitis, eosinophilic colitis, graft versus host disease, granulomatous colitis, ischaemic colitis, hemorrhagic colitis, malakoplakia, necrotizing enterocolitis, radiation enterocolitis, typhlitis; infectious colitis including adenovirus and amebic colitis, balantidiasis, HSV/AIDS associated colitis, and colitis caused by trypanosomes, *E. coli, Mycobacterium* avium intracellulare, Sotavirus, *Salmonella, Shigella, Campylobacter jejuni, Clostridium, Botulinum*, and colitis associated with schistosomiasis, spirochetosis, syphilis, trichuriasis, tuberculosis typhoid fever, *Vibrio cholera*, and *Yersinia*.

Short bowel syndrome is a group of problems affecting people who have had half or more of their small intestine removed. The most common reason for removing part of the small intestine is to treat Crohn's disease. In addition, surgical resection of part of the intestine may be required to remove cancerous growths. Diarrhea is the main symptom of short bowel syndrome. Other symptoms include cramping, bloating, and heartburn. Many people with short bowel syndrome are malnourished because their remaining small intestine is unable to absorb enough water, vitamins, and other nutrients from food. They may also become dehydrated, which can be life threatening. Problems associated with dehydration and malnutrition include weakness, fatigue, depression, weight loss, bacterial infections, and food sensitivities. Short bowel syndrome is treated through changes in diet, intravenous feeding, vitamin and mineral supplements, and medicine to relieve symptoms. SCFA2, SCFA4 and SCFA4v polypeptides can be useful to increase the proliferation of the unresected intestinal tissue, thereby increasing the absorptive surface area of the intestine, and ameliorate the symptoms associated with short bowel syndrome.

The cytoprotective and/or regenerative activity of SCFA2, SCFA4 and SCFA4v polypeptides can be tested in in vivo models of radiation induced mucositis (Withers and Elkind, Int J Radiat 17:261-267 (1970), herein incorporated by reference; in in vivo chemotherapy-induced mucositis (Soris et al., Oral Surg Oral Med Oral Pathol 69:437-443 (1990); Moore, Cancer Chemother Pharmacol 15:11-15 (1985); Farell et al., Cell Prolif 35:78-85 (2002), all of which are incorporated by reference in their entirety); in a dextran sulfate sodium (DSS) model of colitis and small intestinal ulceration or inflammation (Jeffers et al., Gastroenterology 123: 1151-1162 (2002), Han et al., Am J Physiol Gastrointest Liver Physiol 279:G1011-G1022 (2000); and in a surgical model of short bowel syndrome (SBS) (Scott et al. Am J Physiol G911-G921 (1998); Helmrath et al., J Am Coll Surg 183:441-449 (1996)), herein incorporated by reference in their entirety).

Comparisons of SCFA2, SCFA4 and SCFA4v mRNA and protein expression levels between diseased cells, tissue and corresponding normal samples are made to determine if the subject is responsive to SCFA2, SCFA4 and SCFA4v therapy. Methods for detecting and quantifying the expression of SCFA2, SCFA4 and SCFA4v polypeptide mRNA or protein use standard nucleic acid and protein detection and quantitation techniques that are well known in the art and are described in Sambrook, et al., *Molecular Cloning: A Laboratory Manual*, Cold Spring Harbor Laboratory, NY (1989) or Ausubel, et al., *Current Protocols in Molecular Biology*, John Wiley & Sons, New York, N.Y. (1989), both of which are incorporated herein by reference in their entirety. Standard methods for the detection and quantification of SCFA2, SCFA4 and SCFA4v mRNA include in situ hybridization using labeled SCFA2, SCFA4 and SCFA4v riboprobes (Gemou-Engesaeth, et al., *Pediatrics* 109: E24-E32 (2002), herein incorporated by reference in its entirety), northern blot and related techniques using SCFA2, SCFA4 and SCFA4v polynucleotide probes (Kunzli, et al., *Cancer* 94: 228 (2002), herein incorporated by reference in its entirety, herein incorporated by reference in its entirety), RT-PCR analysis using SCFA2, SCFA4 and SCFA4v-specific primers (Angchaiskisiri, et al., *Blood* 99:130 (2002)), and other amplification detection methods, such as branched chain DNA solution hybridization assay (Jardi, et al., *J. Viral Hepat.* 8:465-471 (2001), herein incorporated by reference in its entirety), transcription-mediated amplification (Kimura, et al., *J. Clin. Microbiol.* 40:439-445 (2002)), microarray products, such as oligos, cDNAs, and monoclonal antibodies, and real-time PCR (Simpson, et al., *Molec. Vision,* 6:178-183 (2000), herein incorporated by reference in its entirety). Standard methods for the detection and quantification of SCFA2, SCFA4 and SCFA4v protein include western blot analysis (Sambrook, et al., *Molecular Cloning: A Laboratory Manual*, Cold Spring Harbor Laboratory, NY (1989), Ausubel, et al., *Current Protocols in Molecular Biology*, John Wiley & Sons, New York, N.Y. (1989)), immunocytochemistry (Racila, et al., *Proc. Natl. Acad. Sci. USA* 95:4589-4594 (1998) supra), and a variety of immunoassays, including enzyme-linked immunosorbant assay (ELISA), radioimmuno assay (RIA), and specific enzyme immunoassay (EIA) (Sambrook, et al., *Molecular Cloning: A Laboratory Manual*, Cold Spring Harbor Laboratory, NY (1989), Ausubel, et al., *Current Protocols in Molecular Biology*, John Wiley & Sons, New York, N.Y. (1989)).

The diseases and conditions treatable by methods of the present invention preferably occur in mammals. Mammals include, for example, humans and other primates, as well as pet or companion animals such as dogs and cats, laboratory animals such as rats, mice and rabbits, and farm animals such as horses, pigs, sheep, and cattle.

4.3.1 Therapeutic Methods

The compositions (including polypeptide fragments, analogs, variants and antibodies or other binding partners or modulators including antisense polynucleotides) of the invention have numerous applications in a variety of therapeutic methods. Examples of therapeutic applications include, but are not limited to, those exemplified herein.

One embodiment of the invention is the administration of an effective amount of SCFA2, SCFA4 and SCFA4v polypeptides or other composition of the invention to individuals affected by a disease or disorder that can be treated the peptides of the invention. While the mode of administration is not particularly important, parenteral administration is preferred. Exemplary modes of administration are to deliver asubcutaneous or intravenous bolus. The dosage of SCFA2, SCFA4 and SCFA4v polypeptides or other composition of the invention will normally be determined by the prescribing physician. It is to be expected that the dosage will vary according to the age, weight, condition and response of the individual patient. Typically, the amount of polypeptide administered per dose will be in the range of about 0.01 µg/kg to 100 mg/kg of body weight, with the preferred dose being about 0.1 µg/kg to 10 mg/kg of patient body weight. For parenteral administration, SCFA2, SCFA4 and SCFA4v polypeptides of the invention will be formulated in an injectable form combined with a pharmaceutically acceptable parenteral vehicle. Such vehicles are well known in the art and examples include water, saline, Ringer's solution, dextrose solution, and solutions consisting of small amounts of the human serum albumin. The vehicle may contain minor amounts of additives that maintain the isotonicity and stability of the polypeptide or other active ingredient. The preparation of such solutions is within the skill of the art.

4.3.2 Pharmaceutical Formulations

A protein or other composition of the present invention (from whatever source derived, including without limitation from recombinant and non-recombinant sources and including antibodies and other binding partners of the polypeptides of the invention) may be administered to a patient in need, by itself, or in pharmaceutical compositions where it is mixed with suitable carriers or excipient(s) at doses to treat or ameliorate a variety of disorders. Such a composition may optionally contain (in addition to protein or other active ingredient and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, lymphokines, or other hematopoietic factors and various growth factors such as any of the FGFs, epidermal growth factor (EGF), platelet-derived growth factor (PDGF), transforming growth factors (TGF-α and TGF-β), insulin-like growth factor (IGF), keratinocyte growth factor (KGF), and the like, as well as cytokines described herein.

The pharmaceutical composition may further contain other agents which either enhance the activity of the protein or other active ingredient or complement its activity or use in treatment. Such additional factors and/or agents may be included in the pharmaceutical composition to produce a synergistic effect with protein or other active ingredient of the invention, or to minimize side effects. Conversely, protein or other active ingredients of the present invention may be included in formulations of the particular cytokine, lymphokine, other hematopoietic factor, thrombolytic or anti-thrombotic factor, or anti-inflammatory agent to minimize side effects of the clotting factor, cytokine, lymphokine, other hematopoietic factor, thrombolytic or anti-thrombotic factor, or anti-inflammatory agent (such as IL-1Ra, IL-1 Hy1, IL-1 Hy2, anti-TNF, corticosteroids, immunosuppressive agents). A protein of the present invention may be active in multimers (e.g., heterodimers or homodimers) or complexes with itself or other proteins. As a result, pharmaceutical compositions of the invention may comprise a protein of the invention in such multimeric or complexed form.

As an alternative to being included in a pharmaceutical composition of the invention including a first protein, a second protein or a therapeutic agent may be concurrently administered with the first protein (e.g., at the same time, or at differing times provided that therapeutic concentrations of the combination of agents is achieved at the treatment site). Techniques for formulation and administration of the compounds of the instant application may be found in "Remington's Pharmaceutical Sciences," Mack Publishing Co., Easton, Pa., latest edition. A therapeutically effective dose further refers to that amount of the compound sufficient to result in amelioration of symptoms, e.g., treatment, healing, prevention or amelioration of the relevant medical condition, or an increase in rate of treatment, healing, prevention or amelioration of such conditions. When applied to an individual active ingredient, administered alone, a therapeutically effective dose refers to that ingredient alone. When applied to a combination, a therapeutically effective dose refers to combined amounts of the active ingredients that result in the therapeutic effect, whether administered in combination, serially or simultaneously.

In practicing the method of treatment or use of the present invention, a therapeutically effective amount of protein or other active ingredient of the present invention is administered to a mammal having a condition to be treated. Protein or other active ingredient of the present invention may be administered in accordance with the method of the invention either alone or in combination with other therapies such as treatments employing cytokines, lymphokines or other hematopoietic factors. When co-administered with one or more cytokines, lymphokines or other hematopoietic factors, protein or other active ingredient of the present invention may be administered either simultaneously with the cytokine(s), lymphokine(s), other hematopoietic factor(s), thrombolytic or anti-thrombotic factors, or sequentially. If administered sequentially, the attending physician will decide on the appropriate sequence of administering protein or other active ingredient of the present invention in combination with cytokine(s), lymphokine(s), other hematopoietic factor(s), thrombolytic or anti-thrombotic factors.

4.3.3 Routes of Administration

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections. Administration of protein or other active ingredient of the present invention used in the pharmaceutical composition or to practice the method of the present invention can be carried out in a variety of conventional ways, such as oral ingestion, inhalation, topical application or cutaneous, subcutaneous, intraperitoneal (IP), parenteral or intravenous injection. Subcutaneous or intravenous administration to the patient is preferred.

Alternatively, one may administer the compound in a local rather than systemic manner, for example, via injection of the compound directly into the tissue, often in a depot or sustained release formulation.

In another embodiment, the implantation of cells producing SCFA2, SCFA4 and SCFA4v (cell therapy) into a subject in need of proliferation and/or stimulation of epithelial cells is contemplated. Cells that do not normally express SCFA2, SCFA4 and SCFA4v or that express low levels of SCFA2, SCFA4 and SCFA4v may be modified to produce therapeutic levels of SCFA2, SCFA4 and SCFA4v by transformation with a polynucleotide that encodes SCFA2, SCFA4 and SCFA4v. The cells may be of the same species as the subject, or may be derived from a different species. Preferably, the cells are derived from the subject in need of SCFA2, SCFA4 and SCFA4v therapy. Human or nonhuman cells may be implanted in a subject using a biocompatible, semi-permeable polymeric enclosure to allow release of SCFA2, SCFA4 and SCFA4v protein, or may be implanted directly without encapsulation.

In another embodiment, in vivo gene therapy is contemplated. A nucleotide sequence encoding SCFA2, SCFA4 and SCFA4v is introduced directly into a subject for secretion of the protein to prevent or treat the diseases as recited herein. The nucleotide encoding SCFA2, SCFA4 and SCFA4v may be injected directly into the tissue to be treated, or it may be delivered into the cells of the affected tissue by a viral vector e.g. adenovirus vector or retrovirus vector. Physical transfer of appropriate vectors containing a SCFA2, SCFA4 and SCFA4v-encoding nucleic acid may also be achieved by methods including liposome-mediated transfer, direct injection of naked DNA, receptor-mediated transfer, or microparticle bombardment.

The polypeptides of the invention are administered by any route that delivers an effective dosage to the desired site of action. The determination of a suitable route of administration and an effective dosage for a particular indication is within the level of skill in the art. Preferably for wound treatment, one administers the therapeutic compound directly to the site. Suitable dosage ranges for the polypeptides of the invention can be extrapolated from these dosages or from similar studies in appropriate animal models. Dosages can then be adjusted as necessary by the clinician to provide maximal therapeutic benefit.

4.3.4 Compositions/Formulations

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. These pharmaceutical compositions may be manufactured in a manner that is itself known, e.g., by means of conventional mixing, dissolving, granulating, dragee-making, levigating, emulsifying, encapsulating, entrapping or lyophilizing processes. Proper formulation is dependent upon the route of administration chosen. When a therapeutically effective amount of protein or other active ingredient of the present invention is administered orally, protein or other active ingredient of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% protein or other active ingredient of the present invention, and preferably from about 25 to 90% protein or other active ingredient of the present invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of protein or other active ingredient of the present invention, and preferably from about 1 to 50% protein or other active ingredient of the present invention.

When a therapeutically effective amount of protein or other active ingredient of the present invention is administered by intravenous, cutaneous or subcutaneous injection, protein or other active ingredient of the present invention will be in the form of a pyrogen-free, parenterally acceptable aqueous solution. The preparation of such parenterally acceptable protein or other active ingredient solutions, having due regard to pH, isotonicity, stability, and the like, is within the skill in the art. A preferred pharmaceutical composition for intravenous, cutaneous, or subcutaneous injection should contain, in addition to protein or other active ingredient of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art. For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch. The compounds may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a co-solvent system comprising benzyl alcohol, a nonpolar surfactant, a water-miscible organic polymer, and an aqueous phase. The co-solvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose. Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various types of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein or other active ingredient stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols. Many of the active ingredients of the invention may be provided as salts with pharmaceutically compatible counter ions. Such pharmaceutically acceptable base addition salts are those salts which retain the biological effectiveness and properties of the free acids and which are obtained by reaction with inorganic or organic bases such as sodium hydroxide, magnesium hydroxide, ammonia, trialkylamine, dialkylamine, monoalkylamine, dibasic amino acids, sodium acetate, potassium benzoate, triethanol amine and the like.

The pharmaceutical composition of the invention may be in the form of a complex of the protein(s) or other active ingredient of present invention along with protein or peptide antigens. The protein and/or peptide antigen will deliver a stimulatory signal to both B and T lymphocytes. B lymphocytes will respond to antigen through their surface immunoglobulin receptor. T lymphocytes will respond to antigen through the T cell receptor (TCR) following presentation of the antigen by MHC proteins. MHC and structurally related proteins including those encoded by class I and class II MHC genes on host cells will serve to present the peptide antigen(s) to T lymphocytes. The antigen components could also be supplied as purified MHC-peptide complexes alone or with co-stimulatory molecules that can directly signal T cells. Alternatively antibodies able to bind surface immunoglobulin and other molecules on B cells as well as antibodies able to bind the TCR and other molecules on T cells can be combined with the pharmaceutical composition of the invention.

The pharmaceutical composition of the invention may be in the form of a liposome in which protein of the present invention is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithins, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

The amount of protein or other active ingredient of the present invention in the pharmaceutical composition of the present invention will depend upon the nature and severity of the condition being treated, and on the nature of prior treatments which the patient has undergone. Ultimately, the attending physician will decide the amount of protein or other active ingredient of the present invention with which to treat each individual patient. Initially, the attending physician will administer low doses of protein or other active ingredient of the present invention and observe the patient's response. Larger doses of protein or other active ingredient of the present invention may be administered until the optimal therapeutic effect is obtained for the patient, and at that point the dosage is not increased further. It is contemplated that the various pharmaceutical compositions used to practice the method of the present invention should contain about 0.01 μg to about 100 mg (preferably about 0.1 μg to about 10 mg, more preferably about 0.1 μg to about 1 mg) of protein or other active ingredient of the present invention per kg body weight. For compositions of the present invention which are useful for bone, cartilage, tendon or ligament regeneration, the therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or tissue damage. Topical administration may be suitable for wound healing and tissue repair. Therapeutically useful agents other than a protein or other active ingredient of the invention which may also optionally be included in the composition as described above, may alternatively or additionally, be administered simultaneously or sequentially with the composition in the methods of the invention. Preferably for bone and/or cartilage formation, the composition would include a matrix capable of delivering the protein-containing or other active ingredient-containing composition to the site of bone and/or cartilage damage, providing a structure for the developing bone and cartilage and optimally capable of being resorbed into the body. Such matrices may be formed of materials presently in use for other implanted medical applications.

The choice of matrix material is based on biocompatibility, biodegradability, mechanical properties, cosmetic appearance and interface properties. The particular application of the compositions will define the appropriate formulation. Potential matrices for the compositions may be biodegradable and chemically defined calcium sulfate, tricalcium phosphate, hydroxyapatite, polylactic acid, polyglycolic acid and polyanhydrides. Other potential materials are biodegradable and biologically well-defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalcium phosphate. The bioceramics may be altered in composition, such as in calcium-aluminate-phosphate and processing to alter pore size, particle size, particle shape, and biodegradability. Presently preferred is a 50:50 (mole weight) copolymer of lactic acid and glycolic acid in the form of porous particles having diameters ranging from 150 to 800 microns. In some applications, it will be useful to utilize a sequestering agent, such as carboxymethyl cellulose or autologous blood clot, to prevent the protein compositions from disassociating from the matrix.

A preferred family of sequestering agents is cellulosic materials such as alkylcelluloses (including hydroxyalkylcelluloses), including methylcellulose, ethylcellulose, hydroxyethylcellulose, hydroxypropylcellulose, hydroxypropylmethylcellulose, and carboxymethylcellulose, the most preferred being cationic salts of carboxymethylcellulose (CMC). Other preferred sequestering agents include hyaluronic acid, sodium alginate, poly(ethylene glycol), polyoxyethylene oxide, carboxyvinyl polymer and poly(vinyl alcohol). The amount of sequestering agent useful herein is 0.5-20 wt %, preferably 1-10 wt % based on total formulation weight, which represents the amount necessary to prevent desorption of the protein from the polymer matrix and to provide appropriate handling of the composition, yet not so much that the progenitor cells are prevented from infiltrating the matrix, thereby providing the protein the opportunity to assist the osteogenic activity of the progenitor cells. In further compositions, proteins or other active ingredient of the invention may be combined with other agents beneficial to the treatment of the bone and/or cartilage defect, wound, or tissue in question. These agents include various growth factors such as epidermal growth factor (EGF), platelet derived growth factor (PDGF), transforming growth factors (TGF-α and TGF-β), and insulin-like growth factor (IGF).

The therapeutic compositions are also presently valuable for veterinary applications. Particularly domestic animals and thoroughbred horses, in addition to humans, are desired patients for such treatment with proteins or other active ingredient of the present invention. The dosage regimen of a protein-containing pharmaceutical composition to be used in tissue regeneration will be determined by the attending physician considering various factors which modify the action of the proteins, e.g., amount of tissue weight desired to be formed, the site of damage, the condition of the damaged tissue, the size of a wound, type of damaged tissue (e.g., bone), the patient's age, sex, and diet, the severity of any infection, time of administration and other clinical factors. The dosage may vary with the type of matrix used in the reconstitution and with inclusion of other proteins in the pharmaceutical composition. For example, the addition of other known growth factors, such as IGF I (insulin like growth factor I), to the final composition, may also effect the dosage. Progress can be monitored by periodic assessment of tissue/bone growth and/or repair, for example, X-rays, histomorphometric determinations and tetracycline labeling.

Polynucleotides of the present invention can also be used for gene therapy. Such polynucleotides can be introduced either in vivo or ex vivo into cells for expression in a mammalian subject. Polynucleotides of the invention may also be administered by other known methods for introduction of nucleic acid into a cell or organism (including, without limitation, in the form of viral vectors or naked DNA). Cells may also be cultured ex vivo in the presence of proteins of the present invention in order to proliferate or to produce a desired effect on or activity in such cells. Treated cells can then be introduced in vivo for therapeutic purposes.

4.3.5 Effective Dosage

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amount is well within the capability of those skilled in the art, especially in light of the detailed disclosure provided herein. For any compound used in the method of the invention, the therapeutically effective dose can be estimated initially from appropriate in vitro assays. For example, a dose can be formulated in animal models to achieve a circulating concentration range that can be used to more accurately determine useful doses in humans. For example, a dose can be formulated in animal models to achieve a circulating concentration range that includes the $IC_{50}$ as determined in cell culture (i.e., the concentration of the test compound which achieves a half-maximal inhibition of the protein's biological activity). Such information can be used to more accurately determine useful doses in humans.

A therapeutically effective dose refers to that amount of the compound that results in amelioration of symptoms or a prolongation of survival in a patient. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. See, e.g., Fingl et al., 1975, in "The Pharmacological Basis of Therapeutics", Ch. 1 p. 1. Dosage amount and interval may be adjusted individually to provide plasma levels of the active moiety which are sufficient to maintain the desired effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compounds should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

An exemplary dosage regimen for polypeptides or other compositions of the invention will be in the range of about 0.01 µg/kg to 100 mg/kg of body weight daily, with the preferred dose being about 0.1 µg/kg to 25 mg/kg of patient body weight daily, varying in adults and children. Dosing may be once daily, or equivalent doses may be delivered at longer or shorter intervals.

The amount of composition administered will, of course, be dependent on the subject being treated, on the subject's age and weight, the severity of the affliction, the manner of administration and the judgment of the prescribing physician.

4.3.6 Diagnostic Assays and Kits

The present invention further provides methods to identify the presence or expression of one of the ORFs of the present invention, or homolog thereof, in a test sample, using a nucleic acid probe or antibodies of the present invention, optionally conjugated or otherwise associated with a suitable label.

In general, methods for detecting a polynucleotide of the invention can comprise contacting a sample with a compound that binds to and forms a complex with the polynucleotide for a period sufficient to form the complex, and detecting the complex, so that if a complex is detected, a polynucleotide of the invention is detected in the sample. Such methods can also comprise contacting a sample under stringent hybridization conditions with nucleic acid primers that anneal to a polynucleotide of the invention under such conditions, and amplifying annealed polynucleotides, so that if a polynucleotide is amplified, a polynucleotide of the invention is detected in the sample.

In general, methods for detecting a polypeptide of the invention can comprise contacting a sample with a compound that binds to and forms a complex with the polypeptide for a period sufficient to form the complex, and detecting the complex, so that if a complex is detected, a polypeptide of the invention is detected in the sample.

In detail, such methods comprise incubating a test sample with one or more of the antibodies or one or more of the nucleic acid probes of the present invention and assaying for binding of the nucleic acid probes or antibodies to components within the test sample.

Conditions for incubating a nucleic acid probe or antibody with a test sample vary. Incubation conditions depend on the format employed in the assay, the detection methods employed, and the type and nature of the nucleic acid probe or antibody used in the assay. One skilled in the art will recognize that any one of the commonly available hybridization, amplification or immunological assay formats can readily be adapted to employ the nucleic acid probes or antibodies of the present invention. Examples of such assays can be found in Chard, T., An Introduction to Radioimmunoassay and Related Techniques, Elsevier Science Publishers, Amsterdam, The Netherlands (1986); Bullock, G. R. et al., Techniques in Immunocytochemistry, Academic Press, Orlando, Fla. Vol. 1 (1982), Vol. 2 (1983), Vol. 3 (1985); Tijssen, P., Practice and Theory of immunoassays: Laboratory Techniques in Biochemistry and Molecular Biology, Elsevier Science Publishers, Amsterdam, The Netherlands (1985). The test samples of the present invention include cells, protein or membrane extracts of cells, or biological fluids such as sputum, blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily adapted in order to obtain a sample which is compatible with the system utilized.

In another embodiment of the present invention, kits are provided which contain the necessary reagents to carry out the assays of the present invention. Specifically, the invention provides a compartment kit to receive, in close confinement, one or more containers which comprises: (a) a first container comprising one of the probes or antibodies of the present invention; and (b) one or more other containers comprising one or more of the following: wash reagents, reagents capable of detecting presence of a bound probe or antibody.

In detail, a compartment kit includes any kit in which reagents are contained in separate containers. Such containers include small glass containers, plastic containers or strips of plastic or paper. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the antibodies used in the assay, containers which contain wash reagents (such as phosphate buffered saline, Tris-buffers, etc.), and containers which contain the reagents used to detect the bound antibody or probe. Types of detection reagents include labeled nucleic acid probes, labeled secondary antibodies, or in the alternative, if the primary antibody is labeled, the enzymatic, or antibody binding reagents which are capable of reacting with the labeled antibody. One skilled in the art will readily recognize that the disclosed probes and antibodies of the present invention can be readily incorporated into one of the established kit formats which are well known in the art.

4.3.7 Screening Assays

Using the isolated proteins and polynucleotides of the invention, the present invention further provides methods of obtaining and identifying modulatory agents which bind to a polypeptide encoded by an ORF corresponding to the nucleotide sequence set forth in SEQ ID NO: 4, 15, 24, or 50, or bind to a specific domain of the polypeptide encoded by the nucleic acid. In detail, said method comprises the steps of:

(a) contacting an agent with an isolated protein encoded by an ORF of the present invention, or nucleic acid of the invention; and (b) determining whether the agent binds to said protein or said nucleic acid.

The modulatory agents may increase or decrease the proliferative activity of SCFA2, SCFA4 and SCFA4v on epithelial cells.

In general, such methods for identifying compounds that bind to a polynucleotide of the invention can comprise contacting a compound with a polynucleotide of the invention for a time sufficient to form a polynucleotide/compound complex, and detecting the complex, so that if a polynucleotide/compound complex is detected, a compound that binds to a polynucleotide of the invention is identified.

Likewise, in general, therefore, such methods for identifying compounds that bind to a polypeptide of the invention can comprise contacting a compound with a polypeptide of the invention for a time sufficient to form a polypeptide/compound complex, and detecting the complex, so that if a polypeptide/compound complex is detected, a compound that binds to a polynucleotide of the invention is identified.

Methods for identifying compounds that bind to a polypeptide of the invention can also comprise contacting a compound with a polypeptide of the invention in a cell for a time sufficient to form a polypeptide/compound complex, wherein the complex drives expression of a target gene sequence in the cell, and detecting the complex by detecting reporter gene sequence expression, so that if a polypeptide/compound complex is detected, a compound that binds a polypeptide of the invention is identified.

Compounds identified via such methods can include compounds which modulate the activity of a polypeptide of the invention (that is, increase or decrease its activity, relative to activity observed in the absence of the compound). Alternatively, compounds identified via such methods can include compounds which modulate the expression of a polynucleotide of the invention (that is, increase or decrease expression relative to expression levels observed in the absence of the compound). Compounds, such as compounds identified via the methods of the invention, can be tested using standard assays well known to those of skill in the art for their ability to modulate activity/expression.

The agents screened in the above assay can be, but are not limited to, peptides, carbohydrates, vitamin derivatives, or other pharmaceutical agents. The agents can be selected and screened at random or rationally selected or designed using protein modeling techniques.

For random screening, agents such as peptides, carbohydrates, pharmaceutical agents and the like are selected at random and are assayed for their ability to bind to the protein encoded by the ORF of the present invention. Alternatively, agents may be rationally selected or designed. As used herein, an agent is said to be "rationally selected or designed" when the agent is chosen based on the configuration of the particular protein. For example, one skilled in the art can readily adapt currently available procedures to generate peptides, pharmaceutical agents and the like, capable of binding to a specific peptide sequence, in order to generate rationally designed antipeptide peptides, for example see Hurby et al., Application of Synthetic Peptides: Antisense Peptides," In Synthetic Peptides, A User's Guide, W.H. Freeman, NY (1992), pp. 289-307, and Kaspczak et al., Biochemistry 28:9230-8 (1989), or pharmaceutical agents, or the like.

In addition to the foregoing, one class of agents of the present invention, as broadly described, can be used to control gene expression through binding to one of the ORFs or EMFs of the present invention. As described above, such agents can be randomly screened or rationally designed/selected. Targeting the ORF or EMF allows a skilled artisan to design sequence specific or element specific agents, modulating the expression of either a single ORF or multiple ORFs which rely on the same EMF for expression control. One class of DNA binding agents are agents which contain base residues which hybridize or form a triple helix formation by binding to DNA or RNA. Such agents can be based on the classic phosphodiester, ribonucleic acid backbone, or can be a variety of sulfhydryl or polymeric derivatives which have base attachment capacity.

Agents suitable for use in these methods usually contain 20 to 40 bases and are designed to be complementary to a region of the gene involved in transcription (triple helix—see Lee et al., Nucl. Acids Res. 6:3073 (1979); Cooney et al., Science 241:456 (1988); and Dervan et al., Science 251:1360 (1991)) or to the mRNA itself (antisense—Okano, J. Neurochem. 56:560 (1991); Oligodeoxynucleotides as Antisense Inhibitors of Gene Expression, CRC Press, Boca Raton, Fla. (1988)). Triple helix-formation optimally results in a shut-off of RNA transcription from DNA, while antisense RNA hybridization blocks translation of an mRNA molecule into polypeptide. Both techniques have been demonstrated to be effective in model systems. Information contained in the sequences of the present invention is necessary for the design of an antisense or triple helix oligonucleotide and other DNA binding agents.

Agents which bind to a protein encoded by one of the ORFs of the present invention can be used as a diagnostic agent. Agents which bind to a protein encoded by one of the ORFs of the present invention can be formulated using known techniques to generate a pharmaceutical composition.

5. EXAMPLES

Example 1

Isolation of SEQ ID NO: 1 from a cDNA Library of Human Cells

The novel nucleic acid of SEQ ID NO: 1 was obtained from a human cDNA library prepared from adult brain, using standard PCR, sequencing by hybridization sequence signature analysis, and Sanger sequencing techniques. The insert of the library was amplified with PCR using primers specific for vector sequences flanking the inserts. The sample was spotted onto nylon membranes and interrogated with oligonucleotide probes to give sequence signatures. The clones were clustered into a group of similar or identical sequences, and a single representative clone was selected for gel sequencing. The 5' sequence of the amplified insert was then deduced using the reverse M13 sequencing primer in a typical Sanger sequencing protocol. PCR products were purified and subjected to fluorescent dye terminator cycle sequencing. Single-pass gel sequencing was done using a 377 Applied Biosystems (ABI) sequencer. The insert of SEQ ID NO: 1 was described in co-owned international publication WO 03/029405.

Example 2

Assemblage of SEQ ID NO: 2

The nucleic acid encoding SCFA2 (SEQ ID NO: 2) was assembled from sequences that were obtained from a cDNA library by methods described in Example 1 above, and in some cases obtained from one or more public databases. The final sequence was assembled using the EST sequence as seed. Then a recursive algorithm was used to extend the seed into an extended assemblage, by pulling additional sequences from different databases (i.e. Hyseq's database containing EST sequences, dbEST version 124, gbpri 124, and UniGene version 124) that belong to this assemblage. The algorithm terminated when there were no additional sequences from the above databases that would extend the assemblage. Inclusion of component sequences into the assemblage was based on a BLASTN hit to the extending assemblage with BLAST score greater than 300 and percent identity greater than 95%.

Using PHRAP (Univ. of Washington) or CAP4 (Paracel), a full-length gene cDNA sequence and its corresponding protein sequence were generated from the assemblage. Any frame shifts and incorrect stop codons were corrected by hand editing. During editing, the sequence was checked using FASTY and BLAST against Genbank (i.e. dbEST version 124, gbpri 124, UniGene version 124, Genpept release 124). Other computer programs which may have been used in the editing process were phredPhrap and Consed (University of Washington) and ed-ready, ed-ext and cg-zip-2 (Hyseq, Inc.). The full-length nucleotide and amino acid sequences are shown in the Sequence Listing as SEQ ID NOS: 2 and 3, respectively. SEQ ID NO: 2 and 3 were described previously in co-owned international publication WO 03/029405.

Example 3

Cloning and Expression of SCFA2, SCFA4 and SCFA4v

In order to express SCFA2 polypeptide, the full-length SCFA2 DNA (SEQ ID NO: 2) was PCR amplified from a cDNA library that was constructed using human mRNA from cerebellum (Ambion). The sequence was also isolated from pools of cDNAs that were derived from human mRNAs from various tissues. The first round of PCR was performed using the forward primer (SEQ ID NO: 27) and reverse primer (SEQ ID NO: 28) 5'-GAGCAGCACAAAGGCTGCAC-3'. A second round of PCR was then performed using the primary PCR as template using the forward primer SEQ ID NO: 29 and reverse primer of SEQ ID NO: 30. The restriction sites NheI and XbaI, which are embedded in the forward and reverse primers (SEQ ID NO: 29 and 30) were used for subcloning of the NheI-XbaI fragment into the mammalian expression vector pIntron/Igκ. The NheI-XbaI fragment contains polynucleotide sequence (SEQ ID NO: 5) which encodes the amino acid sequence of SCFA2 that lacks the signal peptide (SEQ ID NO: 6) and stop codon. The mammalian expression vector pIntron/Igκ was obtained by genetically modifying the pSectag vector (Invitrogen Inc., Carlsbad, Calif.) by introducing an engineered chimeric intron derived from the pCI mammalian expression vector (Promega, Madison, Wis.) as follows. A fragment of the pCI vector containing the pCMV and intron sequence was excised from the pCI vector using BglII and NheI restriction enzymes, and subcloned into the pSectag vector, from which its sequence flanked by BglII and NheI had been removed.

cDNA encoding SCFA2ΔC was isolated from the cDNA pools described above using PCR. PCR was performed using the forward primer of SEQ ID NO: 52 and the reverse primer of SEQ ID NO: 53. The NheI and XbaI sites contained in the primers were used to subclone the NheI-XbaI fragment of SCFA2A into the mammalian expression vector pIntron/Igκ. The NheI-XbaI fragment of SCFA2ΔC contains the polynucleotide sequence (SEQ ID NO: 50) which encodes the amino acid sequence of SEQ ID NO: 51.

cDNAs encoding SCFA4 and SCFA4v were isolated from the cDNA pools described above using PCR. The first round of PCR was performed using the forward primer of SEQ ID NO: 31 and the reverse primer of SEQ ID NO: 32. Ethidium bromide staining of the agarose gels that were used to resolve the PCR products revealed that two distinct inserts had been amplified from each of the cDNA libraries. The sequence of each insert was determined. One insert contained the sequence that encodes SCFA4 (SEQ ID NO: 13), while the second insert contained a sequence that encodes a variant of SCFA4 (SEQ ID NO: 22), identified herein as SCFA4v.

A second round of PCR was performed using the primary PCR as a template and using the forward primer of SEQ ID NO: 33 and the reverse primer of SEQ ID NO: 34. The NheI and XbaI sites contained in the primers were used to subclone the NheI-XbaI fragment of SCFA4 and SCFA4v into the mammalian expression vector pIntron/Igκ. The NheI-XbaI fragment of SCFA4 contains the polynucleotide sequence (SEQ ID NO: 16), which encodes the amino acid sequence of SCFA4 that lacks the signal peptide (SEQ ID NO: 17) and the stop codon. The NheI-XbaI fragment of SCFA4v contains polynucleotide sequence (SEQ ID NO: 25), which encodes the amino acid sequence of SCFA4 that lacks the signal peptide (SEQ ID NO: 26) and the stop codon.

Example 4

The Adenoviral Vector

The polynucleotides encoding the dominant mature forms of SCFA2 (SEQ ID NO: 5), SCFA4 (SEQ ID NO: 16), and SCFA4v (SEQ ID NO: 25), as well as the C-terminal deletion of SCFA2, SCFA2ΔC (SEQ ID NO: 51) were amplified from the pIntron/Igκ vector together with the Igκ leader sequence and the V5His6 tag of the pIntron/Igκ vector, and cloned into the pAdenovator-CMVIntron adenoviral vector (SEQ ID NO: 47) as follows. The polynucleotide sequence (SEQ ID NO: 35) that encodes pIntron-SCFA2-V5His6 (SEQ ID NO: 36) was amplified from the pIntron/Igκ using the forward primer of SEQ ID NO: 37 and the reverse primer of SEQ ID NO: 38. The restriction enzyme sites XbaI and NotI that are contained in the primers were used to clone SEQ ID NO: 35 into the NheI and NotI sites of the pAdenovator-CMVIntron vector (SEQ ID NO: 47).

The polynucleotide sequence (SEQ ID NO: 39) that encodes pIntron-SCFA4-V5His6 (SEQ ID NO: 40) was amplified from the pIntron/Igκ using the forward primer of SEQ ID NO: 41 and the reverse primer of SEQ ID NO: 42. The restriction enzyme sites XbaI and NotI that are contained in the primers were used to clone SEQ ID NO: 39 into the NheI and NotI sites of the pAdenovator-CMVIntron vector (SEQ ID NO: 47).

The primers of SEQ ID NO: 40 and 41 were also used to amplify the polynucleotide sequence (SEQ ID NO: 43) that encodes pIntron-SCFA4v-V5His6 (SEQ ID NO: 44). SEQ ID NO: 43 was subcloned into the pAdenovator-CMVIntron vector using the XbaI and NotI sites, as described above.

The polynucleotide sequence (SEQ ID NO: 54) that encodes pIntron-SCFA2ΔC-V5His6 (SEQ ID NO: 55) was amplified from the pIntron/Igκ and cloned into the NheI and NotI sites of the pAdenovator-CMVIntron vector (SEQ ID NO: 47).

The adenoviral vector pAdenovator-CMVIntron was obtained by modifying the pAdenoVatorCMV5-IRES-GFP (Qbiogene, Carlsbad, Calif., U.S. as follows. pAdenoVator-CMV5-IRES-GFP was digested with SpeI to remove its MCS, IRES and GFP and ligated with PCR amplified Intron-MCS-V5His-BGH polyA from pcDNA/Intron vector using forward primer (SEQ ID NO: 45) and reverse primer (SEQ ID NO:46).

Transformation of linearized transfer vector into bacterial cells, BJ5183, (Qbiogene, Carlsbad, Calif., U.S.A) which carry AdEasy-1 plasmid that encode Adenovirus-5 genome (E1/E3 deleted) was performed by electroporation according to the manufacturer's instructions. Recombinant adenovirus was generated and amplified in QBI-293A cells (Qbiogene, Carlsbad, Calif., U.S.A) and purified by CsCl banding as previously described (Garnier, A., J. Cote et al. 1994). Recombinant protein expression by 293A cells that had been infected with the recombinant adenovirus was measured by Western analysis using anti-V5 antibody (Invitrogene Inc., Carlsbad, Calif.). The titer of CsCl purified recombinant viruses was measured using the Adeno-X rapid titer kit (BD Biosciences, Palo Alto, U.S.A.) according to the manufacturer's protocols. Briefly, a viral stock was tested by infecting 293A cells with serial dilutions of the recombinant adenovirus stock followed by fixation and staining of the transduced cells with mouse anti-hexon antibody 48 hours after infection. The signal was detected with a goat anti-mouse antibody conjugated to horseradish peroxidase and developed with metal-enhanced 3,3'-diaminobenzidine tetrahydro-chloride (DAB).

Example 5

Administration of Recombinant Adenovirus as a Model to Evaluate the Biological Activity of SCFA2, SCFA4, and SCFA4v The SCFA2, SCFA4, and SCFA4v recombinant adenovirus was administered to normal mice to determine the effect SCFA2, SCFA4, and SCFA4v on the intestinal and colonic epithelium. Prior to injection of adenovirus, BALB/c mice, 9-11 weeks of age, were anesthetized using isoflurane. $1 \times 10^{10}$ viral particles per mouse were injected via the retro-orbital vein. The same titer of control virus (empty virus) or PBS alone was used as controls. A totel of 46 mice were used in the study. Mice were sacrificed 3 days after receiving the virus injection. 4 hours before sacrifice, 1 mg of bromodeoxyuridine (BrdU) was injected intraperitoneally (IP) to determine in vivo proliferation of epithelial cells. Various tissues including small intestine, colon, spleen, liver and bone marrow were collected and fixed in formaline. Paraffin embedded sections were stained with hematoxyline and eosin (H&E) for histological evaluation. Sections were also processed for BrdU immunohistochemistry according to the manufacturer's instruction (Oncogene Research product, Boston, U.S.A.) as previously described (McKinley, J. N. et al. 2000). Immunohistochemistry using monoclonal rat anti-mouse Ki67 antigen (Dako Ltd., High Wycombe, UK) is also performed to assess the proliferation of intestinal epithelial cells according to the method previously described (Scholzen, T. et al. 2000).

H&E staining of sections from the small intestine that had been sacrificed 3 days following the adenovirus injection (FIG. 4) show that the small intestine of mice that had received the SCFA2, SCFA4, or SCFA4v adenovirus was significantly altered. The histological changes caused by SCFA2, SCFA4, and SCFA4v included a marked, diffuse thickening of the mucosa by crypt epithelial hyperplasia with a marked increased in crypt length and complexity of branching. In addition to the effect seen in the small intestine, SCFA2, SCFA4, and SCFA4v also induced crypt epithelial hyperplasia with a marked increased in crypt length and an increased number and size of Goblet cells in the colon.

To evaluate the effect of SCFA2, SCFA4, and SCFA4v on the proliferation of intestinal epithelial cells, BrdU incorporation was performed on sections from the small intestine and the colon of control mice and mice that had received SCFA2, SCFA4, and SCFA4v adenovirus. As shown in FIG. 5, the mice that had received the SCFA2, SCFA4, or SCFA4v adenovirus had small intestinal and colonic crypts that had significantly more BrdU positive cells, when compared to the small intestine from the control animals. Thus, SCFA2, SCFA4, and SCFA4v stimulate the proliferation of gastrointestinal epithelial cells.

Example 6

Prophylactic Effect of SCFA2, SCFA4 and SCFA4v on Radiation-Induced Mucositis

The efficacy of SCFA2, SCFA4 or SCFA4v as a prophylactic and therapeutic agent is tested in an animal model of radiation-induced mucositis.

Forty eight adult male BDF1 mice, aged 10-12 weeks, are used. On delivery from the supplier and prior to the experiment, the animals are housed for two weeks in individually ventilated cages on a 12 hour light:dark cycle to stabilize the circadian rhythm. Animals are allowed food and water ad libitum. The animals are divided into 8 groups of 6 animals, and treated as follows:
1. Injected with 2 mg/kg SCFA2, SCFA4 or SCFA4v iv at 72, 48, and 24 hours prior to being exposed to 13 Gy X-ray (whole body);
2. Injected with 5 mg/kg SCFA2, SCFA4 or SCFA4v iv at 72, 48, and 24 hours prior to being exposed to 13 Gy X-ray (whole body);
3. Injected with 125 µg KGF iv at 72, 48, and 24 hours prior to being exposed to 13 Gy X-ray (whole body);
4. Injected with saline vehicle iv at 72, 48, and 24 hours prior to being exposed to 13 Gy X-ray (whole body);
5. Untreated, non-irradiated controls;
6. Injected with 2 mg/kg SCFA2, SCFA4 or SCFA4v iv 24, 48, and 72 hours post irradiation with 13 Gy X-rays (whole body);
7. Injected with 5 mg/kg SCFA2, SCFA4 or SCFA4v iv 24, 48, and 72 hours post irradiation with 13 Gy X-rays (whole body);
8. Injected with saline iv at 24, 48, and 72 hours post irradiation with 13 Gy X-rays (whole body).

All injections are given at the same time of day. Intestinal damage is induced using a single dose of 13 Gy X-irradiation (delivered at 0.7 Gy/min) at 15:00.

Four days after irradiation the animals are sacrificed. The small intestine is removed and fixed in Carnoy's fixative prior to processing for histological analysis. Transverse sections 3 µm thick are cut and stained with haematoxylin and eosin (H&E).

Immediately after sacrifice, the duodenum, mid-colon, liver, lung, tongue, spleen, stomach and pancreas are also removed and fixed in formal saline overnight prior to storage in 70% ethanol.

For each animal, ten intestinal circumferences are analyzed (60 per group)—a circumference is equivalent to a given length of intestine and therefore a convenient baseline unit of length. The number of surviving crypts per circumference is scored and the average per group determined.

The average crypt width (measured at its widest point) is also measured in order to correct for scoring errors due to crypt size difference. The correction is applied thus:

$$\frac{\text{Corrected number of crypts}}{\text{circumference}} = \frac{\text{Mean crypt width in untreated control}}{\text{Mean crypt width in treated animal}} \times$$
$$\text{Mean number of surviving crypts in treatment group}$$

SCFA2, SCFA4 or SCFA4v can be administered to protect the epithelium of the small intestine from the injurious effects of irradiation, and can be used as potent prophylactics in patients for whom radiation therapy has been indicated.

Example 7

Prophylactic Effect of SCFA2, SCFA4 and SCFA4v on Chemotherapy-Induced Mucositis A. Normal Mice The efficacy of recombinant SCFA2 and SCFA2ΔC in treating chemotherapy-induced mucositis was evaluated in normal mice. The experimental protocol was based on that previously described by Boushey et al. (Cancer Res. 61:687-693 (2001)).

Female BDF-1 mice (11-13 weeks old) were used. The mice were divided into experimental groups of 13 mice each and treated as follows:
1. Negative control: vehicle (50% DMSO) injected ip from day 0 to day 3, saline injected iv daily from day −3 to day 6;
2. Mucositis control: 50 mg/kg 5-FU injected ip from day 0 to day 3, saline injected iv daily from day −3 to day 6;
3. 50 mg/kg 5-FU injected ip from day 0 to day 3, 50 µg SCFA2 in 100 µl saline injected daily from day −3 to day 6;
4. 50 mg/kg 5-FU injected ip from day 0 to day 3, 5 µg SCFA2 in 100 µl saline injected daily from day −3 to day 6;
5. 50 mg/kg 5-FU injected ip from day 0 to day 3, 50 µg SCFA2ΔC in 100 µg saline injected daily from day −3 to day 6;
6. 50 mg/kg 5-FU injected ip from day 0 to day 3, 5 µg SCFA2ΔC in 100 µg saline injected daily from day −3 to day 6.

Starting at day 0, the animals' body weight, severity of diarrhea, and mortality were recorded daily. A diarrhea score of 0 to 3 reflected a corresponding worsening of the symptom from 0 being normal to 3 being severe. The change in body weight was calculated as the percent body weight of that of the untreated group.

All animals were euthanized on day 6 and injected with 4 mg/0.1 ml BrdU two hours prior to sacrifice. The large and small intestine were removed and weighed, their length was measured, and the diameter of the mid-jejunum was recorded. A segment (1 cm) of the mid-jejunum was excised about 14-15 cm from the pylorus, and a segment (1 cm) of the transverse colon was excised at about 4 cm from the ileocaecal junction. The bowel segments were flushed and fixed using 10% neutral buffered formalin for histological analysis. Histological examination and morphometry of the mucosa were performed on tissue sections using the ImagePro Software (ImagePro, Ltd., Ashford, Middlesex, UK).

The effect of SCFA2 and SCFA2ΔC on body weight is summarized in Tables 1 and 2, respectively and FIG. 6.

TABLE 1

| 5-FU | Treatment | Chemotherapy toxicity | | |
|---|---|---|---|---|
| | | Maximum weight loss (%) | Mortality (%) | Survival time[#] (day) |
| Yes | Saline control | 22.4 ± 5.3 | 80 | 11.3 ± 1.4 |
| Yes | SCFA2 (50 μg) | 5.9 ± 7.8* | 20 | 10.5 ± 0.7 |
| Yes | SCFA2 (5 μg) | 18.5 ± 6.8 | 40 | 11.2 ± 1.9 |

*$P < 0.05$ (ANOVA, 5-FU/Saline vs. 5-FU/SCFA2).
[#]only animals found dead were calculated for survival time.

TABLE 2

| 5-FU | Treatment | Chemotherapy toxicity | | |
|---|---|---|---|---|
| | | Maximum weight loss (%) | Diarrhea score | Mortality (%) |
| Yes | Saline control | 15.4 ± 6.1 | 1.0 ± 0.0 | 60 |
| Yes | SCFA2ΔC (50 μg) | 11.2 ± 3.7 | 0.7 ± 0.5 | 0 |
| Yes | SCFA2ΔC (5 μg) | 15.2 ± 5.5 | 1.0 ± 0.5 | 30 |

*$P < 0.05$ (ANOVA, 5-FU/Saline vs. 5-FU/SCFA2).

SCFA2 and SCFA2ΔC significantly reduced the severity of the diarrhea and mortality caused by 5-FU-induced mucositis when compared to mice which did not receive SCFA2 or SCFA2ΔC. Similarly, SCFA2 and SCFA2ΔC reduced the loss of body weight that the 5-FU-treated animals experienced.

The effect of SCFA2 and SCFA2ΔC on the gross appearance of the intestines is shown in FIG. 7. The intestines of the mice treated with 5-FU were atrophied and numerous lesions associated with bleeding were observed while the appearance of the intestines from the mice that had received SCFA2 or SCFA2ΔC were overtly normal and accompanied by the typical distension due to the proliferative effect of SCFA2 and SCFA2ΔC on the intestinal epithelium.

Histological analysis of intestinal sections of the small intestine and colon of all experimental groups showed that SCFA2 and SCFA2ΔC preserved the intestinal architecture of the mice with 5-FU-induced mucositis by preventing the massive damage to the villi and crypt compartments of the intestinal mucosa caused by 5-FU (FIG. 8). Micromorphometry measurements of villus height and crypt depth in the mid-jejunum confirm that the effect of SCFA2 and SCFA2ΔC is significant (FIG. 9). The crypt proliferative index, which is calculated as the percent of crypt cells that stained positive for BrdU, was significantly greater in the 5-FU-treated mice that received SCFA2 or SCFA2ΔC than in those that received saline ($P<0.05$) (FIG. 10). Histological analysis of BrdU incorporation in both small intestine and colon of mice treated with SCFA2 and SCFA2ΔC is shown in FIGS. 11 and 12, respectively.

SCFA2 and SCFA2ΔC protect the small intestine and colon from the deleterious effects of 5-FU; therefore, SCFA2 and SCFA2ΔC can be used in conjunction with chemotherapeutic agents to reduce the deleterious side-effects of antineoplastic therapies.

B. Tumor-Bearing Mice

The efficacy of recombinant human SCFA2, SCFA4 or SCFA4v in treating chemotherapy-induced mucositis is evaluated in healthy and in tumor-bearing mice. The experimental protocol is based on that previously described by Boushey et al. (Cancer Res 61:687-693 (2001)).

One million CT26 murine colon carcinoma cells (ATCC, Manassas, Va., USA) are injected sc into syngeneic female BALB/c mice, and the tumors are allowed to develop for 5 days. Healthy and tumor-bearing animals are divided into experimental groups of 6 mice each and treated as follows:

1. tumor bearing mice, vehicle (50% DMSO) injected ip from day 1 to day 5, saline injected iv from day 0 to day 7 (TVS)
2. tumor bearing mice, vehicle (50% DMSO) injected ip from day 1 to day 5, 50 μg SCFA2, SCFA4 or SCFA4v in 100 μl saline injected iv daily from day 0 to day 7 (TVG);
3. tumor bearing mice, 50 mg/kg 5-FU injected ip from day 1 to day 5, saline injected iv from day 0 to day 7 (TDS);
4. tumor bearing mice, 50 mg/kg 5-FU injected ip from day 1 to day 5, 50 μg SCFA2, SCFA4 or SCFA4v in 100 μl saline injected iv from day 0 to day 7 (TDG);
5. healthy mice, 50 mg/kg 5-FU injected ip from day 1 to day 5, saline injected iv from day 0 to day 7 (NDS);
6. healthy mice, 50 mg/kg 5-FU injected ip from day 1 to day 5, 50 μg SCFA2, SCFA4 or SCFA4v in 100 μl saline injected iv from day 0 to day 7 (NDG).

On days 0, 2, 4, 6, and 8 measurements of animal body weight, severity of diarrhea, and size of the tumors are recorded. A diarrhea score of 0-3 reflects a corresponding worsening of the symptom from 0 being normal to 3 being severe. The change in body weight is calculated as the percent body weight of that of the untreated group. The length, width and height of the tumor are measured with calipers, and the volume of the tumor is calculated as (length×width×height)/2.

All animals are euthanized on day 8. The large and small intestine are removed and weighed, their length is measured, and the diameter of the mid-jejunum is recorded. A segment (1 cm) of the mid-jejunum is excised about 14-15 cm from the pylorus, and a segment (1 cm) of the transverse colon is excised at about 4 cm from the ileocaecal junction. The bowel segments are flushed and fixed using 10% neutral buffered formalin for histological analysis. Histological examination and morphometry of the mucosa were performed on tissue sections using the ImagePro Software (Imagepro, Ltd., Ashford, Middlesex, UK).

SCFA2, SCFA4 or SCFA4v can be used in conjunction with chemotherapeutic agents to reduce the deleterious side-effects of antineoplastic therapies.

Example 8

Prophylactic Effect of SCFA2, SCFA4 and SCFA4v on Chemotherapy and Radiation-Induced Oral Mucositis A. Radiation-Induced Oral Mucositis The effect of SCFA2, SCFA4 and SCFA4v on the proliferation of the dorsal (buccal) and ventral epithelium of the tongue is studied in mice that are subjected to X-ray irradiation.

Immunohistochemistry using monoclonal rat anti-mouse Ki67 antigen (Dako Ltd., High Wycombe, UK) is performed, according to manufacturer's instruction and the method previously described (Scholzen, T. et al. 2000), on paraffin embedded sections of tongue from non-irradiated and irradiated mice (groups 1, 2, and 3 in Example 7B).

The epithelial proliferative index, which is calculated as the percent epithelial cells that stain positive for Ki67, is calculated to confirm that SCFA2, SCFA4 or SCFA4v reduces the loss of cellularity that is typically caused by radiation to the ventral tongue epithelium.

B. Chemotherapy-Induced Oral Mucositis

Histological analysis of sections from the tongue of animals that were treated with 5-FU (groups 3-6 in Example 7A) showed that SCFA2 and SCFAΔC maintained the morphology of the tongue epithelial layers in normal BDF-1 mice that were treated with 5-FU (FIG. 13). Micromorphometry measurements of the number of basal layer epithelial cells (FIG. 14) and mucosal thickness (FIG. 15) confirmed that the effect of SCFA2 and SCFA2ΔC is significant. The basal layer BrdU proliferative index, which is calculated as the percent of basal layer epithelial cells that stained positive for BrdU, was significantly greater in the 5-FU-treated mice that received SCFA2 or SCFA2ΔC than in those that received saline ($P<0.05$) (FIG. 16).

Therefore, SCFA2, SCFA2ΔC, SCFA4 or SCFA4v may be used as a therapeutic agent for the treatment and/or prevention of chemotherapy and radiation therapy-induced oral mucositis.

Quantitative animal models of oral mucositis (e.g. Wardly et al., Arch Oral Biol 43:567-577 (1998); Potten et al., Cell Prolif 35:32-47 (2002)) can be used to study further the therapeutic properties of SCFA2, SCFA4 or SCFA4v, when administered in combination with other cytotoxic agent to further assess the potential role of SCFA2, SCFA4 or SCFA4v in reducing the severity of the cellular depletion and to increase the rate of regeneration of the epithelial layers of the oral and intestinal epithelium.

Example 9

Therapeutic Effect of SCFA2, SCFA4 and SCFA4v on Dextran Sulfate Sodium-Induced Colitis The efficacy of recombinant human SCFA2, SCFA4 or SCFA4v in treating colitis is tested in a mouse model of dextran sulfate sodium (DSS)-induced colitis, and compared to the efficacy of GLP-2 (L'Heureux and Brubaker J Pharmacol Exp Ther 306:347-354 (2003); Kriegelstein et al., J Clin Invest 110:1773-1782 (2002); Siegmund et al., J Pharmacol Exp Ther 296:99-105 (2001)).

Six to eight-week old female BALB/c mice (Charles River Laboratories, Wilmington, Mass., USA) are housed in ventilated cages and acclimated for one week to a 12 hour light:dark cycle. Twenty four mice having similar body weight (approximately 20 g; <5% variance) are housed in 4 cages and fed ad libitum a 4% DSS (v/w) drinking solution for 7 days.

On day 7, the body weight of each animal is recorded, and the scores for loss in body weight, the consistency of stools, and anal bleeding are determined as shown in the Table below.

TABLE 3

| SCORE | Weight Loss (%) | Stool Consistency | Occult/Gross Rectal bleeding |
| --- | --- | --- | --- |
| 0 | None | Normal | Normal |
| 1 | 0-5% | | |
| 2 | 5-10% | Loose | Hemoccult |
| 3 | 10-20% | | |
| 4 | >20% | Diarrhea | Gross |

The scores are used to calculate the IBD activity index (IBDAI), which is used as an indicator of the severity of the colitis, and is calculated as the average of the scores given for the tabulated parameters. The scores for weight loss, stool consistency, and rectal bleeding are determined daily, and the IBDAI is recorded daily for the duration of the experiment.

On day 7, the 4% (v/w) DSS drinking solution is substituted with a 1% (v/w) DSS solution to maintain the disease activity without exacerbating the effect of the DSS. Sixteen of the DSS-fed animals are selected for consistent and comparable disease activity, and are dived into groups of 4 animals and are treated as follows:

1. Water, saline injected iv daily (10 am) for 7 days
2. DSS (1%) for 7 days, saline injected iv daily (10 am) for 7 days
3. DSS (1%) for 7 days, 100 μg SCFA2, SCFA4 or SCFA4v injected daily iv (10 am) for 7 days
4. DSS (1%) for 7 days, 50 μg SCFA2, SCFA4 or SCFA4v injected daily iv (10 am) for 7 days
5. DSS (1%) for 7 days, 10 μg GLP-2 injected sc twice daily (10 am and 6 pm) for 7 days.

On day 14, food is removed from the cages to allow for purging of the intestine, and the animals are sacrifices by cervical dislocation. All animals are injected with 4 mg/0.1 ml BrdU two hours prior to sacrifice. The large and small intestine are removed and weighed, their lengths are measured, and the diameter of the mid-jejunum is recorded. A segment (1 cm) of the mid-jejunum is excised about 14-15 cm from the pylorus, and a segment (1 cm) of the transverse colon is excised at about 4 cm from the ileocaecal junction. The bowel segments are flushed and fixed using 10% neutral buffered formalin for histological analysis. Histological examination and morphometry of the mucosa is performed on tissue sections using the ImagePro Software (Imagepro, Ltd., Ashford, Middlesex, UK). The IBDIAs for the mice of experimental groups 2-5, and the corresponding scores for weight loss, stool consistency and rectal bleeding are determined. Animals receiving DSS with saline develop severe colitis that is typically associated with atrophy, hyperemia, and diarrhea when compared to the control group. While DSS causes disintegration of the villus and crypt compartments of the mucosa of the small intestine and colon, SCFA2, SCFA4 or SCFA4v can be used to reverse the effects caused by DSS, and restore the intestinal architecture of the crypts and villi.

Example 10

Therapeutic Effect of SCFA2, SCFA4 or SCFA4v Following Massive Intestinal Resection The effect of SCFA2, SCFA4 and SCFA4v in augmenting the adaptive response to massive intestinal resection is tested in a rat animal model of short bowel syndrome. The animal model used in the study of the effects of enterorophic agents has been described (Scott et al. Am J Physiol G911-G921 (1998); Helmrath et al., J Am Coll Surg 183:441-449 (1996)), and the experimental protocol is herein incorporated by reference).

The animals are divided into a resected group that will have a 75% surgical resection of the midjejunuoileum, a sham-resected operated control group in which the intestine is sectioned and reanastomosed, and an unoperated control group. The animals are administered saline or SCFA2, SCFA4 and SCFA4v at a dose of 2 mg/Kg. The 75% intestinal resection is chosen to maximize any adaptive response and retention of equal portions of the proximal jejunum and distal ileum is based on the nutritional implications of removing the specialized absorptive capacity of the terminal ileum for vitamin B12 and bile acids and the ileal brake. In the rat, the retention of 25% of the small intestine inclusive of a portion of distal ileum, is sufficient to allow resected animals to achieve the same growth rate as control animals.

The morphological and functional response of the gut to resection and treatment with SCFA2, SCFA4 and SCFA4v is assessed at 6, 14, and 21 days. Food intake and growth, gross and microscopic small intestinal morphology and functional evaluation of mucosal absorptive characteristics are evaluated as described (Scott et al., supra).

Example 11

Effect of SCFA2, SCFA4 and SCFA4v on TNBS-Induced Colitis

The hapten agent 2,4,6-trinitrobenzenesulfonic acid (TNBS) induces a chronic colitis that is characterized by severe, transmural inflammation associated with diarrhea, rectal prolapse, and weight loss. These clinical and histopathological features indicate that TNBS-induced colitis mimics important characteristics of human Crohns disease (Neurath et al., J Exp Med 182:1281-1290 (1995)).

The therapeutic effect of SCFA2, SCFA4 and SCFA4v is tested in mice with TNBS-induced colitis. Intestinal inflammation is induced in 6-8 week-old female BALBc mice (group I) by a single rectal administration of 1 mg TNBS, as described by Neurath et al, supra). The control animal group (Group II) receive rectal administration of vehicle alone (45% ethanol). The mice are sacrificed after 7 days, and the induction of colitis by TNBS is assessed. The TNBS-treated mice suffer from severe diarrhea, and ulceration and bleeding accompanies the atrophy of the colon of the TNBS animals. No deleterious effects are noted.

Histologic changes are evaluated in H&E stained paraffin-embedded sections of the colon from the control and TNBS groups. TNBS induces thickening of the colon wall and substantial transmural leukocytic infiltration into the lamina propria The therapeutic effect of SCFA2, SCFA4 and SCFA4v is tested in the TNBS-treated animals by administering daily doses of up to 4 mg/Kg (100 µg/mouse; iv), beginning at day 3 following administration of TNBS (group II). Animals from each group are sacrificed at day 7 or day 10. The tissues are removed, and histological evaluation, morphometric analysis, and proliferative and apoptotic indices are determined, as described in the examples above.

We claim:

1. An isolated polynucleotide comprising the nucleotide sequence of SEQ ID NO: 22.

2. The polynucleotide of claim 1 which is a DNA sequence.

3. An isolated polynucleotide which comprises the complement of the polynucleotide of claim 1.

4. A vector comprising the polynucleotide of claim 1.

5. An expression vector comprising the polynucleotide of claim 1.

6. A host cell genetically engineered to comprise the polynucleotide of claim 1.

7. A method of producing a recombinant polypeptide comprising:
   (a) culturing the host cell or claim 6, under conditions sufficient to express the polypeptide in said cell; and
   (b) isolating the polypeptide from the cell culture or cells of step (a).

8. A host cell genetically engineered to comprise the polynucleotide of claim 1 operatively associated with a regulatory sequence that modulates expression of the polynucleotide in the host cell.

9. An isolated polynucleotide encoding a polypeptide with biological activity, said polynucleotide having greater than 95% sequence identity with the polynucleotide of SEQ ID NO: 22.

10. An adenoviral vector comprising a gene encoding SEQ ID NO: 23 operably associated with an expression control sequence.

11. A transgene construct comprising a nucleic acid encoding the polypeptide of SEQ ID NO: 23.

\* \* \* \* \*

SEQUENCE LISTING

<160> NUMBER OF SEQ ID NOS: 55

<210> SEQ ID NO 1
<211> LENGTH: 427
<212> TYPE: DNA
<213> ORGANISM: Homo sapiens

<400> SEQUENCE: 1

```
tttcgtggcg agtctccctc tgagtcctcc ccagcagcgc ggccggcgcc ggctctttgg      60
gcgaaccctc cagttcctag actttgagag gcgtctctcc cccgcccgac cgcccagatg     120
cagtttcgcc ttttctcctt tgccctcatc attctgaact gcatggatta cagccactgc     180
caaggcaacc gatggagacg cagtaagcga ggtgggtcct tctctgccaa agctagttat     240
gtatcaaatc ccatttgcaa gggttgtttg tcttgttcaa aggacaatgg gtgtagccga     300
tgtcaacaga agttgttctt cttccttcga agagaaggga tgcgccagta tggagagtgc     360
ctgcattcct gcccatccgg gtactatgga caccgagccc cagatatgaa cagatgtgca     420
agatgca                                                               427
```

<210> SEQ ID NO 2
<211> LENGTH: 1356
<212> TYPE: DNA
<213> ORGANISM: Homo sapiens

```
<220> FEATURE:
<221> NAME/KEY: CDS
<222> LOCATION: (262)..(993)

<400> SEQUENCE: 2
cccagcccac gtgctaacca agcggctcgc ttcccgagcc cgggatggag caccgcgcct      60
agggaggccg cgccgcccga cacgtgcgca cggttcgtgg cggagagatg ctgatcgcgc     120
tgaactgacc ggtgcggccc gggggtgagt ggcgagtctc cctctgagtc ctccccagca     180
gcgcggccgg cgccggctct ttgggcgaac cctccagttc ctagactttg agaggcgtct     240
ctcccccgcc cgaccgccca g atg cag ttt cgc ctt ttc tcc ttt gcc ctc       291
                        Met Gln Phe Arg Leu Phe Ser Phe Ala Leu
                         1               5                  10 atc att ctg aac tgc atg gat tac agc cac tgc caa ggc aac cga tgg       339
Ile Ile Leu Asn Cys Met Asp Tyr Ser His Cys Gln Gly Asn Arg Trp
             15                  20                  25 aga cgc agt aag cga gct agt tat gta tca aat ccc att tgc aag ggt       387
Arg Arg Ser Lys Arg Ala Ser Tyr Val Ser Asn Pro Ile Cys Lys Gly
         30                  35                  40 tgt ttg tct tgt tca aag gac aat ggg tgt agc cga tgt caa cag aag       435
Cys Leu Ser Cys Ser Lys Asp Asn Gly Cys Ser Arg Cys Gln Gln Lys
     45                  50                  55 ttg ttc ttc ttc ctt cga aga gaa ggg atg cgc cag tat gga gag tgc       483
Leu Phe Phe Phe Leu Arg Arg Glu Gly Met Arg Gln Tyr Gly Glu Cys
 60                  65                  70 ctg cat tcc tgc cca tcc ggg tac tat gga cac cga gcc cca gat atg       531
Leu His Ser Cys Pro Ser Gly Tyr Tyr Gly His Arg Ala Pro Asp Met
75                  80                  85                  90 aac aga tgt gca aga tgc aga ata gaa aac tgt gat tct tgc ttt agc       579
Asn Arg Cys Ala Arg Cys Arg Ile Glu Asn Cys Asp Ser Cys Phe Ser
                 95                 100                 105 aaa gac ttt tgt acc aag tgc aaa gta ggc ttt tat ttg cat aga ggc       627
Lys Asp Phe Cys Thr Lys Cys Lys Val Gly Phe Tyr Leu His Arg Gly
            110                 115                 120 cgt tgc ttt gat gaa tgt cca gat ggt ttt gca cca tta gaa gaa acc       675
Arg Cys Phe Asp Glu Cys Pro Asp Gly Phe Ala Pro Leu Glu Glu Thr
        125                 130                 135 atg gaa tgt gtg gaa gga tgt gaa gtt ggt cat tgg agc gaa tgg gga       723
Met Glu Cys Val Glu Gly Cys Glu Val Gly His Trp Ser Glu Trp Gly
    140                 145                 150 act tgt agc aga aat aat cgc aca tgt gga ttt aaa tgg ggt ctg gaa       771
Thr Cys Ser Arg Asn Asn Arg Thr Cys Gly Phe Lys Trp Gly Leu Glu
155                 160                 165                 170 acc aga aca cgg caa att gtt aaa aag cca gtg aaa gac aca ata ccg       819
Thr Arg Thr Arg Gln Ile Val Lys Lys Pro Val Lys Asp Thr Ile Pro
                175                 180                 185 tgt cca acc att gct gaa tcc agg aga tgc aag atg aca atg agg cat       867
Cys Pro Thr Ile Ala Glu Ser Arg Arg Cys Lys Met Thr Met Arg His
            190                 195                 200 tgt cca gga ggg aag aga aca cca aag gcg aag gag aag agg aac aag       915
Cys Pro Gly Gly Lys Arg Thr Pro Lys Ala Lys Glu Lys Arg Asn Lys
        205                 210                 215 aaa aag aaa agg aag ctg ata gaa agg gcc cag gag caa cac agc gtc       963
Lys Lys Lys Arg Lys Leu Ile Glu Arg Ala Gln Glu Gln His Ser Val
    220                 225                 230 ttc cta gct aca gac aga gct aac caa taa aacaagagat ccggtagatt         1013
Phe Leu Ala Thr Asp Arg Ala Asn Gln
235                 240 tttagggggtt tttgtttttg caaatgtgca caaagctact ctccactcct gcacactggg    1073
```

```
gtgcagcctt tgtgctgctc tgcccagtat ctgttcccag taacatggtg aaaggaagca    1133
ccaccaggca tgcccctgtg ttatttatgc tttgatttga atctggagac tgtgaaggca    1193
ggagtaagtg cacagccccg tgacttggct cagtgtgtgc tgagagaatc cgtcccccgc    1253
accatggaca tgctagaggt gtgaggctgc agaacaccgc tggaggacgg acttgtgcct    1313
atttatgtga agaagatgc ttggcaggca atccgcgtgt att              1356
```

<210> SEQ ID NO 3
<211> LENGTH: 243
<212> TYPE: PRT
<213> ORGANISM: Homo sapiens

<400> SEQUENCE: 3

```
Met Gln Phe Arg Leu Phe Ser Phe Ala Leu Ile Ile Leu Asn Cys Met
1               5                   10                  15

Asp Tyr Ser His Cys Gln Gly Asn Arg Trp Arg Ser Lys Arg Ala
            20                  25                  30

Ser Tyr Val Ser Asn Pro Ile Cys Lys Gly Cys Leu Ser Cys Ser Lys
        35                  40                  45

Asp Asn Gly Cys Ser Arg Cys Gln Gln Lys Leu Phe Phe Leu Arg
    50                  55                  60

Arg Glu Gly Met Arg Gln Tyr Gly Glu Cys Leu His Ser Cys Pro Ser
65                  70                  75                  80

Gly Tyr Tyr Gly His Arg Ala Pro Asp Met Asn Arg Cys Ala Arg Cys
                85                  90                  95

Arg Ile Glu Asn Cys Asp Ser Cys Phe Ser Lys Asp Phe Cys Thr Lys
            100                 105                 110

Cys Lys Val Gly Phe Tyr Leu His Arg Gly Arg Cys Phe Asp Glu Cys
        115                 120                 125

Pro Asp Gly Phe Ala Pro Leu Glu Glu Thr Met Glu Cys Val Glu Gly
    130                 135                 140

Cys Glu Val Gly His Trp Ser Glu Trp Gly Thr Cys Ser Arg Asn Asn
145                 150                 155                 160

Arg Thr Cys Gly Phe Lys Trp Gly Leu Glu Thr Arg Thr Arg Gln Ile
                165                 170                 175

Val Lys Lys Pro Val Lys Asp Thr Ile Pro Cys Pro Thr Ile Ala Glu
            180                 185                 190

Ser Arg Arg Cys Lys Met Thr Met Arg His Cys Pro Gly Gly Lys Arg
        195                 200                 205

Thr Pro Lys Ala Lys Glu Lys Arg Asn Lys Lys Lys Arg Lys Leu
    210                 215                 220

Ile Glu Arg Ala Gln Glu Gln His Ser Val Phe Leu Ala Thr Asp Arg
225                 230                 235                 240

Ala Asn Gln
```

<210> SEQ ID NO 4
<211> LENGTH: 729
<212> TYPE: DNA
<213> ORGANISM: Homo sapiens

<400> SEQUENCE: 4

```
atgcagtttc gcctttctc ctttgccctc atcattctga actgcatgga ttacagccac    60
tgccaaggca accgtggag acgcagtaag cgagctagtt atgtatcaaa tcccatttgc    120
aagggttgtt tgtcttgttc aaaggacaat gggtgtagcc gatgtcaaca gaagttgttc    180
```

```
ttcttccttc gaagagaagg gatgcgccag tatggagagt gcctgcattc ctgcccatcc      240
gggtactatg gacaccgagc cccagatatg aacagatgtg caagatgcag aatagaaaac      300
tgtgattctt gctttagcaa agacttttgt accaagtgca aagtaggctt ttatttgcat      360
agaggccgtt gctttgatga atgtccagat ggttttgcac cattagaaga aaccatggaa      420
tgtgtggaag atgtgaagt tggtcattgg agcgaatggg gaacttgtag cagaaataat       480
cgcacatgtg gatttaaatg gggtctggaa accagaacac ggcaaattgt aaaaagcca       540 gtgaaagaca caataccgtg tccaaccatt gctgaatcca ggagatgcaa gatgacaatg      600
aggcattgtc caggagggaa gagaacacca aaggcgaagg agaagaggaa caagaaaaag      660
aaaaggaagc tgatagaaag ggcccaggag caacacagcg tcttcctagc tacagacaga      720
gctaaccaa                                                              729
```

```
<210> SEQ ID NO 5
<211> LENGTH: 669
<212> TYPE: DNA
<213> ORGANISM: Homo sapiens
<220> FEATURE:
<221> NAME/KEY: CDS
<222> LOCATION: (1)..(669)

<400> SEQUENCE: 5 caa ggc aac cga tgg aga cgc agt aag cga gct agt tat gta tca aat         48
Gln Gly Asn Arg Trp Arg Arg Ser Lys Arg Ala Ser Tyr Val Ser Asn
1               5                   10                  15 ccc att tgc aag ggt tgt ttg tct tgt tca aag gac aat ggg tgt agc         96
Pro Ile Cys Lys Gly Cys Leu Ser Cys Ser Lys Asp Asn Gly Cys Ser
            20                  25                  30 cga tgt caa cag aag ttg ttc ttc ttc ctt cga aga gaa ggg atg cgc        144
Arg Cys Gln Gln Lys Leu Phe Phe Phe Leu Arg Arg Glu Gly Met Arg
        35                  40                  45 cag tat gga gag tgc ctg cat tcc tgc cca tcc ggg tac tat gga cac        192
Gln Tyr Gly Glu Cys Leu His Ser Cys Pro Ser Gly Tyr Tyr Gly His
    50                  55                  60 cga gcc cca gat atg aac aga tgt gca aga tgc aga ata gaa aac tgt        240
Arg Ala Pro Asp Met Asn Arg Cys Ala Arg Cys Arg Ile Glu Asn Cys
65                  70                  75                  80 gat tct tgc ttt agc aaa gac ttt tgt acc aag tgc aaa gta ggc ttt        288
Asp Ser Cys Phe Ser Lys Asp Phe Cys Thr Lys Cys Lys Val Gly Phe
                85                  90                  95 tat ttg cat aga ggc cgt tgc ttt gat gaa tgt cca gat ggt ttt gca        336
Tyr Leu His Arg Gly Arg Cys Phe Asp Glu Cys Pro Asp Gly Phe Ala
            100                 105                 110 cca tta gaa gaa acc atg gaa tgt gtg gaa gga tgt gaa gtt ggt cat        384
Pro Leu Glu Glu Thr Met Glu Cys Val Glu Gly Cys Glu Val Gly His
        115                 120                 125 tgg agc gaa tgg gga act tgt agc aga aat aat cgc aca tgt gga ttt        432
Trp Ser Glu Trp Gly Thr Cys Ser Arg Asn Asn Arg Thr Cys Gly Phe
    130                 135                 140 aaa tgg ggt ctg gaa acc aga aca cgg caa att gtt aaa aag cca gtg        480
Lys Trp Gly Leu Glu Thr Arg Thr Arg Gln Ile Val Lys Lys Pro Val
145                 150                 155                 160 aaa gac aca ata ccg tgt cca acc att gct gaa tcc agg aga tgc aag        528
Lys Asp Thr Ile Pro Cys Pro Thr Ile Ala Glu Ser Arg Arg Cys Lys
                165                 170                 175 atg aca atg agg cat tgt cca gga ggg aag aga aca cca aag gcg aag        576
Met Thr Met Arg His Cys Pro Gly Gly Lys Arg Thr Pro Lys Ala Lys
            180                 185                 190
```

```
gag aag agg aac aag aaa aag aaa agg aag ctg ata gaa agg gcc cag       624
Glu Lys Arg Asn Lys Lys Lys Arg Lys Leu Ile Glu Arg Ala Gln
        195                 200                 205 gag caa cac agc gtc ttc cta gct aca gac aga gct aac caa taa           669
Glu Gln His Ser Val Phe Leu Ala Thr Asp Arg Ala Asn Gln
    210                 215                 220

<210> SEQ ID NO 6
<211> LENGTH: 222
<212> TYPE: PRT
<213> ORGANISM: Homo sapiens

<400> SEQUENCE: 6

Gln Gly Asn Arg Trp Arg Arg Ser Lys Arg Ala Ser Tyr Val Ser Asn
1               5                   10                  15

Pro Ile Cys Lys Gly Cys Leu Ser Cys Ser Lys Asp Asn Gly Cys Ser
                20                  25                  30

Arg Cys Gln Gln Lys Leu Phe Phe Phe Leu Arg Arg Glu Gly Met Arg
            35                  40                  45

Gln Tyr Gly Glu Cys Leu His Ser Cys Pro Ser Gly Tyr Tyr Gly His
        50                  55                  60

Arg Ala Pro Asp Met Asn Arg Cys Ala Arg Cys Arg Ile Glu Asn Cys
65                  70                  75                  80

Asp Ser Cys Phe Ser Lys Asp Phe Cys Thr Lys Cys Lys Val Gly Phe
                85                  90                  95

Tyr Leu His Arg Gly Arg Cys Phe Asp Glu Cys Pro Asp Gly Phe Ala
            100                 105                 110

Pro Leu Glu Glu Thr Met Glu Cys Val Glu Gly Cys Glu Val Gly His
        115                 120                 125

Trp Ser Glu Trp Gly Thr Cys Ser Arg Asn Asn Arg Thr Cys Gly Phe
    130                 135                 140

Lys Trp Gly Leu Glu Thr Arg Thr Arg Gln Ile Val Lys Lys Pro Val
145                 150                 155                 160

Lys Asp Thr Ile Pro Cys Pro Thr Ile Ala Glu Ser Arg Arg Cys Lys
                165                 170                 175

Met Thr Met Arg His Cys Pro Gly Gly Lys Arg Thr Pro Lys Ala Lys
            180                 185                 190

Glu Lys Arg Asn Lys Lys Lys Arg Lys Leu Ile Glu Arg Ala Gln
        195                 200                 205

Glu Gln His Ser Val Phe Leu Ala Thr Asp Arg Ala Asn Gln
    210                 215                 220

<210> SEQ ID NO 7
<211> LENGTH: 639
<212> TYPE: DNA
<213> ORGANISM: Homo sapiens
<220> FEATURE:
<221> NAME/KEY: CDS
<222> LOCATION: (1)..(639)

<400> SEQUENCE: 7 gct agt tat gta tca aat ccc att tgc aag ggt tgt ttg tct tgt tca       48
Ala Ser Tyr Val Ser Asn Pro Ile Cys Lys Gly Cys Leu Ser Cys Ser
1               5                   10                  15 aag gac aat ggg tgt agc cga tgt caa cag aag ttg ttc ttc ttc ctt       96
Lys Asp Asn Gly Cys Ser Arg Cys Gln Gln Lys Leu Phe Phe Phe Leu
                20                  25                  30 cga aga gaa ggg atg cgc cag tat gga gag tgc ctg cat tcc tgc cca      144
```

```
Arg Arg Glu Gly Met Arg Gln Tyr Gly Glu Cys Leu His Ser Cys Pro
        35                  40                  45 tcc ggg tac tat gga cac cga gcc cca gat atg aac aga tgt gca aga      192
Ser Gly Tyr Tyr Gly His Arg Ala Pro Asp Met Asn Arg Cys Ala Arg
 50                  55                  60 tgc aga ata gaa aac tgt gat tct tgc ttt agc aaa gac ttt tgt acc      240
Cys Arg Ile Glu Asn Cys Asp Ser Cys Phe Ser Lys Asp Phe Cys Thr
65                  70                  75                  80 aag tgc aaa gta ggc ttt tat ttg cat aga ggc cgt tgc ttt gat gaa      288
Lys Cys Lys Val Gly Phe Tyr Leu His Arg Gly Arg Cys Phe Asp Glu
                 85                  90                  95 tgt cca gat ggt ttt gca cca tta gaa gaa acc atg gaa tgt gtg gaa      336
Cys Pro Asp Gly Phe Ala Pro Leu Glu Glu Thr Met Glu Cys Val Glu
            100                 105                 110 gga tgt gaa gtt ggt cat tgg agc gaa tgg gga act tgt agc aga aat      384
Gly Cys Glu Val Gly His Trp Ser Glu Trp Gly Thr Cys Ser Arg Asn
        115                 120                 125 aat cgc aca tgt gga ttt aaa tgg ggt ctg gaa acc aga aca cgg caa      432
Asn Arg Thr Cys Gly Phe Lys Trp Gly Leu Glu Thr Arg Thr Arg Gln
    130                 135                 140 att gtt aaa aag cca gtg aaa gac aca ata ccg tgt cca acc att gct      480
Ile Val Lys Lys Pro Val Lys Asp Thr Ile Pro Cys Pro Thr Ile Ala
145                 150                 155                 160 gaa tcc agg aga tgc aag atg aca atg agg cat tgt cca gga ggg aag      528
Glu Ser Arg Arg Cys Lys Met Thr Met Arg His Cys Pro Gly Gly Lys
                165                 170                 175 aga aca cca aag gcg aag gag aag agg aac aag aaa aag agg aag          576
Arg Thr Pro Lys Ala Lys Glu Lys Arg Asn Lys Lys Lys Arg Lys
            180                 185                 190 ctg ata gaa agg gcc cag gag caa cac agc gtc ttc cta gct aca gac      624
Leu Ile Glu Arg Ala Gln Glu Gln His Ser Val Phe Leu Ala Thr Asp
        195                 200                 205 aga gct aac caa taa                                                   639
Arg Ala Asn Gln
    210

<210> SEQ ID NO 8
<211> LENGTH: 212
<212> TYPE: PRT
<213> ORGANISM: Homo sapiens

<400> SEQUENCE: 8

Ala Ser Tyr Val Ser Asn Pro Ile Cys Lys Gly Cys Leu Ser Cys Ser
1               5                   10                  15

Lys Asp Asn Gly Cys Ser Arg Cys Gln Gln Lys Leu Phe Phe Phe Leu
            20                  25                  30

Arg Arg Glu Gly Met Arg Gln Tyr Gly Glu Cys Leu His Ser Cys Pro
        35                  40                  45

Ser Gly Tyr Tyr Gly His Arg Ala Pro Asp Met Asn Arg Cys Ala Arg
 50                  55                  60

Cys Arg Ile Glu Asn Cys Asp Ser Cys Phe Ser Lys Asp Phe Cys Thr
65                  70                  75                  80

Lys Cys Lys Val Gly Phe Tyr Leu His Arg Gly Arg Cys Phe Asp Glu
                 85                  90                  95

Cys Pro Asp Gly Phe Ala Pro Leu Glu Glu Thr Met Glu Cys Val Glu
            100                 105                 110

Gly Cys Glu Val Gly His Trp Ser Glu Trp Gly Thr Cys Ser Arg Asn
        115                 120                 125
```

```
Asn Arg Thr Cys Gly Phe Lys Trp Gly Leu Glu Thr Arg Thr Arg Gln
    130                 135                 140

Ile Val Lys Lys Pro Val Lys Asp Thr Ile Pro Cys Pro Thr Ile Ala
145                 150                 155                 160

Glu Ser Arg Arg Cys Lys Met Thr Met Arg His Cys Pro Gly Gly Lys
                165                 170                 175

Arg Thr Pro Lys Ala Lys Glu Lys Arg Asn Lys Lys Lys Arg Lys
            180                 185                 190

Leu Ile Glu Arg Ala Gln Glu Gln His Ser Val Phe Leu Ala Thr Asp
        195                 200                 205

Arg Ala Asn Gln
    210

<210> SEQ ID NO 9
<211> LENGTH: 282
<212> TYPE: DNA
<213> ORGANISM: Homo sapiens
<220> FEATURE:
<221> NAME/KEY: CDS
<222> LOCATION: (1)..(282)

<400> SEQUENCE: 9 att tgc aag ggt tgt ttg tct tgt tca aag gac aat ggg tgt agc cga    48
Ile Cys Lys Gly Cys Leu Ser Cys Ser Lys Asp Asn Gly Cys Ser Arg
1               5                   10                  15 tgt caa cag aag ttg ttc ttc ttc ctt cga aga gaa ggg atg cgc cag    96
Cys Gln Gln Lys Leu Phe Phe Phe Leu Arg Arg Glu Gly Met Arg Gln
            20                  25                  30 tat gga gag tgc ctg cat tcc tgc cca tcc ggg tac tat gga cac cga   144
Tyr Gly Glu Cys Leu His Ser Cys Pro Ser Gly Tyr Tyr Gly His Arg
        35                  40                  45 gcc cca gat atg aac aga tgt gca aga tgc aga ata gaa aac tgt gat   192
Ala Pro Asp Met Asn Arg Cys Ala Arg Cys Arg Ile Glu Asn Cys Asp
    50                  55                  60 tct tgc ttt agc aaa gac ttt tgt acc aag tgc aaa gta ggc ttt tat   240
Ser Cys Phe Ser Lys Asp Phe Cys Thr Lys Cys Lys Val Gly Phe Tyr
65                  70                  75                  80 ttg cat aga ggc cgt tgc ttt gat gaa tgt cca gat ggt ttt             282
Leu His Arg Gly Arg Cys Phe Asp Glu Cys Pro Asp Gly Phe
                85                  90

<210> SEQ ID NO 10
<211> LENGTH: 94
<212> TYPE: PRT
<213> ORGANISM: Homo sapiens

<400> SEQUENCE: 10

Ile Cys Lys Gly Cys Leu Ser Cys Ser Lys Asp Asn Gly Cys Ser Arg
1               5                   10                  15

Cys Gln Gln Lys Leu Phe Phe Phe Leu Arg Arg Glu Gly Met Arg Gln
            20                  25                  30

Tyr Gly Glu Cys Leu His Ser Cys Pro Ser Gly Tyr Tyr Gly His Arg
        35                  40                  45

Ala Pro Asp Met Asn Arg Cys Ala Arg Cys Arg Ile Glu Asn Cys Asp
    50                  55                  60

Ser Cys Phe Ser Lys Asp Phe Cys Thr Lys Cys Lys Val Gly Phe Tyr
65                  70                  75                  80

Leu His Arg Gly Arg Cys Phe Asp Glu Cys Pro Asp Gly Phe
                85                  90
```

<210> SEQ ID NO 11
<211> LENGTH: 177
<212> TYPE: DNA
<213> ORGANISM: Homo sapiens
<220> FEATURE:
<221> NAME/KEY: CDS
<222> LOCATION: (1)..(177)

<400> SEQUENCE: 11

```
gtt ggt cat tgg agc gaa tgg gga act tgt agc aga aat aat cgc aca      48
Val Gly His Trp Ser Glu Trp Gly Thr Cys Ser Arg Asn Asn Arg Thr
1               5                   10                  15 tgt gga ttt aaa tgg ggt ctg gaa acc aga aca cgg caa att gtt aaa      96
Cys Gly Phe Lys Trp Gly Leu Glu Thr Arg Thr Arg Gln Ile Val Lys
            20                  25                  30 aag cca gtg aaa gac aca ata ccg tgt cca acc att gct gaa tcc agg     144
Lys Pro Val Lys Asp Thr Ile Pro Cys Pro Thr Ile Ala Glu Ser Arg
        35                  40                  45 aga tgc aag atg aca atg agg cat tgt cca gga                         177
Arg Cys Lys Met Thr Met Arg His Cys Pro Gly
    50                  55
```

<210> SEQ ID NO 12
<211> LENGTH: 59
<212> TYPE: PRT
<213> ORGANISM: Homo sapiens

<400> SEQUENCE: 12

```
Val Gly His Trp Ser Glu Trp Gly Thr Cys Ser Arg Asn Asn Arg Thr
1               5                   10                  15

Cys Gly Phe Lys Trp Gly Leu Glu Thr Arg Thr Arg Gln Ile Val Lys
            20                  25                  30

Lys Pro Val Lys Asp Thr Ile Pro Cys Pro Thr Ile Ala Glu Ser Arg
        35                  40                  45

Arg Cys Lys Met Thr Met Arg His Cys Pro Gly
    50                  55
```

<210> SEQ ID NO 13
<211> LENGTH: 908
<212> TYPE: DNA
<213> ORGANISM: Homo sapiens
<220> FEATURE:
<221> NAME/KEY: CDS
<222> LOCATION: (101)..(805)

<400> SEQUENCE: 13

```
gcccacagca gccccgcgc ccgccgtgcc ccgccggga cgtggggccc ttgggccgtc       60
gggccgcctg gggagcgcca gcccggatcc ggctgcccag atg cgg gcg cca ctc     115
                                             Met Arg Ala Pro Leu
                                             1               5 tgc ctg ctc ctc gtc gcc cac gcc gtg gac atg ctc gcc ctg aac         163
Cys Leu Leu Leu Leu Val Ala His Ala Val Asp Met Leu Ala Leu Asn
            10                  15                  20 cga agg aag aag caa gtg ggc act ggc ctg ggg gcc aac tgc aca ggc     211
Arg Arg Lys Lys Gln Val Gly Thr Gly Leu Gly Ala Asn Cys Thr Gly
        25                  30                  35 tgt atc atc tgc tca gag gag aac ggc tgt tcc acc tgc cag cag agg     259
Cys Ile Ile Cys Ser Glu Glu Asn Gly Cys Ser Thr Cys Gln Gln Arg
    40                  45                  50 ctc ttc ctg ttc atc cgc cgg gaa ggc atc cgc cag tac ggc aag tgc     307
Leu Phe Leu Phe Ile Arg Arg Glu Gly Ile Arg Gln Tyr Gly Lys Cys
55                  60                  65
```

```
ctg cac gac tgt ccc cct ggg tac ttc ggc atc cgc ggc cag gag gtc      355
Leu His Asp Cys Pro Pro Gly Tyr Phe Gly Ile Arg Gly Gln Glu Val
 70              75                  80                  85 aac agg tgc aaa aaa tgt ggg gcc act tgt gag agc tgc ttc agc cag      403
Asn Arg Cys Lys Lys Cys Gly Ala Thr Cys Glu Ser Cys Phe Ser Gln
                 90                  95                 100 gac ttc tgc atc cgg tgc aag agg cag ttt tac ttg tac aag ggg aag      451
Asp Phe Cys Ile Arg Cys Lys Arg Gln Phe Tyr Leu Tyr Lys Gly Lys
                105                 110                 115 tgt ctg ccc acc tgc ccg ccg ggc act ttg gcc cac cag aac aca cgg      499
Cys Leu Pro Thr Cys Pro Pro Gly Thr Leu Ala His Gln Asn Thr Arg
        120                 125                 130 gag tgc cag ggg gag tgt gaa ctg ggt ccc tgg ggc ggc tgg agc ccc      547
Glu Cys Gln Gly Glu Cys Glu Leu Gly Pro Trp Gly Gly Trp Ser Pro
        135                 140                 145 tgc aca cac aat gga aag acc tgc ggc tcg gct tgg ggc ctg gag agc      595
Cys Thr His Asn Gly Lys Thr Cys Gly Ser Ala Trp Gly Leu Glu Ser
150                 155                 160                 165 cgg gta cga gag gct ggc cgg gct ggg cat gag gag gca gcc acc tgc      643
Arg Val Arg Glu Ala Gly Arg Ala Gly His Glu Glu Ala Ala Thr Cys
                170                 175                 180 cag gtg ctt tct gag tca agg aaa tgt ccc atc cag agg ccc tgc cca      691
Gln Val Leu Ser Glu Ser Arg Lys Cys Pro Ile Gln Arg Pro Cys Pro
            185                 190                 195 gga gag agg agc ccc ggc cag aag aag ggc agg aag gac cgg cgc cca      739
Gly Glu Arg Ser Pro Gly Gln Lys Lys Gly Arg Lys Asp Arg Arg Pro
        200                 205                 210 cgc aag gac agg aag ctg gac cgc agg ctg gac gtg agg ccg cgc cag      787
Arg Lys Asp Arg Lys Leu Asp Arg Arg Leu Asp Val Arg Pro Arg Gln
        215                 220                 225 ccc ggc ctg cag ccc tga ccgccggctc tcccgactct ctggtcctag              835
Pro Gly Leu Gln Pro
230 tcctcggccc ctgcacacct cctcctgctc cttctcctcc tctctcctta ctctttctcc    895 tctgtcttct cca                                                       908

<210> SEQ ID NO 14
<211> LENGTH: 234
<212> TYPE: PRT
<213> ORGANISM: Homo sapiens

<400> SEQUENCE: 14

Met Arg Ala Pro Leu Cys Leu Leu Leu Leu Val Ala His Ala Val Asp
1               5                  10                  15

Met Leu Ala Leu Asn Arg Arg Lys Lys Gln Val Gly Thr Gly Leu Gly
                20                  25                  30

Gly Asn Cys Thr Gly Cys Ile Ile Cys Ser Glu Glu Asn Gly Cys Ser
            35                  40                  45

Thr Cys Gln Gln Arg Leu Phe Leu Phe Ile Arg Arg Glu Gly Ile Arg
        50                  55                  60

Gln Tyr Gly Lys Cys Leu His Asp Cys Pro Pro Gly Tyr Phe Gly Ile
65                  70                  75                  80

Arg Gly Gln Glu Val Asn Arg Cys Lys Lys Cys Gly Ala Thr Cys Glu
                85                  90                  95

Ser Cys Phe Ser Gln Asp Phe Cys Ile Arg Cys Lys Arg Gln Phe Tyr
            100                 105                 110

Leu Tyr Lys Gly Lys Cys Leu Pro Thr Cys Pro Pro Gly Thr Leu Ala
```

```
                115                 120                 125
His Gln Asn Thr Arg Glu Cys Gln Gly Glu Cys Glu Leu Gly Pro Trp
    130                 135                 140

Gly Gly Trp Ser Pro Cys Thr His Asn Gly Lys Thr Cys Gly Ser Ala
145                 150                 155                 160

Trp Gly Leu Glu Ser Arg Val Arg Glu Ala Gly Arg Ala Gly His Glu
                165                 170                 175

Glu Ala Ala Thr Cys Gln Val Leu Ser Glu Ser Arg Lys Cys Pro Ile
            180                 185                 190

Gln Arg Pro Cys Pro Gly Glu Arg Ser Pro Gln Lys Lys Gly Arg
        195                 200                 205

Lys Asp Arg Arg Pro Arg Lys Asp Arg Lys Leu Asp Arg Arg Leu Asp
    210                 215                 220

Val Arg Pro Arg Gln Pro Gly Leu Gln Pro
225                 230

<210> SEQ ID NO 15
<211> LENGTH: 705
<212> TYPE: DNA
<213> ORGANISM: Homo sapiens

<400> SEQUENCE: 15
atgcgggcgc cactctgcct gctcctgctc gtcgcccacg ccgtggacat gctcgccctg        60
aaccgaagga agaagcaagt gggcactggc ctgggggcaa actgcacagg ctgtatcatc       120
tgctcagagg agaacggctg ttccacctgc agcagagggc tcttcctgtt catccgccgg       180
gaaggcatcc gccagtacgg caagtgcctg cacgactgtc cccctgggta cttcggcatc       240
cgcggccagg aggtcaacag tgcaaaaaa tgtggggcca cttgtgagag ctgcttcagc       300
caggacttct gcatccggtg caaggaggcag ttttacttgt acaaggggaa gtgtctgccc       360 acctgccgc cgggcacttt ggcccaccag aacacacggg agtgccaggg ggagtgtgaa       420
ctgggtccct ggggcggctg gagccctgc acacacaatg aaagacctgc ggctcggct       480 tggggcctgg agagccgggt acgagaggct ggccggctg gcatgagga gcagccacc       540 tgccaggtgc tttctgagtc aaggaaatgt cccatccaga ggccctgccc aggagagagg       600
agccccggcc agaagaaggg caggaaggac cggcgcccac gcaaggacag gaagctggac       660
cgcaggctgg acgtgaggcc gcgccagccc ggcctgcagc cctga                      705

<210> SEQ ID NO 16
<211> LENGTH: 645
<212> TYPE: DNA
<213> ORGANISM: Homo sapiens
<220> FEATURE:
<221> NAME/KEY: CDS
<222> LOCATION: (1)..(645)

<400> SEQUENCE: 16 aac cga agg aag aag caa gtg ggc act ggc ctg ggg ggc aac tgc aca        48
Asn Arg Arg Lys Lys Gln Val Gly Thr Gly Leu Gly Gly Asn Cys Thr
1               5                   10                  15 ggc tgt atc atc tgc tca gag gag aac ggc tgt tcc acc tgc cag cag        96
Gly Cys Ile Ile Cys Ser Glu Glu Asn Gly Cys Ser Thr Cys Gln Gln
                20                  25                  30 agg ctc ttc ctg ttc atc cgc cgg gaa ggc atc cgc cag tac ggc aag       144
Arg Leu Phe Leu Phe Ile Arg Arg Glu Gly Ile Arg Gln Tyr Gly Lys
            35                  40                  45 tgc ctg cac gac tgt ccc cct ggg tac ttc ggc atc cgc ggc cag gag       192
Cys Leu His Asp Cys Pro Pro Gly Tyr Phe Gly Ile Arg Gly Gln Glu
```

```
                gtc aac agg tgc aaa aaa tgt ggg gcc act tgt gag agc tgc ttc agc      240
                Val Asn Arg Cys Lys Lys Cys Gly Ala Thr Cys Glu Ser Cys Phe Ser
                 65                  70                  75                  80 cag gac ttc tgc atc cgg tgc aag agg cag ttt tac ttg tac aag ggg      288
                Gln Asp Phe Cys Ile Arg Cys Lys Arg Gln Phe Tyr Leu Tyr Lys Gly
                             85                  90                  95 aag tgt ctg ccc acc tgc ccg ccg ggc act ttg gcc cac cag aac aca      336
                Lys Cys Leu Pro Thr Cys Pro Pro Gly Thr Leu Ala His Gln Asn Thr
                        100                 105                 110 cgg gag tgc cag ggg gag tgt gaa ctg ggt ccc tgg ggc ggc tgg agc      384
                Arg Glu Cys Gln Gly Glu Cys Glu Leu Gly Pro Trp Gly Gly Trp Ser
                    115                 120                 125 ccc tgc aca cac aat gga aag acc tgc ggc tcg gct tgg ggc ctg gag      432
                Pro Cys Thr His Asn Gly Lys Thr Cys Gly Ser Ala Trp Gly Leu Glu
                130                 135                 140 agc cgg gta cga gag gct ggc cgg gct ggg cat gag gag gca gcc acc      480
                Ser Arg Val Arg Glu Ala Gly Arg Ala Gly His Glu Glu Ala Ala Thr
                145                 150                 155                 160 tgc cag gtg ctt tct gag tca agg aaa tgt ccc atc cag agg ccc tgc      528
                Cys Gln Val Leu Ser Glu Ser Arg Lys Cys Pro Ile Gln Arg Pro Cys
                                165                 170                 175 cca gga gag agg agc ccc ggc cag aag aag ggc agg aag gac cgg cgc      576
                Pro Gly Glu Arg Ser Pro Gly Gln Lys Lys Gly Arg Lys Asp Arg Arg
                            180                 185                 190 cca cgc aag gac agg aag ctg gac cgc agg ctg gac gtg agg ccg cgc      624
                Pro Arg Lys Asp Arg Lys Leu Asp Arg Arg Leu Asp Val Arg Pro Arg
                        195                 200                 205 cag ccc ggc ctg cag ccc tga                                           645
                Gln Pro Gly Leu Gln Pro
                    210

<210> SEQ ID NO 17
<211> LENGTH: 214
<212> TYPE: PRT
<213> ORGANISM: Homo sapiens

<400> SEQUENCE: 17

Asn Arg Arg Lys Lys Gln Val Gly Thr Gly Leu Gly Gly Asn Cys Thr
  1               5                  10                  15

Gly Cys Ile Ile Cys Ser Glu Glu Asn Gly Cys Ser Thr Cys Gln Gln
             20                  25                  30

Arg Leu Phe Leu Phe Ile Arg Arg Glu Gly Ile Arg Gln Tyr Gly Lys
         35                  40                  45

Cys Leu His Asp Cys Pro Pro Gly Tyr Phe Gly Ile Arg Gly Gln Glu
     50                  55                  60

Val Asn Arg Cys Lys Lys Cys Gly Ala Thr Cys Glu Ser Cys Phe Ser
 65                  70                  75                  80

Gln Asp Phe Cys Ile Arg Cys Lys Arg Gln Phe Tyr Leu Tyr Lys Gly
                 85                  90                  95

Lys Cys Leu Pro Thr Cys Pro Pro Gly Thr Leu Ala His Gln Asn Thr
            100                 105                 110

Arg Glu Cys Gln Gly Glu Cys Glu Leu Gly Pro Trp Gly Gly Trp Ser
        115                 120                 125

Pro Cys Thr His Asn Gly Lys Thr Cys Gly Ser Ala Trp Gly Leu Glu
    130                 135                 140

Ser Arg Val Arg Glu Ala Gly Arg Ala Gly His Glu Glu Ala Ala Thr
```

```
                145                 150                 155                 160
Cys Gln Val Leu Ser Glu Ser Arg Lys Cys Pro Ile Gln Arg Pro Cys
                165                 170                 175

Pro Gly Glu Arg Ser Pro Gly Gln Lys Lys Gly Arg Lys Asp Arg Arg
            180                 185                 190

Pro Arg Lys Asp Arg Lys Leu Asp Arg Arg Leu Asp Val Arg Pro Arg
        195                 200                 205

Gln Pro Gly Leu Gln Pro
    210

<210> SEQ ID NO 18
<211> LENGTH: 279
<212> TYPE: DNA
<213> ORGANISM: Homo sapiens
<220> FEATURE:
<221> NAME/KEY: CDS
<222> LOCATION: (1)..(279)

<400> SEQUENCE: 18 aac tgc aca ggc tgt atc atc tgc tca gag gag aac ggc tgt tcc acc        48
Asn Cys Thr Gly Cys Ile Ile Cys Ser Glu Glu Asn Gly Cys Ser Thr
1               5                   10                  15 tgc cag cag agg ctc ttc ctg ttc atc cgc cgg gaa ggc atc cgc cag        96
Cys Gln Gln Arg Leu Phe Leu Phe Ile Arg Arg Glu Gly Ile Arg Gln
            20                  25                  30 tac ggc aag tgc ctg cac gac tgt ccc cct ggg tac ttc ggc atc cgc       144
Tyr Gly Lys Cys Leu His Asp Cys Pro Pro Gly Tyr Phe Gly Ile Arg
        35                  40                  45 ggc cag gag gtc aac agg tgc aaa aaa tgt ggg gcc act tgt gag agc       192
Gly Gln Glu Val Asn Arg Cys Lys Lys Cys Gly Ala Thr Cys Glu Ser
    50                  55                  60 tgc ttc agc cag gac ttc tgc atc cgg tgc aag agg cag ttt tac ttg       240
Cys Phe Ser Gln Asp Phe Cys Ile Arg Cys Lys Arg Gln Phe Tyr Leu
65                  70                  75                  80 tac aag ggg aag tgt ctg ccc acc tgc ccg ccg ggc act                   279
Tyr Lys Gly Lys Cys Leu Pro Thr Cys Pro Pro Gly Thr
                85                  90

<210> SEQ ID NO 19
<211> LENGTH: 93
<212> TYPE: PRT
<213> ORGANISM: Homo sapiens

<400> SEQUENCE: 19

Asn Cys Thr Gly Cys Ile Ile Cys Ser Glu Glu Asn Gly Cys Ser Thr
1               5                   10                  15

Cys Gln Gln Arg Leu Phe Leu Phe Ile Arg Arg Glu Gly Ile Arg Gln
            20                  25                  30

Tyr Gly Lys Cys Leu His Asp Cys Pro Pro Gly Tyr Phe Gly Ile Arg
        35                  40                  45

Gly Gln Glu Val Asn Arg Cys Lys Lys Cys Gly Ala Thr Cys Glu Ser
    50                  55                  60

Cys Phe Ser Gln Asp Phe Cys Ile Arg Cys Lys Arg Gln Phe Tyr Leu
65                  70                  75                  80

Tyr Lys Gly Lys Cys Leu Pro Thr Cys Pro Pro Gly Thr
                85                  90

<210> SEQ ID NO 20
<211> LENGTH: 171
<212> TYPE: DNA
```

<213> ORGANISM: Homo sapiens
<220> FEATURE:
<221> NAME/KEY: CDS
<222> LOCATION: (1)..(171)

<400> SEQUENCE: 20

```
ctg ggt ccc tgg ggc ggc tgg agc ccc tgc aca cac aat gga aag acc      48
Leu Gly Pro Trp Gly Gly Trp Ser Pro Cys Thr His Asn Gly Lys Thr
1               5                   10                  15 tgc ggc tcg gct tgg ggc ctg gag agc cgg gta cga gag gct ggc cgg      96
Cys Gly Ser Ala Trp Gly Leu Glu Ser Arg Val Arg Glu Ala Gly Arg
            20                  25                  30 gct ggg cat gag gag gca gcc acc tgc cag gtg ctt tct gag tca agg     144
Ala Gly His Glu Glu Ala Ala Thr Cys Gln Val Leu Ser Glu Ser Arg
        35                  40                  45 aaa tgt ccc atc cag agg ccc tgc cca                                 171
Lys Cys Pro Ile Gln Arg Pro Cys Pro
50                  55
```

<210> SEQ ID NO 21
<211> LENGTH: 57
<212> TYPE: PRT
<213> ORGANISM: Homo sapiens

<400> SEQUENCE: 21

```
Leu Gly Pro Trp Gly Gly Trp Ser Pro Cys Thr His Asn Gly Lys Thr
1               5                   10                  15

Cys Gly Ser Ala Trp Gly Leu Glu Ser Arg Val Arg Glu Ala Gly Arg
            20                  25                  30

Ala Gly His Glu Glu Ala Ala Thr Cys Gln Val Leu Ser Glu Ser Arg
        35                  40                  45

Lys Cys Pro Ile Gln Arg Pro Cys Pro
    50                  55
```

<210> SEQ ID NO 22
<211> LENGTH: 722
<212> TYPE: DNA
<213> ORGANISM: Homo sapiens
<220> FEATURE:
<221> NAME/KEY: CDS
<222> LOCATION: (101)..(619)

<400> SEQUENCE: 22

```
gcccacagca gccccgcgc ccgccgtgcc gccgccggga cgtggggccc ttgggccgtc     60
gggccgcctg gggagcgcca gcccggatcc ggctgcccag atg cgg gcg cca ctc    115
                                            Met Arg Ala Pro Leu
                                            1               5 tgc ctg ctc ctg ctc gtc gcc cac gcc gtg gac atg ctc gcc ctg aac    163
Cys Leu Leu Leu Leu Val Ala His Ala Val Asp Met Leu Ala Leu Asn
                10                  15                  20 cga agg aag aag caa gtg ggc act ggc ctg ggg ggc aac tgc aca ggc    211
Arg Arg Lys Lys Gln Val Gly Thr Gly Leu Gly Gly Asn Cys Thr Gly
            25                  30                  35 tgt atc atc tgc tca gag gag aac ggc tgt tcc acc tgc cag cag agg    259
Cys Ile Ile Cys Ser Glu Glu Asn Gly Cys Ser Thr Cys Gln Gln Arg
        40                  45                  50 ctc ttc ctg ttc atc cgc cgg gaa ggc atc cgc cag tac ggc aag tgc    307
Leu Phe Leu Phe Ile Arg Arg Glu Gly Ile Arg Gln Tyr Gly Lys Cys
    55                  60                  65 ctg cac gac tgt ccc cct ggg tac ttc ggc atc cgc ggc cag gag gtc    355
Leu His Asp Cys Pro Pro Gly Tyr Phe Gly Ile Arg Gly Gln Glu Val
70                  75                  80                  85
```

```
aac agg tgc aaa aaa tgt ggg gcc act tgt gag agc tgc ttc agc cag      403
Asn Arg Cys Lys Lys Cys Gly Ala Thr Cys Glu Ser Cys Phe Ser Gln
                90                  95                 100 gac ttc tgc atc cgg tgc aag agg cag ttt tac ttg tac aag ggg aag      451
Asp Phe Cys Ile Arg Cys Lys Arg Gln Phe Tyr Leu Tyr Lys Gly Lys
            105                 110                 115 tgt ctg ccc acc tgc ccg ccg ggc act ttg gcc cac cag aac aca cgg      499
Cys Leu Pro Thr Cys Pro Pro Gly Thr Leu Ala His Gln Asn Thr Arg
        120                 125                 130 gag tgc cag gag agg agc ccc ggc cag aag aag ggc agg aag gac cgg      547
Glu Cys Gln Glu Arg Ser Pro Gly Gln Lys Lys Gly Arg Lys Asp Arg
    135                 140                 145 cgc cca cgc aag gac agg aag ctg gac cgc agg ctg gac gtg agg ccg      595
Arg Pro Arg Lys Asp Arg Lys Leu Asp Arg Arg Leu Asp Val Arg Pro
150                 155                 160                 165 cgc cag ccc ggc ctg cag ccc tga ccgccggctc tcccgactct ctggtcctag    649
Arg Gln Pro Gly Leu Gln Pro
                170 tcctcggccc ctgcacacct cctcctgctc cttctcctcc tctcctctta ctctttctcc   709 tctgtcttct cca                                                      722

<210> SEQ ID NO 23
<211> LENGTH: 172
<212> TYPE: PRT
<213> ORGANISM: Homo sapiens

<400> SEQUENCE: 23

Met Arg Ala Pro Leu Cys Leu Leu Leu Val Ala His Ala Val Asp
1               5                  10                  15

Met Leu Ala Leu Asn Arg Arg Lys Lys Gln Val Gly Thr Gly Leu Gly
                20                  25                  30

Gly Asn Cys Thr Gly Cys Ile Ile Cys Ser Glu Glu Asn Gly Cys Ser
            35                  40                  45

Thr Cys Gln Gln Arg Leu Phe Leu Phe Ile Arg Arg Glu Gly Ile Arg
        50                  55                  60

Gln Tyr Gly Lys Cys Leu His Asp Cys Pro Pro Gly Tyr Phe Gly Ile
65                  70                  75                  80

Arg Gly Gln Glu Val Asn Arg Cys Lys Lys Cys Gly Ala Thr Cys Glu
                85                  90                  95

Ser Cys Phe Ser Gln Asp Phe Cys Ile Arg Cys Lys Arg Gln Phe Tyr
            100                 105                 110

Leu Tyr Lys Gly Lys Cys Leu Pro Thr Cys Pro Pro Gly Thr Leu Ala
        115                 120                 125

His Gln Asn Thr Arg Glu Cys Gln Glu Arg Ser Pro Gly Gln Lys Lys
    130                 135                 140

Gly Arg Lys Asp Arg Arg Pro Arg Lys Asp Arg Lys Leu Asp Arg Arg
145                 150                 155                 160

Leu Asp Val Arg Pro Arg Gln Pro Gly Leu Gln Pro
                165                 170

<210> SEQ ID NO 24
<211> LENGTH: 519
<212> TYPE: DNA
<213> ORGANISM: Homo sapiens

<400> SEQUENCE: 24
atgcgggcgc cactctgcct gctcctgctc gtcgcccacg ccgtggacat gctcgccctg   60
```

```
aaccgaagga agaagcaagt gggcactggc ctggggggca actgcacagg ctgtatcatc    120
tgctcagagg agaacggctg ttccacctgc agcagaggc tcttcctgtt catccgccgg     180
gaaggcatcc gccagtacgg caagtgcctg cacgactgtc ccctgggta cttcggcatc    240 cgcggccagg aggtcaacag gtgcaaaaaa tgtggggcca cttgtgagag ctgcttcagc    300
caggacttct gcatccggtg caagaggcag ttttacttgt acaagggaa gtgtctgccc    360 acctgcccgc cgggcacttt ggcccaccag aacacacggg agtgccagga gaggagcccc    420
ggccagaaga agggcaggaa ggaccggcgc ccacgcaagg acaggaagct ggaccgcagg    480
ctggacgtga ggccgcgcca gcccggcctg cagccctga                          519

<210> SEQ ID NO 25
<211> LENGTH: 459
<212> TYPE: DNA
<213> ORGANISM: Homo sapiens
<220> FEATURE:
<221> NAME/KEY: CDS
<222> LOCATION: (1)..(459)

<400> SEQUENCE: 25 aac cga agg aag aag caa gtg ggc act ggc ctg ggg ggc aac tgc aca       48
Asn Arg Arg Lys Lys Gln Val Gly Thr Gly Leu Gly Gly Asn Cys Thr
1               5                   10                  15 ggc tgt atc atc tgc tca gag gag aac ggc tgt tcc acc tgc cag cag       96
Gly Cys Ile Ile Cys Ser Glu Glu Asn Gly Cys Ser Thr Cys Gln Gln
            20                  25                  30 agg ctc ttc ctg ttc atc cgc cgg gaa ggc atc cgc cag tac ggc aag      144
Arg Leu Phe Leu Phe Ile Arg Arg Glu Gly Ile Arg Gln Tyr Gly Lys
        35                  40                  45 tgc ctg cac gac tgt ccc cct ggg tac ttc ggc atc cgc ggc cag gag      192
Cys Leu His Asp Cys Pro Pro Gly Tyr Phe Gly Ile Arg Gly Gln Glu
    50                  55                  60 gtc aac agg tgc aaa aaa tgt ggg gcc act tgt gag agc tgc ttc agc      240
Val Asn Arg Cys Lys Lys Cys Gly Ala Thr Cys Glu Ser Cys Phe Ser
65                  70                  75                  80 cag gac ttc tgc atc cgg tgc aag agg cag ttt tac ttg tac aag ggg      288
Gln Asp Phe Cys Ile Arg Cys Lys Arg Gln Phe Tyr Leu Tyr Lys Gly
                85                  90                  95 aag tgt ctg ccc acc tgc ccg ccg ggc act ttg gcc cac cag aac aca      336
Lys Cys Leu Pro Thr Cys Pro Pro Gly Thr Leu Ala His Gln Asn Thr
            100                 105                 110 cgg gag tgc cag gag agg agc ccc ggc cag aag aag ggc agg aag gac      384
Arg Glu Cys Gln Glu Arg Ser Pro Gly Gln Lys Lys Gly Arg Lys Asp
        115                 120                 125 cgg cgc cca cgc aag gac agg aag ctg gac cgc agg ctg gac gtg agg      432
Arg Arg Pro Arg Lys Asp Arg Lys Leu Asp Arg Arg Leu Asp Val Arg
    130                 135                 140 ccg cgc cag ccc ggc ctg cag ccc tga                                  459
Pro Arg Gln Pro Gly Leu Gln Pro
145                 150

<210> SEQ ID NO 26
<211> LENGTH: 152
<212> TYPE: PRT
<213> ORGANISM: Homo sapiens

<400> SEQUENCE: 26

Asn Arg Arg Lys Lys Gln Val Gly Thr Gly Leu Gly Gly Asn Cys Thr
1               5                   10                  15
```

-continued

```
Gly Cys Ile Ile Cys Ser Glu Glu Asn Gly Cys Ser Thr Cys Gln Gln
            20                  25                  30

Arg Leu Phe Leu Phe Ile Arg Arg Glu Gly Ile Arg Gln Tyr Gly Lys
        35                  40                  45

Cys Leu His Asp Cys Pro Pro Gly Tyr Phe Gly Ile Arg Gly Gln Glu
    50                  55                  60

Val Asn Arg Cys Lys Lys Cys Gly Ala Thr Cys Glu Ser Cys Phe Ser
65                  70                  75                  80

Gln Asp Phe Cys Ile Arg Cys Lys Arg Gln Phe Tyr Leu Tyr Lys Gly
                85                  90                  95

Lys Cys Leu Pro Thr Cys Pro Pro Gly Thr Leu Ala His Gln Asn Thr
            100                 105                 110

Arg Glu Cys Gln Glu Arg Ser Pro Gly Gln Lys Lys Gly Arg Lys Asp
        115                 120                 125

Arg Arg Pro Arg Lys Asp Arg Lys Leu Asp Arg Arg Leu Asp Val Arg
    130                 135                 140

Pro Arg Gln Pro Gly Leu Gln Pro
145                 150
```

<210> SEQ ID NO 27
<211> LENGTH: 19
<212> TYPE: DNA
<213> ORGANISM: Artificial sequence
<220> FEATURE:
<223> OTHER INFORMATION: F primer for cloning SCFA2 into pIntron/Igk
      1round PCR

<400> SEQUENCE: 27
ctttgggcga accctccag                                                19

<210> SEQ ID NO 28
<211> LENGTH: 20
<212> TYPE: DNA
<213> ORGANISM: Artificial sequence
<220> FEATURE:
<223> OTHER INFORMATION: R primer for cloning SCFA2 into pIntron/Igk
      1round PCR

<400> SEQUENCE: 28
gagcagcaca aaggctgcac                                               20

<210> SEQ ID NO 29
<211> LENGTH: 37
<212> TYPE: DNA
<213> ORGANISM: Artificial sequence
<220> FEATURE:
<223> OTHER INFORMATION: F primer SCFA2 cloning 2nd PCR round for
      cloning SCFA2 into pIntron/Igk

<400> SEQUENCE: 29
ccggctagcg ctagttatgt atcaaatccc atttgca                            37

<210> SEQ ID NO 30
<211> LENGTH: 36
<212> TYPE: DNA
<213> ORGANISM: Artificial sequence
<220> FEATURE:
<223> OTHER INFORMATION: R primer SCFA2 cloning 2nd PCR round for
      cloning SCFA2 into pIntron/Igk

<400> SEQUENCE: 30
tgctctagac tttggttagc tctgtctgta gctagg                             36

-continued

<210> SEQ ID NO 31
<211> LENGTH: 22
<212> TYPE: DNA
<213> ORGANISM: Artificial sequence
<220> FEATURE:
<223> OTHER INFORMATION: F primer for cloning SCFA4-4v into pIntron/Igk
      1round PCR

<400> SEQUENCE: 31
tggggccctt gggccgtcgg gc                                              22

<210> SEQ ID NO 32
<211> LENGTH: 21
<212> TYPE: DNA
<213> ORGANISM: Artificial sequence
<220> FEATURE:
<223> OTHER INFORMATION: R primer for cloning SCFA4-4v into pIntron/Igk
      1round PCR

<400> SEQUENCE: 32
aaggagcagg aggaggtgtg c                                               21

<210> SEQ ID NO 33
<211> LENGTH: 32
<212> TYPE: DNA
<213> ORGANISM: Artificial sequence
<220> FEATURE:
<223> OTHER INFORMATION: F primer for cloning SCFA4 and 4v into
      pIntron/Igk 2nd  round PCR

<400> SEQUENCE: 33
ctgagctagc ctgaaccgaa ggaagaagca ag                                   32

<210> SEQ ID NO 34
<211> LENGTH: 33
<212> TYPE: DNA
<213> ORGANISM: Artificial sequence
<220> FEATURE:
<223> OTHER INFORMATION: R primer for cloning SCFA4 and 4v into
      pIntron/Igk 2nd  round PCR

<400> SEQUENCE: 34
ctgatctaga ccgggctgca ggccgggctg gcg                                  33

<210> SEQ ID NO 35
<211> LENGTH: 813
<212> TYPE: DNA
<213> ORGANISM: Artificial sequence
<220> FEATURE:
<223> OTHER INFORMATION: IgK-SCFA2-V5His6
<220> FEATURE:
<221> NAME/KEY: CDS
<222> LOCATION: (1)..(813)

<400> SEQUENCE: 35

| atg | gag | aca | gac | aca | ctc | ctg | cta | tgg | gta | ctg | ctg | ctc | tgg | gtt | cca | 48 |
|---|---|---|---|---|---|---|---|---|---|---|---|---|---|---|---|---|
| Met | Glu | Thr | Asp | Thr | Leu | Leu | Leu | Trp | Val | Leu | Leu | Leu | Trp | Val | Pro | |
| 1 | | | | 5 | | | | | 10 | | | | | 15 | | |

| ggt | tcc | act | ggt | gac | gct | agc | gct | agt | tat | gta | tca | aat | ccc | att | tgc | 96 |
|---|---|---|---|---|---|---|---|---|---|---|---|---|---|---|---|---|
| Gly | Ser | Thr | Gly | Asp | Ala | Ser | Ala | Ser | Tyr | Val | Ser | Asn | Pro | Ile | Cys | |
| | | 20 | | | | | 25 | | | | | 30 | | | | |

| aag | ggt | tgt | ttg | tct | tgt | tca | aag | gac | aat | ggg | tgt | agc | cga | tgt | caa | 144 |
|---|---|---|---|---|---|---|---|---|---|---|---|---|---|---|---|---|
| Lys | Gly | Cys | Leu | Ser | Cys | Ser | Lys | Asp | Asn | Gly | Cys | Ser | Arg | Cys | Gln | |
| | 35 | | | | | 40 | | | | | 45 | | | | | |

| cag | aag | ttg | ttc | ttc | ttc | ctt | cga | aga | gaa | ggg | atg | cgc | cag | tat | gga | 192 |
|---|---|---|---|---|---|---|---|---|---|---|---|---|---|---|---|---|
| Gln | Lys | Leu | Phe | Phe | Phe | Leu | Arg | Arg | Glu | Gly | Met | Arg | Gln | Tyr | Gly | |

```
                50                  55                  60
gag tgc ctg cat tcc tgc cca tcc ggg tac tat gga cac cga gcc cca        240
Glu Cys Leu His Ser Cys Pro Ser Gly Tyr Tyr Gly His Arg Ala Pro
 65                  70                  75                  80 gat atg aac aga tgt gca aga tgc aga ata gaa aac tgt gat tct tgc        288
Asp Met Asn Arg Cys Ala Arg Cys Arg Ile Glu Asn Cys Asp Ser Cys
                 85                  90                  95 ttt agc aaa gac ttt tgt acc aag tgc aaa gta ggc ttt tat ttg cat        336
Phe Ser Lys Asp Phe Cys Thr Lys Cys Lys Val Gly Phe Tyr Leu His
                100                 105                 110 aga ggc cgt tgc ttt gat gaa tgt cca gat ggt ttt gca cca tta gaa        384
Arg Gly Arg Cys Phe Asp Glu Cys Pro Asp Gly Phe Ala Pro Leu Glu
            115                 120                 125 gaa acc atg gaa tgt gtg gaa gga tgt gaa gtt ggt cat tgg agc gaa        432
Glu Thr Met Glu Cys Val Glu Gly Cys Glu Val Gly His Trp Ser Glu
        130                 135                 140 tgg gga act tgt agc aga aat aat cgc aca tgt gga ttt aaa tgg ggt        480
Trp Gly Thr Cys Ser Arg Asn Asn Arg Thr Cys Gly Phe Lys Trp Gly
145                 150                 155                 160 ctg gaa acc aga aca cgg caa att gtt aaa aag cca gtg aaa gac aca        528
Leu Glu Thr Arg Thr Arg Gln Ile Val Lys Lys Pro Val Lys Asp Thr
                165                 170                 175 ata ccg tgt cca acc att gct gaa tcc agg aga tgc aag atg aca atg        576
Ile Pro Cys Pro Thr Ile Ala Glu Ser Arg Arg Cys Lys Met Thr Met
            180                 185                 190 agg cat tgt cca gga ggg aag aga aca cca aag gcg aag gag aag agg        624
Arg His Cys Pro Gly Gly Lys Arg Thr Pro Lys Ala Lys Glu Lys Arg
        195                 200                 205 aac aag aaa aag aaa agg aag ctg ata gaa agg gcc cag gag caa cac        672
Asn Lys Lys Lys Lys Arg Lys Leu Ile Glu Arg Ala Gln Glu Gln His
210                 215                 220 agc gtc ttc cta gct aca gac aga gct aac caa ggc ggc cgc tcg agt        720
Ser Val Phe Leu Ala Thr Asp Arg Ala Asn Gln Gly Gly Arg Ser Ser
225                 230                 235                 240 cta gag ggc ccg cgg ttc gaa ggt aag cct atc cct aac cct ctc ctc        768
Leu Glu Gly Pro Arg Phe Glu Gly Lys Pro Ile Pro Asn Pro Leu Leu
                245                 250                 255 ggt ctc gat tct acg cgt acc ggt cat cat cac cat cac cat tga            813
Gly Leu Asp Ser Thr Arg Thr Gly His His His His His His
            260                 265                 270

<210> SEQ ID NO 36
<211> LENGTH: 270
<212> TYPE: PRT
<213> ORGANISM: Artificial sequence
<220> FEATURE:
<223> OTHER INFORMATION: Synthetic Construct

<400> SEQUENCE: 36

Met Glu Thr Asp Thr Leu Leu Leu Trp Val Leu Leu Leu Trp Val Pro
 1               5                  10                  15

Gly Ser Thr Gly Asp Ala Ser Ala Ser Tyr Val Ser Asn Pro Ile Cys
             20                  25                  30

Lys Gly Cys Leu Ser Cys Ser Lys Asp Asn Gly Cys Ser Arg Cys Gln
         35                  40                  45

Gln Lys Leu Phe Phe Phe Leu Arg Arg Glu Gly Met Arg Gln Tyr Gly
     50                  55                  60

Glu Cys Leu His Ser Cys Pro Ser Gly Tyr Tyr Gly His Arg Ala Pro
 65                  70                  75                  80
```

```
Asp Met Asn Arg Cys Ala Arg Cys Arg Ile Glu Asn Cys Asp Ser Cys
            85                  90                  95

Phe Ser Lys Asp Phe Cys Thr Lys Cys Lys Val Gly Phe Tyr Leu His
            100                 105                 110

Arg Gly Arg Cys Phe Asp Glu Cys Pro Asp Gly Phe Ala Pro Leu Glu
            115                 120                 125

Glu Thr Met Glu Cys Val Glu Gly Cys Glu Val Gly His Trp Ser Glu
            130                 135                 140

Trp Gly Thr Cys Ser Arg Asn Asn Arg Thr Cys Gly Phe Lys Trp Gly
145                 150                 155                 160

Leu Glu Thr Arg Thr Arg Gln Ile Val Lys Lys Pro Val Lys Asp Thr
            165                 170                 175

Ile Pro Cys Pro Thr Ile Ala Glu Ser Arg Arg Cys Lys Met Thr Met
            180                 185                 190

Arg His Cys Pro Gly Gly Lys Arg Thr Pro Lys Ala Lys Glu Lys Arg
            195                 200                 205

Asn Lys Lys Lys Arg Lys Leu Ile Glu Arg Ala Gln Glu Gln His
            210                 215                 220

Ser Val Phe Leu Ala Thr Asp Arg Ala Asn Gln Gly Gly Arg Ser Ser
225                 230                 235                 240

Leu Glu Gly Pro Arg Phe Glu Gly Lys Pro Ile Pro Asn Pro Leu Leu
            245                 250                 255

Gly Leu Asp Ser Thr Arg Thr Gly His His His His His His
            260                 265                 270

<210> SEQ ID NO 37
<211> LENGTH: 35
<212> TYPE: DNA
<213> ORGANISM: Artificial sequence
<220> FEATURE:
<223> OTHER INFORMATION: F primer for cloning out IgK-SCFA2-V5His from
      pIntron into Adeno

<400> SEQUENCE: 37
tgctctagac accatggaga cagacacact cctgc                               35

<210> SEQ ID NO 38
<211> LENGTH: 38
<212> TYPE: DNA
<213> ORGANISM: Artificial sequence
<220> FEATURE:
<223> OTHER INFORMATION: R primer for cloning out IgK-SCFA2-V5His from
      pIntron into Adeno

<400> SEQUENCE: 38
ccatgcggcc gccttggtta gctctgtctg tagctagg                            38

<210> SEQ ID NO 39
<211> LENGTH: 822
<212> TYPE: DNA
<213> ORGANISM: Artificial sequence
<220> FEATURE:
<223> OTHER INFORMATION: IgK-SCFA4-V5His
<220> FEATURE:
<221> NAME/KEY: CDS
<222> LOCATION: (1)..(822)

<400> SEQUENCE: 39 atg gag aca gac aca ctc ctg cta tgg gta ctg ctg ctc tgg gtt cca    48
Met Glu Thr Asp Thr Leu Leu Leu Trp Val Leu Leu Leu Trp Val Pro
1               5                   10                  15
```

```
ggt tcc act ggt gac gct agc ctg aac cga agg aag aag caa gtg ggc        96
Gly Ser Thr Gly Asp Ala Ser Leu Asn Arg Arg Lys Lys Gln Val Gly
         20                  25                  30 act ggc ctg ggg ggc aac tgc aca ggc tgt atc atc tgc tca gag gag       144
Thr Gly Leu Gly Gly Asn Cys Thr Gly Cys Ile Ile Cys Ser Glu Glu
     35                  40                  45 aac ggc tgt tcc acc tgc cag cag agg ctc ttc ctg ttc atc cgc cgg       192
Asn Gly Cys Ser Thr Cys Gln Gln Arg Leu Phe Leu Phe Ile Arg Arg
 50                  55                  60 gaa ggc atc cgc cag tac ggc aag tgc ctg cac gac tgt ccc cct ggg       240
Glu Gly Ile Arg Gln Tyr Gly Lys Cys Leu His Asp Cys Pro Pro Gly
 65                  70                  75                  80 tac ttc ggc atc cgc ggc cag gag gtc aac agg tgc aaa aaa tgt ggg       288
Tyr Phe Gly Ile Arg Gly Gln Glu Val Asn Arg Cys Lys Lys Cys Gly
                 85                  90                  95 gcc act tgt gag agc tgc ttc agc cag gac ttc tgc atc cgg tgc aag       336
Ala Thr Cys Glu Ser Cys Phe Ser Gln Asp Phe Cys Ile Arg Cys Lys
            100                 105                 110 agg cag ttt tac ttg tac aag ggg aag tgt ctg ccc acc tgc ccg ccg       384
Arg Gln Phe Tyr Leu Tyr Lys Gly Lys Cys Leu Pro Thr Cys Pro Pro
        115                 120                 125 ggc act ttg gct cac cag aac aca cgg gag tgc cag ggg gag tgt gaa       432
Gly Thr Leu Ala His Gln Asn Thr Arg Glu Cys Gln Gly Glu Cys Glu
130                 135                 140 ctg ggt ccc tgg ggc ggc tgg agc ccc tgc aca cac aat gga aag acc       480
Leu Gly Pro Trp Gly Gly Trp Ser Pro Cys Thr His Asn Gly Lys Thr
145                 150                 155                 160 tgc ggc tcg gct tgg ggc ctg gag agc cgg gta cga gag gct ggc cgg       528
Cys Gly Ser Ala Trp Gly Leu Glu Ser Arg Val Arg Glu Ala Gly Arg
                165                 170                 175 gct ggg cat gag gag gca gcc acc tgc cag gtg ctt tct gag tca agg       576
Ala Gly His Glu Glu Ala Ala Thr Cys Gln Val Leu Ser Glu Ser Arg
            180                 185                 190 aaa tgt ccc atc cag agg ccc tgc cca gga gag agg agc ccc ggc cag       624
Lys Cys Pro Ile Gln Arg Pro Cys Pro Gly Glu Arg Ser Pro Gly Gln
        195                 200                 205 aag aag ggc agg aag gac cgg cgc cca cgc aag gac agg aag ctg gac       672
Lys Lys Gly Arg Lys Asp Arg Arg Pro Arg Lys Asp Arg Lys Leu Asp
210                 215                 220 cgc agg ctg gac gtg agg ccg cgc cag ccc ggc ctg cag ccc ggc ggc       720
Arg Arg Leu Asp Val Arg Pro Arg Gln Pro Gly Leu Gln Pro Gly Gly
225                 230                 235                 240 cgc tcg agt cta gag ggc ccg cgg ttc gaa ggt aag cct atc cct aac       768
Arg Ser Ser Leu Glu Gly Pro Arg Phe Glu Gly Lys Pro Ile Pro Asn
                245                 250                 255 cct ctc ctc ggt ctc gat tct acg cgt acc ggt cat cat cac cat cac       816
Pro Leu Leu Gly Leu Asp Ser Thr Arg Thr Gly His His His His His
            260                 265                 270 cat tga                                                                822
His
```

<210> SEQ ID NO 40
<211> LENGTH: 273
<212> TYPE: PRT
<213> ORGANISM: Artificial sequence
<220> FEATURE:
<223> OTHER INFORMATION: Synthetic Construct

<400> SEQUENCE: 40

```
Met Glu Thr Asp Thr Leu Leu Leu Trp Val Leu Leu Leu Trp Val Pro
 1               5                  10                  15
```

```
Gly Ser Thr Gly Asp Ala Ser Leu Asn Arg Arg Lys Lys Gln Val Gly
            20                  25                  30

Thr Gly Leu Gly Gly Asn Cys Thr Gly Cys Ile Ile Cys Ser Glu Glu
        35                  40                  45

Asn Gly Cys Ser Thr Cys Gln Gln Arg Leu Phe Leu Phe Ile Arg Arg
    50                  55                  60

Glu Gly Ile Arg Gln Tyr Gly Lys Cys Leu His Asp Cys Pro Pro Gly
65                  70                  75                  80

Tyr Phe Gly Ile Arg Gly Gln Glu Val Asn Arg Cys Lys Lys Cys Gly
                85                  90                  95

Ala Thr Cys Glu Ser Cys Phe Ser Gln Asp Phe Cys Ile Arg Cys Lys
            100                 105                 110

Arg Gln Phe Tyr Leu Tyr Lys Gly Lys Cys Leu Pro Thr Cys Pro Pro
        115                 120                 125

Gly Thr Leu Ala His Gln Asn Thr Arg Glu Cys Gln Gly Glu Cys Glu
    130                 135                 140

Leu Gly Pro Trp Gly Gly Trp Ser Pro Cys Thr His Asn Gly Lys Thr
145                 150                 155                 160

Cys Gly Ser Ala Trp Gly Leu Glu Ser Arg Val Arg Glu Ala Gly Arg
                165                 170                 175

Ala Gly His Glu Glu Ala Ala Thr Cys Gln Val Leu Ser Glu Ser Arg
            180                 185                 190

Lys Cys Pro Ile Gln Arg Pro Cys Pro Gly Glu Arg Ser Pro Gly Gln
        195                 200                 205

Lys Lys Gly Arg Lys Asp Arg Arg Pro Arg Lys Asp Arg Lys Leu Asp
    210                 215                 220

Arg Arg Leu Asp Val Arg Pro Arg Gln Pro Gly Leu Gln Pro Gly Gly
225                 230                 235                 240

Arg Ser Ser Leu Glu Gly Pro Arg Phe Glu Gly Lys Pro Ile Pro Asn
                245                 250                 255

Pro Leu Leu Gly Leu Asp Ser Thr Arg Thr Gly His His His His
            260                 265                 270
His

<210> SEQ ID NO 41
<211> LENGTH: 35
<212> TYPE: DNA
<213> ORGANISM: Artificial sequence
<220> FEATURE:
<223> OTHER INFORMATION: F primer for cloning out IgK-SCFA4(4v)-V5His
      from pIntron into Adeno

<400> SEQUENCE: 41
tgctctagac accatggaga cagacacact cctgc                                35

<210> SEQ ID NO 42
<211> LENGTH: 31
<212> TYPE: DNA
<213> ORGANISM: Artificial sequence
<220> FEATURE:
<223> OTHER INFORMATION: R primer for cloning out IgK-SCFA4(4v)-V5His
      from pIntron into Adeno

<400> SEQUENCE: 42
ccatgcggcc gccgggctgc aggccgggct g                                    31

<210> SEQ ID NO 43
```

<211> LENGTH: 636
<212> TYPE: DNA
<213> ORGANISM: Artificial sequence
<220> FEATURE:
<223> OTHER INFORMATION: IgK-SCFA4v-V5His6
<220> FEATURE:
<221> NAME/KEY: CDS
<222> LOCATION: (1)..(636)

<400> SEQUENCE: 43

```
atg gag aca gac aca ctc ctg cta tgg gta ctg ctg ctc tgg gtt cca      48
Met Glu Thr Asp Thr Leu Leu Leu Trp Val Leu Leu Leu Trp Val Pro
1               5                   10                  15 ggt tcc act ggt gac gct agc ctg aac cga agg aag aag caa gtg ggc      96
Gly Ser Thr Gly Asp Ala Ser Leu Asn Arg Arg Lys Lys Gln Val Gly
            20                  25                  30 act ggc ctg ggg ggc aac tgc aca ggc tgt atc atc tgc tca gag gag     144
Thr Gly Leu Gly Gly Asn Cys Thr Gly Cys Ile Ile Cys Ser Glu Glu
        35                  40                  45 aac ggc tgt tcc acc tgc cag cag agg ctc ttc ctg ttc atc cgc cgg     192
Asn Gly Cys Ser Thr Cys Gln Gln Arg Leu Phe Leu Phe Ile Arg Arg
    50                  55                  60 gaa ggc atc cgc cag tac ggc aag tgc ctg cac gac tgt ccc cct ggg     240
Glu Gly Ile Arg Gln Tyr Gly Lys Cys Leu His Asp Cys Pro Pro Gly
65                  70                  75                  80 tac ttc ggc atc cgc ggc cag gag gtc aac agg tgc aaa aaa tgt ggg     288
Tyr Phe Gly Ile Arg Gly Gln Glu Val Asn Arg Cys Lys Lys Cys Gly
                85                  90                  95 gcc act tgt gag agc tgc ttc agc cag gac ttc tgc atc cgg tgc aag     336
Ala Thr Cys Glu Ser Cys Phe Ser Gln Asp Phe Cys Ile Arg Cys Lys
            100                 105                 110 agg cag ttt tac ttg tac aag ggg aag tgt ctg ccc acc tgc ccg ccg     384
Arg Gln Phe Tyr Leu Tyr Lys Gly Lys Cys Leu Pro Thr Cys Pro Pro
        115                 120                 125 ggc act ttg gcc cac cag aac aca cgg gag tgc cag gag agg agc ccc     432
Gly Thr Leu Ala His Gln Asn Thr Arg Glu Cys Gln Glu Arg Ser Pro
    130                 135                 140 ggc cag aag aag ggc agg aag gac cgg cgc cca cgc aag gac agg aag     480
Gly Gln Lys Lys Gly Arg Lys Asp Arg Arg Pro Arg Lys Asp Arg Lys
145                 150                 155                 160 ctg gac cgc agg ctg gac gtg agg ccg cgc cag ccc ggc ctg cag ccc     528
Leu Asp Arg Arg Leu Asp Val Arg Pro Arg Gln Pro Gly Leu Gln Pro
                165                 170                 175 ggc ggc cgc tcg agt cta gag ggc ccg cgg ttc gaa ggt aag cct atc     576
Gly Gly Arg Ser Ser Leu Glu Gly Pro Arg Phe Glu Gly Lys Pro Ile
            180                 185                 190 cct aac cct ctc ctc ggt ctc gat tct acg cgt acc ggt cat cat cac     624
Pro Asn Pro Leu Leu Gly Leu Asp Ser Thr Arg Thr Gly His His His
        195                 200                 205 cat cac cat tga                                                     636
His His His
    210
```

<210> SEQ ID NO 44
<211> LENGTH: 211
<212> TYPE: PRT
<213> ORGANISM: Artificial sequence
<220> FEATURE:
<223> OTHER INFORMATION: Synthetic Construct

<400> SEQUENCE: 44

```
Met Glu Thr Asp Thr Leu Leu Leu Trp Val Leu Leu Leu Trp Val Pro
1               5                   10                  15
```

```
Gly Ser Thr Gly Asp Ala Ser Leu Asn Arg Arg Lys Lys Gln Val Gly
            20                  25                  30

Thr Gly Leu Gly Gly Asn Cys Thr Gly Cys Ile Ile Cys Ser Glu Glu
        35                  40                  45

Asn Gly Cys Ser Thr Cys Gln Gln Arg Leu Phe Leu Phe Ile Arg Arg
    50                  55                  60

Glu Gly Ile Arg Gln Tyr Gly Lys Cys Leu His Asp Cys Pro Pro Gly
65                  70                  75                  80

Tyr Phe Gly Ile Arg Gly Gln Glu Val Asn Arg Cys Lys Lys Cys Gly
            85                  90                  95

Ala Thr Cys Glu Ser Cys Phe Ser Gln Asp Phe Cys Ile Arg Cys Lys
        100                 105                 110

Arg Gln Phe Tyr Leu Tyr Lys Gly Lys Cys Leu Pro Thr Cys Pro Pro
            115                 120                 125

Gly Thr Leu Ala His Gln Asn Thr Arg Glu Cys Gln Glu Arg Ser Pro
    130                 135                 140

Gly Gln Lys Lys Gly Arg Lys Asp Arg Arg Pro Arg Lys Asp Arg Lys
145                 150                 155                 160

Leu Asp Arg Arg Leu Asp Val Arg Pro Arg Gln Pro Gly Leu Gln Pro
                165                 170                 175

Gly Gly Arg Ser Ser Leu Glu Gly Pro Arg Phe Glu Gly Lys Pro Ile
            180                 185                 190

Pro Asn Pro Leu Leu Gly Leu Asp Ser Thr Arg Thr Gly His His His
        195                 200                 205

His His His
    210

<210> SEQ ID NO 45
<211> LENGTH: 28
<212> TYPE: DNA
<213> ORGANISM: Artificial sequence
<220> FEATURE:
<223> OTHER INFORMATION: F primer for making adenovator CMV5 Intron
      modification EG 6

<400> SEQUENCE: 45 caccccctagg tcaatattgg ccattagc                                      28

<210> SEQ ID NO 46
<211> LENGTH: 28
<212> TYPE: DNA
<213> ORGANISM: Artificial sequence
<220> FEATURE:
<223> OTHER INFORMATION: R primer for making adenovator CMV5 Intron
      modification EG 6

<400> SEQUENCE: 46 caccccctagg taggcatccc cagcatgc                                      28

<210> SEQ ID NO 47
<211> LENGTH: 8914
<212> TYPE: DNA
<213> ORGANISM: Artificial sequence
<220> FEATURE:
<223> OTHER INFORMATION: pAdenovator-CMVIntron(Transfer Vector):

<400> SEQUENCE: 47
taacatcatc aataatatac cttatttttgg attgaagcca atatgataat gagggggtgg    60
agtttgtgac gtggcgcggg gcgtgggaac ggggcgggtg acgtagtagt gtggcggaag   120
```

```
tgtgatgttg caagtgtggc ggaacacatg taagcgacgg atgtggcaaa agtgacgttt      180
ttggtgtgcg ccgtgtaca caggaagtga caattttcgc gcggttttag gcggatgttg      240
tagtaaattt gggcgtaacc gagtaagatt tggccatttt cgcgggaaaa ctgaataaga      300
ggaagtgaaa tctgaataat tttgtgttac tcatagcgcg taatactgcg atctatacat      360
tgaatcaata ttggcaatta gccatattag tcattggtta tatagcataa atcaatattg      420
gctattggcc attgcatacg ttgtatctat atcataatat gtacatttat attggctcat      480
gtccaatatg accgccatgt tgacattgat tattgactag gtcaatattg gccattagcc      540
atattattca ttggttatat agcataaatc aatattggct attggccatt gcatacgttg      600
tatctatatc ataatatgta catttatatt ggctcatgtc caatatgacc gccatgttgg      660
cattgattat tgactagtta ttaatagtaa tcaattacgg ggtcattagt tcatagccca      720
tatatggagt tccgcgttac ataacttacg gtaaatggcc cgcctggctg accgcccaac      780
gacccccgcc cattgacgtc aataatgacg tatgttccca tagtaacgcc aatagggact      840
ttccattgac gtcaatgggt ggagtattta cggtaaactg cccacttggc agtacatcaa      900
gtgtatcata tgccaagtcc gcccccTATT gacgtcaatg acggtaaatg gcccgcctgg      960
cattatgccc agtacatgac cttacgggac tttcctactt ggcagtacat ctacgtatta     1020
gtcatcgcta ttaccatggt gatgcggttt tggcagtaca ccaatgggcg tggatagcgg     1080
tttgactcac ggggatttcc aagtctccac cccattgacg tcaatgggag tttgttttgg     1140
caccaaaatc aacgggactt tccaaaatgt cgtaataacc ccgccccgtt gacgcaaatg     1200
ggcggtaggc gtgtacggtg ggaggtctat ataagcagag ctcgtttagt gaaccgtcag     1260
atcactagaa gctttattgc ggtagtttat cacagttaaa ttgctaacgc agtcagtgct     1320
tctgacacaa cagtctcgaa cttaagctgc agaagttggt cgtgaggcac tgggcaggta     1380
agtatcaagg ttacaagaca ggtttaagga gaccaataga aactgggctt gtcgagacag     1440
agaagactct tgcgtttctg ataggcacct attggtctta ctgacatcca ctttgccttt     1500
ctctccacag gtgtccactc ccagttcaat tacagctctt aaggctagag tacttaatac     1560
gactcactat aggctagcct cgagaattca cgcgtggtac cgagctcgga tccactagtc     1620
cagtgtggtg gaattgccct taagggcaat tctgcagata ccagcacag tggcggccgc     1680 tcgagtctag agggcccgcg gttcgaaggt aagcctatcc ctaaccctct cctcggtctc     1740
gattctacgc gtaccggtca tcatcaccat caccattgag ttcaaacccg ctgatcagcc     1800
tcgactgtgc cttctagttg ccagccatct gttgtttgcc cctcccccgt gccttccttg     1860
accctggaag gtgccactcc cactgtcctt tcctaataaa atgaggaaat tgcatcgcat     1920
tgtctgagta ggtgtcattc tattctgggg ggtgggtgg ggcaggacag caaggggag      1980 gattgggaag acaatagcag gcatgctggg gatgcctacc tagtcactac tctgtgctat     2040
ggtgttcaat gcttttcaag atacccggat catatgaaac ggcatgactt tttcaagagt     2100
gccatgcccg aaggttatgt acaggaaagg accatcttct tcaaagatga cggcaactac     2160
aagacacgtg ctgaagtcaa gtttgaaggt gatacccttg ttaatagaat cgagttaaaa     2220
ggtattgact tcaaggaaga tggcaacatt ctgggacaca aattggaata caactataac     2280
tcacacaatg tatacatcat ggcagacaaa caaaagaatg gaatcaaagt gaacttcaag     2340
acccgccaca acattgaaga tggaagcgtt caactagcag accattatca acaaaatact     2400
ccaattggcg atggccctgt ccttttacca gacaaccatt acctgtccac acaatctgcc     2460
```

```
ctttcgaaag atcccaacga aaagagagac cacatggtcc ttcttgagtt tgtaacagct    2520
gctgggatta cacatggcat ggatgaactg tacaactgag gatcccccga cctcgacctc    2580
tggctaataa aggaaattta ttttcattgc aatagtgtgt tggaattttt tgtgtctctc    2640
actcggaagg acatatggga gggcaaatca tttggtcgag atccctcgga gatcggatct    2700
gggcgtggtt aagggtggga agaatatat aaggtggggg tcttatgtag ttttgtatct    2760
gttttgcagc agccgccgcc gccatgagca ccaactcgtt tgatggaagc attgtgagct    2820
catatttgac aacgcgcatg cccccatggg ccggggtgcg tcagaatgtg atgggctcca    2880
gcattgatgg tcgccccgtc ctgcccgcaa actctactac cttgacctac gagaccgtgt    2940
ctggaacgcc gttggagact gcagcctccg ccgccgcttc agccgctgca gccaccgccc    3000
gcgggattgt gactgacttt gctttcctga gcccgcttgc aagcagtgca gcttcccgtt    3060
catccgcccg cgatgacaag ttgacggctc ttttggcaca attggattct tgacccggg    3120 aacttaatgt cgtttctcag cagctgttgg atctgcgcca gcaggtttct gccctgaagg    3180
cttcctcccc tcccaatgcg gtttaaaaca taaataaaaa accagactct gtttggatt    3240 ggatcaagca agtgtcttgc tgtctttatt taggggtttt gcgcgcgcgg taggcccggg    3300
accagcggtc tcggtcgttg agggtcctgt gtatttttc caggacgtgg taaaggtgac    3360
tctggatgtt cagatacatg gcataagcc cgtctctggg gtggaggtag caccactgca    3420
gagcttcatg ctgcggggtg gtgttgtaga tgatccagtc gtagcaggag cgctgggcgt    3480
ggtgcctaaa aatgtctttc agtagcaagc tgattgccag gggcaggccc ttggtgtaag    3540
tgtttacaaa gcggttaagc tgggatgggt gcatacgtgg ggatatgaga tgcatcttgg    3600
actgtatttt taggttggct atgttcccag ccatatccct ccggggattc atgttgtgca    3660
gaaccaccag cacagtgtat ccggtgcact tgggaaattt gtcatgtagc ttagaaggaa    3720
atgcgtggaa gaacttggag acgcccttgt gacctccaag attttccatg cattcgtcca    3780
taatgatggc aatgggccca cgggcggcgg cctgggcgaa gatatttctg ggatcactaa    3840
cgtcatagtt gtgttccagg atgagatcgt cataggccat ttttacaaag cgcgggcgga    3900
gggtgccaga ctgcggtata atggttccat ccggcccagg ggcgtagtta ccctcacaga    3960
tttgcatttc ccacgctttg agttcagatg gggggatcat gtctacctgc ggggcgatga    4020
agaaaacggt ttccggggta ggggagatca gctgggaaga aagcaggttc ctgagcagct    4080
gcgacttacc gcagccggtg ggcccgtaaa tcacacctat taccgggtgc aactggtagt    4140
taagagagct gcagctgccg tcatccctga gcagggggggc cacttcgtta agcatgtccc    4200
tgactcgcat gttttccctg accaaatccg ccagaaggcg ctcgccgccc agcgatagca    4260
gttcttgcaa ggaagcaaag ttttcaacg gtttgagacc gtccgccgta ggcatgcttt    4320
tgagcgtttg accaagcagt ccaggcggt cccacagctc ggtcacctgc tctacggcat    4380
ctcgatccag catatctcct cgtttcgcgg gttgggcgcg ctttcgctgt acggcagtag    4440
tcggtgctcg tccagacggg ccagggtcat gtctttccac gggcgcaggg tcctcgtcag    4500
cgtagtctgg gtcacggtga aggggtgcgc tccgggctgc gcgctggcca gggtgcgctt    4560
gaggctggtc ctgctggtgc tgaagcgctg ccggtcttcg ccctgcgcgt cggccaggta    4620
gcatttgacc atggtgtcat agtccagccc ctccgcggcg tgcccttgg cgcgcagctt    4680 gcccttggag gaggcgccgc acgaggggca gtgcagactt tgagggcgt agagcttggg    4740 cgcgagaaat accgattccg gggagtaggc atcgcgccg caggcccgc agacggtctc    4800 gcattccacg agccaggtga gctctggccg ttcggggtca aaaaccaggt ttcccccatg    4860
```

```
cttttttgatg cgtttcttac ctctggtttc catgagccgg tgtccacgct cggtgacgaa    4920
aaggctgtcc gtgtccccgt atacagactt gagagggagt ttaaacgaat tcaatagctt    4980
gttgcatggg cggcgatata aaatgcaagg tgctgctcaa aaaatcaggc aaagcctcgc    5040
gcaaaaaaga aagcacatcg tagtcatgct catgcagata aaggcaggta agctccggaa    5100
ccaccacaga aaaagacacc attttttctct caaacatgtc tgcgggtttc tgcataaaca    5160
caaaataaaa taacaaaaaa acatttaaac attagaagcc tgtcttacaa caggaaaaac    5220
aacccttata agcataagac ggactacggc catgccggcg tgaccgtaaa aaactggtc    5280 accgtgatta aaaagcacca ccgacagctc ctcggtcatg tccggagtca taatgtaaga    5340
ctcggtaaac acatcaggtt gattcatcgg tcagtgctaa aaagcgaccg aaatagcccg    5400
ggggaataca tacccgcagg cgtagagaca acattacagc ccccatagga ggtataacaa    5460
aattaatagg agagaaaaac acataaacac ctgaaaaacc ctcctgccta ggcaaaatag    5520
caccctcccg ctccagaaca acatacagcg cttcacagcg gcagcctaac agtcagcctt    5580
accagtaaaa aagaaaacct attaaaaaaa caccactcga cacggcacca gctcaatcag    5640
tcacagtgta aaaagggcc aagtgcagag cgagtatata taggactaaa aaatgacgta    5700
acggttaaag tccacaaaaa acacccgaaa aaccgcacgc gaacctacgc ccagaaacga    5760
aagccaaaaa acccacaact tcctcaaatc gtcacttccg tttttcccacg ttacgtaact    5820 tcccattttta agaaaactac aattcccaac acataccaagt tactccgccc taaaacctac    5880
gtcacccgcc ccgttccac gccccgcgcc acgtcacaaa ctccacccccc tcattatcat    5940 attggcttca atccaaaata aggtatatta ttgatgatgt taattaacat gcatggatcc    6000
atatgcggtg tgaaataccg cacagatgcg taaggagaaa ataccgcatc aggcgctctt    6060
ccgcttcctc gctcactgac tcgctgcgct cggtcgttcg gctgcggcga gcggtatcag    6120
ctcactcaaa ggcggtaata cggttatcca cagaatcagg ggataacgca ggaaagaaca    6180
tgtgagcaaa aggccagcaa aaggccagga accgtaaaaa ggccgcgttg ctggcgtttt    6240
tccataggct ccgcccccct gacgagcatc acaaaaatcg acgctcaagt cagaggtggc    6300
gaaacccgac aggactataa agataccagg cgtttccccc tggaagctcc ctcgtgcgct    6360
ctcctgttcc gaccctgccg cttaccggat acctgtccgc ctttctccct tcgggaagcg    6420
tggcgctttc tcatagctca cgctgtaggt atctcagttc ggtgtaggtc gttcgctcca    6480
agctgggctg tgtgcacgaa ccccccgttc agcccgaccg ctgcgcctta tccggtaact    6540
atcgtcttga gtccaacccg gtaagacacg acttatcgcc actggcagca gccactggta    6600
acaggattag cagagcgagg tatgtaggcg gtgctacaga gttcttgaag tggtggccta    6660
actacggcta cactagaagg acagtatttg gtatctgcgc tctgctgaag ccagttacct    6720
tcggaaaaag agttggtagc tcttgatccg gcaaacaaac caccgctggt agcggtggtt    6780 ttttttgtttg caagcagcag attacgcgca gaaaaaaagg atctcaagaa gatcctttga    6840
tcttttctac ggggtctgac gctcagtgga acgaaaactc acgttaaggg attttggtca    6900
tgagattatc aaaaaggatc ttcacctaga tccttttaaa ttaaaaatga agttttaaat    6960
caatctaaag tatatatgag taaacttggt ctgacagtta ccaatgctta atcagtgagg    7020
cacctatctc agcgatctgt ctatttcgtt catccatagt tgcctgactc cccgtcgtgt    7080
agataactac gatacgggag ggcttaccat ctggccccag tgctgcaatg ataccgcgag    7140
acccacgctc accggctcca gatttatcag caataaacca gccagccgga agggccgagc    7200
```

-continued

```
gcagaagtgg tcctgcaact ttatccgcct ccatccagtc tattaattgt tgccgggaag    7260
ctagagtaag tagttcgcca gttaatagtt tgcgcaacgt tgttgccatt gctgcagcca    7320
tgagattatc aaaaaggatc ttcacctaga tccttttcac gtagaaagcc agtccgcaga    7380
aacggtgctg accccggatg aatgtcagct actgggctat ctggacaagg gaaaacgcaa    7440
gcgcaaagag aaagcaggta gcttgcagtg gcttacatg gcgatagcta gactgggcgg     7500 tttatggac agcaagcgaa ccggaattgc cagctggggc gccctctggt aaggttggga     7560
agccctgcaa agtaaactgg atggctttct cgccgccaag gatctgatgg cgcaggggat    7620
caagctctga tcaagagaca ggatgaggat cgtttcgcat gattgaacaa gatggattgc    7680
acgcaggttc tccggccgct tgggtggaga ggctattcgg ctatgactgg gcacaacaga    7740
caatcggctg ctctgatgcc gccgtgttcc ggctgtcagc gcaggggcgc ccggttcttt    7800
ttgtcaagac cgacctgtcc ggtgccctga atgaactgca agacgaggca gcgcggctat    7860
cgtggctggc cacgacgggc gttccttgcg cagctgtgct cgacgttgtc actgaagcgg    7920
gaagggactg gctgctattg ggcgaagtgc cggggcagga tctcctgtca tctcaccttg    7980
ctcctgccga gaaagtatcc atcatggctg atgcaatgcg gcggctgcat acgcttgatc    8040
cggctacctg cccattcgac caccaagcga acatcgcat cgagcgagca cgtactcgga    8100
tggaagccgg tcttgtcgat caggatgatc tggacgaaga gcatcagggg ctcgcgccag    8160
ccgaactgtt cgccaggctc aaggcgagca tgcccgacgg cgaggatctc gtcgtgaccc    8220
atggcgatgc ctgcttgccg aatatcatgg tggaaaatgg ccgcttttct ggattcatcg    8280
actgtggccg gctgggtgtg gcggaccgct atcaggacat agcgttggct acccgtgata    8340
ttgctgaaga gcttggcggc gaatgggctg accgcttcct cgtgctttac ggtatcgccg    8400
ctcccgattc gcagcgcatc gccttctatc gccttcttga cgagttcttc tgaattttgt    8460 taaaatttt gttaaatcag ctcatttttt aaccaatagg ccgaaatcgg caacatccct    8520
tataaatcaa agaatagac cgcgatagg ttgagtgttg ttccagtttg gaacaagagt     8580
ccactattaa agaacgtgga ctccaacgtc aaagggcgaa aaaccgtcta tcagggcgat    8640
ggcccactac gtgaaccatc acccaaatca gttttttgc ggtcgaggtg ccgtaaagct    8700
ctaaatcgga accctaaagg gagcccccga tttagagctt gacggggaaa gccggcgaac    8760
gtggcgagaa aggaagggaa gaaagcgaaa ggagcgggcg ctagggcgct ggcaagtgta    8820
gcggtcacgc tgcgcgtaac caccacaccc gcgcgcttaa tgcgccgcta cagggcgcgt    8880
ccattcgcca ttcaggatcg aattaattct taat                               8914
```

<210> SEQ ID NO 48
<211> LENGTH: 224
<212> TYPE: PRT
<213> ORGANISM: Homo sapiens

<400> SEQUENCE: 48

```
Met Arg Ala Pro Leu Cys Leu Leu Leu Val Ala His Ala Val Asp
1               5                   10                  15

Met Leu Ala Leu Asn Arg Arg Lys Lys Gln Val Gly Thr Gly Leu Gly
                20                  25                  30

Gly Asn Cys Thr Gly Cys Ile Ile Cys Ser Glu Glu Asn Gly Cys Ser
            35                  40                  45

Thr Cys Gln Gln Arg Leu Phe Leu Phe Ile Arg Arg Glu Gly Ile Arg
        50                  55                  60

Gln Tyr Gly Lys Cys Leu His Asp Cys Pro Pro Gly Tyr Phe Gly Ile
```

```
                65                  70                  75                  80
Arg Gly Gln Glu Val Asn Arg Cys Lys Lys Cys Gly Ala Thr Cys Glu
                        85                  90                  95

Ser Cys Phe Ser Gln Asp Phe Cys Ile Arg Cys Lys Arg Gln Phe Tyr
                100                 105                 110

Leu Tyr Lys Gly Lys Cys Leu Pro Thr Cys Pro Pro Gly Thr Leu Ala
                115                 120                 125

His Gln Asn Thr Arg Glu Cys Gln Gly Glu Cys Glu Leu Gly Pro Trp
                130                 135                 140

Gly Gly Trp Ser Pro Cys Thr His Asn Gly Lys Thr Cys Gly Ser Ala
145                 150                 155                 160

Trp Gly Leu Glu Ser Arg Val Arg Glu Ala Gly Arg Ala Gly His Glu
                165                 170                 175

Glu Ala Ala Thr Cys Gln Val Leu Ser Glu Ser Arg Lys Cys Pro Ile
                180                 185                 190

Gln Arg Pro Cys Pro Gly Glu Arg Ser Pro Gly Gln Lys Lys Gly Arg
                195                 200                 205

Lys Asp Arg Arg Pro Arg Lys Asp Arg Lys Leu Asp Arg Arg Leu Asp
                210                 215                 220

<210> SEQ ID NO 49
<211> LENGTH: 243
<212> TYPE: PRT
<213> ORGANISM: Xenopus laevis

<400> SEQUENCE: 49

Met Gln Phe Gln Leu Phe Ser Phe Ala Leu Ile Ile Leu Asn Cys Val
1                   5                   10                  15

Asp Tyr Ser His Cys Gln Ala Ser Arg Trp Arg Arg Ser Lys Arg Ala
                20                  25                  30

Ser Tyr Gly Thr Asn Pro Ile Cys Lys Gly Cys Leu Ser Cys Ser Lys
                35                  40                  45

Asp Asn Gly Cys Leu Arg Cys Gln Pro Lys Leu Phe Phe Phe Leu Arg
50                  55                  60

Arg Glu Gly Met Arg Gln Tyr Gly Glu Cys Leu Gln Ser Cys Pro Pro
65                  70                  75                  80

Gly Tyr Tyr Gly Val Arg Gly Pro Asp Met Asn Arg Cys Ser Arg Cys
                        85                  90                  95

Arg Ile Glu Asn Cys Asp Ser Cys Phe Ser Arg Asp Phe Cys Ile Lys
                100                 105                 110

Cys Lys Ser Gly Phe Tyr Ser Leu Lys Gly Gln Cys Phe Glu Glu Cys
                115                 120                 125

Pro Glu Gly Phe Ala Pro Leu Asp Asp Thr Met Val Cys Val Asp Gly
                130                 135                 140

Cys Glu Val Gly Pro Trp Ser Glu Trp Gly Thr Cys Ser Arg Asn Asn
145                 150                 155                 160

Arg Thr Cys Gly Phe Lys Trp Gly Leu Glu Thr Arg Thr Arg Gln Ile
                165                 170                 175

Val Lys Lys Pro Ala Lys Asp Thr Ile Pro Cys Pro Thr Ile Ala Glu
                180                 185                 190

Ser Arg Arg Cys Lys Met Ala Ile Arg His Cys Pro Gly Gly Lys Arg
                195                 200                 205

Thr Thr Lys Lys Lys Asp Lys Arg Asn Lys Lys Lys Lys Lys Lys Leu
                210                 215                 220
```

| | | | | | | | | | | | | | | |
|---|---|---|---|---|---|---|---|---|---|---|---|---|---|---|
| Leu | Glu | Arg | Ala | Gln | Glu | Gln | His | Ser | Val | Val | Leu | Ala | Thr | Asp | Arg |
| 225 | | | | | 230 | | | | | 235 | | | | | 240 |

Ser Ser Gln

<210> SEQ ID NO 50
<211> LENGTH: 732
<212> TYPE: DNA
<213> ORGANISM: Homo sapiens
<220> FEATURE:
<221> NAME/KEY: CDS
<222> LOCATION: (1)..(732)

<400> SEQUENCE: 50

```
atg cag ttt cgc ctt ttc tcc ttt gcc ctc atc att ctg aac tgc atg      48
Met Gln Phe Arg Leu Phe Ser Phe Ala Leu Ile Ile Leu Asn Cys Met
1               5                   10                  15 gat tac agc cac tgc caa ggc aac cga tgg aga cgc agt aag cga gct      96
Asp Tyr Ser His Cys Gln Gly Asn Arg Trp Arg Arg Ser Lys Arg Ala
            20                  25                  30 agt tat gta tca aat ccc att tgc aag ggt tgt ttg tct tgt tca aag     144
Ser Tyr Val Ser Asn Pro Ile Cys Lys Gly Cys Leu Ser Cys Ser Lys
        35                  40                  45 gac aat ggg tgt agc cga tgt caa cag aag ttg ttc ttc ttc ctt cga     192
Asp Asn Gly Cys Ser Arg Cys Gln Gln Lys Leu Phe Phe Phe Leu Arg
    50                  55                  60 aga gaa ggg atg cgc cag tat gga gag tgc ctg cat tcc tgc cca tcc     240
Arg Glu Gly Met Arg Gln Tyr Gly Glu Cys Leu His Ser Cys Pro Ser
65                  70                  75                  80 ggg tac tat gga cac cga gcc cca gat atg aac aga tgt gca aga tgc     288
Gly Tyr Tyr Gly His Arg Ala Pro Asp Met Asn Arg Cys Ala Arg Cys
                85                  90                  95 aga ata gaa aac tgt gat tct tgc ttt agc aaa gac ttt tgt acc aag     336
Arg Ile Glu Asn Cys Asp Ser Cys Phe Ser Lys Asp Phe Cys Thr Lys
            100                 105                 110 tgc aaa gta ggc ttt tat ttg cat aga ggc cgt tgc ttt gat gaa tgt     384
Cys Lys Val Gly Phe Tyr Leu His Arg Gly Arg Cys Phe Asp Glu Cys
        115                 120                 125 cca gat ggt ttt gca cca tta gaa gaa acc atg gaa tgt gtg gaa gga     432
Pro Asp Gly Phe Ala Pro Leu Glu Glu Thr Met Glu Cys Val Glu Gly
    130                 135                 140 tgt gaa gtt ggt cat tgg agc gaa tgg gga act tgt agc aga aat aat     480
Cys Glu Val Gly His Trp Ser Glu Trp Gly Thr Cys Ser Arg Asn Asn
145                 150                 155                 160 cgc aca tgt gga ttt aaa tgg ggt ctg gaa acc aga aca cgg caa att     528
Arg Thr Cys Gly Phe Lys Trp Gly Leu Glu Thr Arg Thr Arg Gln Ile
                165                 170                 175 gtt aaa aag cca gtg aaa gac aca ata ccg tgt cca acc att gct gaa     576
Val Lys Lys Pro Val Lys Asp Thr Ile Pro Cys Pro Thr Ile Ala Glu
            180                 185                 190 tcc agg aga tgc aag atg aca atg agg cat tgt cca gga ggg aag aga     624
Ser Arg Arg Cys Lys Met Thr Met Arg His Cys Pro Gly Gly Lys Arg
        195                 200                 205 aca cca aag gcg aag gag aag agg aac aag aaa aag aaa agg aag ctg     672
Thr Pro Lys Ala Lys Glu Lys Arg Asn Lys Lys Lys Arg Lys Leu
    210                 215                 220 ata gaa agg gcc cag gag caa cac agc gtc ttc cta gct aca gac aga     720
Ile Glu Arg Ala Gln Glu Gln His Ser Val Phe Leu Ala Thr Asp Arg
225                 230                 235                 240 gct aac caa taa                                                      732
Ala Asn Gln
```

```
<210> SEQ ID NO 51
<211> LENGTH: 243
<212> TYPE: PRT
<213> ORGANISM: Homo sapiens

<400> SEQUENCE: 51

Met Gln Phe Arg Leu Phe Ser Phe Ala Leu Ile Ile Leu Asn Cys Met
1               5                   10                  15

Asp Tyr Ser His Cys Gln Gly Asn Arg Trp Arg Ser Lys Arg Ala
            20                  25                  30

Ser Tyr Val Ser Asn Pro Ile Cys Lys Gly Cys Leu Ser Cys Ser Lys
            35                  40                  45

Asp Asn Gly Cys Ser Arg Cys Gln Gln Lys Leu Phe Phe Phe Leu Arg
        50                  55                  60

Arg Glu Gly Met Arg Gln Tyr Gly Glu Cys Leu His Ser Cys Pro Ser
65              70                  75                  80

Gly Tyr Tyr Gly His Arg Ala Pro Asp Met Asn Arg Cys Ala Arg Cys
                85                  90                  95

Arg Ile Glu Asn Cys Asp Ser Cys Phe Ser Lys Asp Phe Cys Thr Lys
            100                 105                 110

Cys Lys Val Gly Phe Tyr Leu His Arg Gly Arg Cys Phe Asp Glu Cys
        115                 120                 125

Pro Asp Gly Phe Ala Pro Leu Glu Glu Thr Met Glu Cys Val Glu Gly
    130                 135                 140

Cys Glu Val Gly His Trp Ser Glu Trp Gly Thr Cys Ser Arg Asn Asn
145                 150                 155                 160

Arg Thr Cys Gly Phe Lys Trp Gly Leu Glu Thr Arg Thr Arg Gln Ile
                165                 170                 175

Val Lys Lys Pro Val Lys Asp Thr Ile Pro Cys Pro Thr Ile Ala Glu
            180                 185                 190

Ser Arg Arg Cys Lys Met Thr Met Arg His Cys Pro Gly Gly Lys Arg
        195                 200                 205

Thr Pro Lys Ala Lys Glu Lys Arg Asn Lys Lys Lys Arg Lys Leu
    210                 215                 220

Ile Glu Arg Ala Gln Glu Gln His Ser Val Phe Leu Ala Thr Asp Arg
225                 230                 235                 240

Ala Asn Gln

<210> SEQ ID NO 52
<211> LENGTH: 29
<212> TYPE: DNA
<213> ORGANISM: Artificial
<220> FEATURE:
<223> OTHER INFORMATION: Primer Sequence

<400> SEQUENCE: 52
ccggctagcc aaggcaaccg atggagacg                                              29

<210> SEQ ID NO 53
<211> LENGTH: 34
<212> TYPE: DNA
<213> ORGANISM: Artificial
<220> FEATURE:
<223> OTHER INFORMATION: Primer Sequence

<400> SEQUENCE: 53
gtagcggccg ctcaccctcc tggacaatgc ctca                                        34
```

<210> SEQ ID NO 54
<211> LENGTH: 702
<212> TYPE: DNA
<213> ORGANISM: Homo sapiens

<400> SEQUENCE: 54

| | | | | | |
|---|---|---|---|---|---|
| atggagacag | acacactcct | gctatgggta | ctgctgctct | gggttccagg | ttccactggt | 60 |
| gacgctagcg | ctagttatgt | atcaaatccc | atttgcaagg | gttgtttgtc | ttgttcaaag | 120 |
| gacaatgggt | gtagccgatg | tcaacagaag | ttgttcttct | tccttcgaag | agaagggatg | 180 |
| cgccagtatg | gagagtgcct | gcattcctgc | ccatccgggt | actatggaca | ccgagcccca | 240 |
| gatatgaaca | gatgtgcaag | atgcagaata | gaaaactgtg | attcttgctt | tagcaaagac | 300 |
| ttttgtacca | agtgcaaagt | aggctttat | ttgcatagag | gccgttgctt | tgatgaatgt | 360 |
| ccagatggtt | ttgcaccatt | agaagaaacc | atggaatgtg | tggaaggatg | tgaagttggt | 420 |
| cattggagcg | aatggggaac | ttgtagcaga | aataatcgca | catgtggatt | taaatgggt | 480 |
| ctggaaacca | gaacacggca | aattgttaaa | aagccagtga | agacacaat | accgtgtcca | 540 |
| accattgctg | aatccaggag | atgcaagatg | acaatgaggc | attgtccagg | aggggcggc | 600 |
| cgctcgagtc | tagagggccc | gcggttcgaa | ggtaagccta | tccctaaccc | tctcctcggt | 660 |
| ctcgattcta | cgcgtaccgg | tcatcatcac | catcaccatt | ga | | 702 |

<210> SEQ ID NO 55
<211> LENGTH: 233
<212> TYPE: PRT
<213> ORGANISM: Homo sapiens

<400> SEQUENCE: 55

Met Glu Thr Asp Thr Leu Leu Leu Trp Val Leu Leu Leu Trp Val Pro
1               5                   10                  15

Gly Ser Thr Gly Asp Ala Ser Ala Ser Tyr Val Ser Asn Pro Ile Cys
            20                  25                  30

Lys Gly Cys Leu Ser Cys Ser Lys Asp Asn Gly Cys Ser Arg Cys Gln
        35                  40                  45

Gln Lys Leu Phe Phe Phe Leu Arg Arg Glu Gly Met Arg Gln Tyr Gly
    50                  55                  60

Glu Cys Leu His Ser Cys Pro Ser Gly Tyr Tyr Gly His Arg Ala Pro
65                  70                  75                  80

Asp Met Asn Arg Cys Ala Arg Cys Arg Ile Glu Asn Cys Asp Ser Cys
                85                  90                  95

Phe Ser Lys Asp Phe Cys Thr Lys Cys Lys Val Gly Phe Tyr Leu His
            100                 105                 110

Arg Gly Arg Cys Phe Asp Glu Cys Pro Asp Gly Phe Ala Pro Leu Glu
        115                 120                 125

Glu Thr Met Glu Cys Val Glu Gly Cys Glu Val Gly His Trp Ser Glu
    130                 135                 140

Trp Gly Thr Cys Ser Arg Asn Asn Arg Thr Cys Gly Phe Lys Trp Gly
145                 150                 155                 160

Leu Glu Thr Arg Thr Arg Gln Ile Val Lys Lys Pro Val Lys Asp Thr
                165                 170                 175

Ile Pro Cys Pro Thr Ile Ala Glu Ser Arg Arg Cys Lys Met Thr Met
            180                 185                 190

Arg His Cys Pro Gly Gly Gly Gly Arg Ser Ser Leu Glu Gly Pro Arg
        195                 200                 205

-continued

```
Phe Glu Gly Lys Pro Ile Pro Asn Pro Leu Leu Gly Leu Asp Ser Thr
    210                 215                 220

Arg Thr Gly His His His His His His
225                 230
```